US011274282B2

(12) United States Patent
Rodriguez et al.

(10) Patent No.: US 11,274,282 B2
(45) Date of Patent: Mar. 15, 2022

(54) VESICULAR STOMATITIS VECTORS ENCODING CRIMEAN-CONGO HEMORRHAGIC FEVER ANTIGEN

(71) Applicant: THE BOARD OF REGENTS OF THE UNIVERSITY OF TEXAS SYSTEM, Austin, TX (US)

(72) Inventors: Sergio E. Rodriguez, Galveston, TX (US); Robert W. Cross, Galveston, TX (US); Chad E. Mire, Galveston, TX (US); Thomas W. Geisbert, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 138 days.

(21) Appl. No.: 16/875,056

(22) Filed: May 15, 2020

(65) Prior Publication Data

US 2020/0362316 A1 Nov. 19, 2020

Related U.S. Application Data

(60) Provisional application No. 62/848,277, filed on May 15, 2019.

(51) Int. Cl.
| | |
|---|---|
| *A61K 39/00* | (2006.01) |
| *A61K 39/12* | (2006.01) |
| *A61K 39/23* | (2006.01) |
| *C12N 15/00* | (2006.01) |
| *C12N 15/74* | (2006.01) |
| *C12N 7/00* | (2006.01) |
| *C07K 14/005* | (2006.01) |
| *A61K 39/205* | (2006.01) |
| *C12N 15/86* | (2006.01) |
| *G01N 33/569* | (2006.01) |
| *A61P 31/14* | (2006.01) |

(52) U.S. Cl.
CPC ............. *C12N 7/00* (2013.01); *A61K 39/205* (2013.01); *A61P 31/14* (2018.01); *C07K 14/005* (2013.01); *C12N 15/86* (2013.01); *G01N 33/56983* (2013.01); *A61K 2039/5256* (2013.01); *A61K 2039/54* (2013.01); *C12N 2760/20222* (2013.01); *C12N 2760/20234* (2013.01); *C12N 2760/20243* (2013.01); *C12N 2760/20251* (2013.01); *G01N 2333/08* (2013.01); *G01N 2800/26* (2013.01)

(58) Field of Classification Search
CPC .... A61K 2039/5256; A61K 2039/5258; A61K 39/00; A61K 39/12; A61P 11/00
See application file for complete search history.

(56) References Cited

U.S. PATENT DOCUMENTS 8,012,489 B2  9/2011 Jones et al.

OTHER PUBLICATIONS

Adams et al., "Changes to taxonomy and the International Code of Virus Classification and Nomenclature ratified by the International Committee on Taxonomy of Viruses", Arch Virol, 162:2505-2538, 2017.
Ahmed et al., "Presence of broadly reactive and group-specific neutralizing epitopes on newly described isolates of Crimean-Congol hemorrhagic fever virus", Journal of General Virology, 86:3327-3336, 2005.
Altamura et al., "Identification of a Novel C-Terminal Cleavage of Crimean-Congo Hemorrhagic Fever Virus PreG$_N$ That Leads to Generation of an NS$_m$ Protein", Journal of Virology, 81(12):6632-6642, 2007.
Bente et al., "Crimean-Congo hemorrhagic fever: History, epidemiology, pathogenesis, clinical syndrome and genetic diversity", Antiviral Research, 100:159-189, 2013.
Bente et al., "Pathogenesis and Immune Response of Crimean-Congo Hemorrhagic Fever Virus in a STAT-1 Knockout Mouse Model", Journal of Virology, 84(21):11089-11100, 2010.
Bereczky et al., "Crimean-Congo hemorrhagic fever virus infection is lethal for adult type I interferon receptor-knockout mice", Journal of General Virology, 91:1473-1477, 2010.
Bergeron et al., "Crimean-Congo Hemorrhagic Fever Virus Glycoprotein Processing by the Endoprotease SKI-1/S1P is Critical for Virus Infectivity", Journal of Virology, 81(23):13271-13276, 2007.
Bergmann et al., "Passage of an integral membrane protein, the vesicular stomatitis virus glycoprotein, through the Golgi apparatus en route to the plasma membrane", Proc. Natl. Acad. Sci., 78(3):1746-1750, 1981.
Bertolotti-Ciarlet et al., "Cellular Localization and Antigenic Characterization of Crimean-Congo Hemorrhagic Fever Virus Glycoproteins", Journal of Virology, 79(10):6152-6161, 2005.
Brown et al., "Vesicular Stomatitis Virus-Based Vaccine Protects Hamsters against Lethal Challenge with Andes Virus", Journal of Virology, 85(23):12781-12791, 2011.
Buttigieg et al., "A novel Vaccine against Crimean-Congo Haemorrhagic Fever Protects 100% of Animals against Lethal Challenge in a Mouse Model", PLoS One, 9(3): e91516, 2014.
Canakoglu et al., "Immunization of Knock-Out α/β Interferon Receptor Mice against High Lethal Dose of Crimean-Congo Hemorrhagic Fever Virus with a Cell Culture Based Vaccine", PLoS Negl Trop Dis., 9(3):e0003579, 2015.
Causey et al., "Congo Virus from Domestic Livestock, African Hedgehog, and Arthropods in Nigeria", The American Journal of Tropical Medicine and Hygiene, 19(5):846-850, 1970.
Coller et al., "Clinical development of a recombinant Ebola vaccine in the midst of an unprecedented epidemic", Vaccine, 35:4465-4469, 2017.
Devignot et al., "A Virus-Like Particle System Identifies the Endonuclease Domain of Crimean-Congo Hemorrhagic Fever Virus", Journal of Virology, 89(11):5957-5967, 2015.

(Continued)

*Primary Examiner* — Barry A Chestnut

(57) ABSTRACT

Certain embodiments are directed generally to compositions and methods related to recombinant vesicular stomatitis virus vectors (ΔGrVSV) encoding Crimean-Congo Hemorrhagic Fever glycoprotein precursor (CCHFV-GPC) and forming a recombinant vesicular stomatitis virus vector encoding Crimean-Congo Hemorrhagic Fever glycoprotein precursor (ΔGrVSV-CCHFV-GPC).

18 Claims, 6 Drawing Sheets

Specification includes a Sequence Listing.

(56) References Cited

OTHER PUBLICATIONS

Dowall et al., "A Crimean-Congo hemorrhagic fever (CCHF) viral vaccine expressing nucleoprotein is immunogenic but fails to confer protection against lethal disease", *Human Vaccines & Immunotherapeutics*, 12(2):519-527, 2016.

Dowall et al., "Development of vaccines against Crimean-Congo haemorrhagic fever virus", *Vaccine*, 35:6015-6023, 2017.

Ergönül O., "Crimean-Congo Haemorrhagic fever", *Lancet Infect Dis*, 6(4):203-214, 2006.

Ergönül O., "Crimean-Congo hemorrhagic fever virus: new outbreaks, new discoveries", *Current Opinion in Virology*, 2:215-220, 2012.

Ergönül O., "Treatment of Crimean-Congo hemorrhagic fever", *Antiviral Research*, 78:125-131, 2008.

Erickson et al., "N-linked glycosylation of Gn (but not Gc) is important for Crimean Congo hemorrhagic fever virus glycoprotein localization and transport", *Virology*, 361:348-355, 2007.

Forger III et al., "Murine Infection by Vesicular Stomatitis Virus: Initial Characterization of the H-$2^d$ System", *Journal of Virology*, 65(9):4950-4958, 1991.

Fuchs et al., "First in Human Evaluation of the Safety and Immunogenicity of a Recombinant Vesicular Stomatitis Virus Human Immunodeficiency Virus-1 gag Vaccine (HVTN) 090)", *Open Forum Infect Dis.*, 2(3):ofv082, 2015.

Fukushi et al., "Vesicular stomatitis virus pseudotyped with severe acute respiratory syndrome coronavirus spike protein", *Journal of General Virology*, 86:2269-2274, 2005.

Garbutt et al., "Properties of Replication-Competent Vesicular Stomatitis Virus Vectors Expressing Glycoproteins of Filoviruses and Arenaviruses", *Journal of Virology*, 78(10):5458-5465, 2004.

Gargili et al., The role of ticks in the maintenance and transmission of Crimean-Congo hemorrhagic fever virus: A review of published field and laboratory studies, *Antiviral Research*, 144:93-119, 2017.

Garrison, et al., "A DNA vaccine for Crimean-Congo hemorrhagic fever protects against disease and death in two lethal mouse models", *PLoS Negl Trop Dis.*, 11(9):e0005908, 2017.

Garry et al., "Proteomics computational analyses suggest that the carboxyl terminal glycoproteins of Bunyaviruses are class II viral fusion protein (beta-penetrenes)", *Theoretical Biology and Medical Modelling*, 1:10, 2004.

Geisbert et al., "Recombinant Vesicular Stomatitis Virus-Based Vaccines Against Ebola and Marburg Virus Infections", *J. Infect. Dis.*, 204 Supple 3 (Suppl 3):S1075-S1081, 2011.

Geisbert et al., "Vesicular Stomatitis Virus-Based Ebola Vaccine is Well-Tolerated and Protects Immunocompromised Nonhuman Primates", *PLoS Pathogens*, 4(11):e1000225, 2008.

Ghiasi et al., "Mice Orally Immunized with a Transgenic Plant Expressing the Glycoprotein of Crimean-Congo Hermorrhagic Fever Virus", *Clinical and Vaccine Immunology*, 18(12):2031-2037, 2011.

Goedhals et al., "Identification of human linear B-cell epitope sites on the envelope glycoproteins of Crimean-Congo haemorrhagic fever virus", *Epidemiol. Infect.*, 143:1451-1456, 2015.

Halperin et al., "Six-Month Safety Data of Recombinant Vesicular Stomatitis Virus-Zaire Ebola Virus Envelope Glycoprotein Vaccine in a phase 3 Double-Blind, Placebo-Controlled Randomized Study in Healthy Adults", *The Journal of Infectious Diseases*, 215(12):1789-1798, 2017.

Henao-Restrepo et al., "Efficacy and effectiveness of an rVSV-vectored vaccine in preventing Ebola virus disease: final results from the Guinea ring vaccination, openlabel, cluster-randomised trial (Ebola ça Suffit!)", *Lancet*, 389(10068):504, 2017.

Hinkula et al., "Immunization with DNA Plasmids Coding for Crimean-Congo Hemorrhagic Fever Virus Capsid and Envelope Proteins and/or Virus-Like Particles Induces Protection and Survival in Challenged Mice", *Journal of Virology*, 91(10):e02076-16, 2017.

Huttner et al., "The effect of dose on the safety and immunogenicity of the VSV Ebola candidate vaccine: a randomized double-blind, placebo-controlled phase ½ trial", *Lancet Infect Dis*, 15:1156-1166, 2015.

Jayakar et al., "Identification of Two Additional Translation Products from the Matrix (M) Gene That Contribute to Vesicular Stomatitis Virus Cytopathology", *Journal of Virology*, 76(16): 8011-8018, 2002.

Kortekaas et al., "Crimean-Congo Hemorrhagic Fever Virus Subunit Induce High Levels of Neutralizing Antibodies But No Protection in STAT Knockout Mice", *Vector Borne Zoonotic Dis.*, 15(12):759-764, 2015.

Lawson et al., "Recombinant vesicular stomatitis viruses from DNA", *Proc. Natl. Acad. Sci. USA*, 92(10):4477-4481, 1995.

Lichty et al., "Vesicular stomatitis virus: re-inventing the bullet", *Trends Mol Med*, 10(5):210-216, 2004.

Martinez et al., "Recombinant vesicular stomatitis (Indiana) virus expressing New Jersey and Indiana glycoproteins induces neutralizing antibodies to each serotype in swine, a natural host", *Vaccine*, 22(29-30):4035-4043, 2004.

Marzi et al., "Stat1-Deficient Mice Are Not an Appropriate Model for Efficacy Testing of Recombinant Vesicular Stomatitis Virus-Based Filovirus Vaccines", *J Infect Dis.*, 212 Suppl 2(Suppl2):S404-S409, 2015.

Midilli et al., "The first clinical case due to AP92 like strain of Crimean-Congo Hemorrhagic Fever virus and a field survey", *BMC Infect Dis.*, 9:90, 2009.

Mire et al., "Durability of a Vesicular Stomatitis Virus-Based Marburg Virus Vaccine in Nonhuman Primates", *PLoS One*, 9(4):e94355, 2014.

Mire et al., "Single injection recombinant vesicular stomatitis virus vaccines protect ferrets against lethal Nipah virus disease", *Virol J.*, 10:353, 2013.

Mire et al., "Single-dose attenuated Vesiculovax vaccines protect primates against Ebola Makona virus", *Nature*, 520(7549):688-691, 2015.

Mire et al., "Vesicular Stomatitis Virus-Based Vaccines Protect Nonhuman Primates against *Bundibugyo ebolavirus*", *PLoS Negi Trop Dis.*, 7(12):e2600, 2013.

Overby et al., "The Cytoplasmic Tails of Uukuniemi Virus (*Bunyaviridae*) $G_N$ and $G_C$ Glycoproteins Are Important for Intracellular Targeting and the Budding of Virus-Like Particles", *J Virol.*, 81(20):11381-11391, 2007.

Papa et al., "A novel AP02-like Crimean-Congo hemorrhagic fever virus strain, Greece", *Ticks and Tick-borne Diseases*, 5(5):590-593, 2014.

Preble et al., "Neurovirulence Mutant of Vesicular Stomatitis Virus with an Altered Target Cell Tropism In Vivo", *Infect Immun.*, 29(2):744-757, 1980.

Sanchez et al., "Characterization of the Glycoproteins of Crimean-Congo Hemorrhagic Fever Virus", *J Virol.*, 76(14)7263-7275, 2002.

Sanchez et al., "Crimean-Congo Hemorrhagic Fever Virus Glycoprotein Precursor is Cleaved by Furin-Like and SKI-1 Proteases to Generate a Novel 38-Kilodalton Glycoprotein", *J Virol.*, 80(1):514-525, 2006.

Shi et al., "Role of the Cytoplasmic Tail Domains of Bunyamwera Orthobunyavirus Glycoproteins Gn and Gc in Virus Assembly and Morphogenesis", *J Virol.*, 81(18):10151-10160, 2007.

Shtanko et al., "Crimean-Congo Hemorrhagic Fever Virus Entry into Host Cells Occurs through the Multivesicular Body and Requires ESCRT Regulators", *PLoS Pathog*, 10(9):e1004390, 2014.

Simon et al., "Microtubule-dependent and microtubule-independent steps in Crimean-Congo hemorrhagic fever virus replication cycle", *Virology*, 385(2):313-322, 2009.

Spengler et al., "Crimean-Congo Hemorrhagic Fever in Humanized Mice Reveals Glial Cells as Primary Targets of Neurological Infection", *J Infection Dis.*, 216(11): 1386-1397, 2017.

Spik et al., "Immunogenicity of combination DNA vaccines for Rift Valley fever virus, tick-borne encephalitis virus, Hantaan virus, and Crimean Congo hemorrhagic fever virus", 24(21):4657-4666, 2006.

Suda et al., "Analysis of the entry mechanism of Crimean-Congo hemorrhagic fever virus, using a vesicular stomatitis virus pseudotyping system", *Arch Virol.*, 161(6):1447-1454, 2016.

(56) References Cited

OTHER PUBLICATIONS

Surtees et al., "Heat Shock Protein 70 Family Members Interact with Crimean-Congo Hemorrhagic Fever Virus and Hazara Virus Nucleocapsid Proteins and Perform a Functional Role in the Nairovirus Replication Cycle", *J Virol.*, 90(20):9305-9316, 2016.

Whitt, M.A., " Generation of VSV pseudotypes using recombinant ΔG-VSV for studies on virus entry, identification of entry inhibitors, and immune responses to vaccines." *J Virol Methods.*,169(2):365-374, 2010.

Xiao et al., "Identification of a putative Crimean-Congo hemorrhagic fever virus entry factor", *Biochem Biophys Res Common.*, 411 (2):253-258, 2011.

Zivcec et al., "Identification of broadly neutralizing monoclonal antibodies against Crimean-Congo hemorrhagic fever virus", *Antiviral Res.*, 146:112-120, 2017.

Zivcec et al., "Lethal Crimean-Congo Hemorrhagic Fever Virus Infection in Interferon α/β Receptor Knockout Mice is Associated With High Viral Loads, Proinflammatory Responses, and Coagulopathy", *J Infect Dis.*, 207(12):1909-1921, 2013.

SEQUENCE LISTING

```
<160> NUMBER OF SEQ ID NOS: 10

<210> SEQ ID NO 1
<211> LENGTH: 14925
<212> TYPE: DNA
<213> ORGANISM: Artificial Sequence
<220> FEATURE:
<223> OTHER INFORMATION: Recombinant DNA

<400> SEQUENCE: 1
gacgaagaca aacaaaccat tattatcatt aaaaggctca ggagaaactt taacagtaat        60
```

-continued

```
caaaatgtct gttacagtca agagaatcat tgacaacaca gtcgtagttc caaaacttcc      120
tgcaaatgag gatccagtgg aatacccggc agattacttc agaaaatcaa aggagattcc      180
tctttacatc aatactacaa aaagtttgtc agatctaaga ggatatgtct accaaggcct      240
caaatccgga aatgtatcaa tcatacatgt caacagctac ttgtatggag cattaaagga      300
catccggggt aagttggata agattggtc aagtttcgga ataaacatcg ggaaagcagg       360
ggatacaatc ggaatatttg accttgtatc cttgaaagcc ctggacggcg tacttccaga      420
tggagtatcg gatgcttcca gaaccagcgc agatgacaaa tggttgcctt tgtatctact      480
tggcttatac agagtgggca gaacacaaat gcctgaatac agaaaaaagc tcatggatgg      540
gctgacaaat caatgcaaaa tgatcaatga acagtttgaa cctcttgtgc cagaaggtcg      600
tgacattttt gatgtgtggg gaaatgacag taattacaca aaaattgtcg ctgcagtgga      660
catgttcttc cacatgttca aaaacatga atgtgcctcg ttcagatacg gaactattgt       720
ttccagattc aaagattgtg ctgcattggc aacatttgga cacctctgca aaataaccgg      780
aatgtctaca gaagatgtaa cgacctggat cttgaaccga gaagttgcag atgaaatggt      840
ccaaatgatg cttccaggcc aagaaattga caaggccgat tcatacatgc cttatttgat      900
cgactttgga ttgtcttcta gtctccata ttcttccgtc aaaaaccctg ccttccactt       960
ctgggggcaa ttgacagctc ttctgctcag atccaccaga gcaaggaatg cccgacagcc      1020
tgatgacatt gagtatacat ctcttactac agcaggtttg ttgtacgctt atgcagtagg      1080
atcctctgcc gacttggcac aacagttttg tgttggagat aacaaataca ctccagatga      1140
tagtaccgga ggattgacga ctaatgcacc gccacaaggc agagatgtgg tcgaatggct      1200
cggatggttt gaagatcaaa acagaaaacc gactcctgat atgatgcagt atgcgaaaag      1260
agcagtcatg tcactgcaag gcctaagaga aagacaatt ggcaagtatg ctaagtcaga      1320
atttgacaaa tgaccctata attctcagat cacctattat atattatgct acatatgaaa      1380
aaaactaaca gatatcatgg ataatctcac aaaagttcgt gagtatctca agtcctattc      1440
tcgtctggat caggcggtag agagataga tgagatcgaa gcacaacgag ctgaaaagtc      1500
caattatgag ttgttccaag aggatggagt ggaagagcat actaagccct cttatttca       1560 ggcagcagat gattctgaca cagaatctga accagaaatt gaagacaatc aaggcttgta      1620
tgcaccagat ccagaagctg agcaagttga aggctttata caggggcctt agatgacta      1680 tgcagatgag gaagtggatg ttgtatttac ttcggactgg aaacagcctg agcttgaatc      1740
tgacgagcat ggaaagacct tacggttgac atcgccagag ggtttaagtg agagcagaa      1800 atcccagtgg ctttcgacga ttaaagcagt cgtgcaaagt gccaaatact ggaatctggc      1860
agagtgcaca tttgaagcat cgggagaagg ggtcattatg aaggagcgcc agataactcc      1920
ggatgtatat aaggtcactc cagtgatgaa cacacatccg tcccaatcag aagcagtatc      1980
agatgtttgg tctctctcaa agacatccat gactttccaa cccaagaaag caagtcttca      2040
gcctctcacc atatccttgg atgaattgtt ctcatctaga ggagagttca tctctgtcgg      2100
aggtgacgga cgaatgtctc ataaagaggc catcctgctc ggcctgagat acaaaaagtt      2160
gtacaatcag gcgagagtca atattctct gtagactatg aaaaaaagta acagatatca       2220
cgatctaagt gttatcccaa tccattcatc atgagttcct taaagaagat tctcggtctg      2280
aaggggaaag gtaagaaatc taagaaatta gggatcgcac cacccccctta tgaagaggac     2340 actagcatgg agtatgctcc gagcgctcca attgacaaat cctatttggg agttgacgag      2400
atggacacct atgatccgaa tcaattaaga tatgagaaat tcttctttac agtgaaaatg      2460
```

```
acggttagat ctaatcgtcc gttcagaaca tactcagatg tggcagccgc tgtatcccat    2520
tgggatcaca tgtacatcgg aatggcaggg aaacgtccct tctacaaaat cttggctttt    2580
ttgggttctt ctaatctaaa ggccactcca gcggtattgg cagatcaagg tcaaccagag    2640
tatcacgctc actgcgaagg cagggcttat ttgccacata ggatggggaa gacccctccc    2700
atgctcaatg taccagagca cttcagaaga ccattcaata taggtcttta caagggaacg    2760
attgagctca caatgaccat ctacgatgat gagtcactgg aagcagctcc tatgatctgg    2820
gatcatttca attcttccaa attttctgat ttcagagaga aggccttaat gtttggcctg    2880
attgtcgaga aaaaggcatc tggagcgtgg gtcctggact ctatcggcca cttcaaatga    2940
gctagtctaa cttctagctt ctgaacaatc cccggtttac tcagtctccc ctaattccag    3000
cctctcgaac aactaatatc ctgtcttttc tatccctatg aaaaaaacta acagagatcg    3060
atctgtttac gcgttttcat catgcatatc tcactgatgt acgctatcct gtgcctgcag    3120
ctgtgcggcc tggggaaaac tcacggaagc cataacgaaa ctcgccataa caagaccgac    3180
acaatgacca cacctggcga taacccaagc tccgagcccc ctgtgagcac tgccctgtcc    3240
attaccctgg atccttctac tgtgacccca actaccctg cttccggact ggagggatct    3300
ggagaagtgt acaccagccc acccatcaca actggatctc tgccactgag tgagaccaca    3360
ccagaactgc ccgtgactac cgggacagac actctgtctg ccggagacgt ggatccaagt    3420
acccagacag caggagggac ctcagctcca accgtgagga caagcctgcc taactcacca    3480
agcactccct ccacccctca ggatactcac catcctgtcc gcaatctgct gtccgtgacc    3540
tctcctggcc cagacgaaac tagtacccca tcaggaacag gcaaggagtc tagtgccact    3600
tcaagccccc accccgtgag caataggcct ccaacacccc ctgcaactgc cagggacct    3660 actgagaacg attctcacaa tgctaccgag catccagaat cactgaccca gagcgcaaca    3720
cctggcctga tgacaagccc aactcagatc gtccacccccc agtccgccac ccctattaca    3780
gtgcaggaca cacatccaag tcccactaac cggtcaaaaa gaaatctgaa gatggagatc    3840
attctgaccc tgagccaggg actgaagaaa tactatggca agatcctgag gctgctgcag    3900
ctgaccctgg aggaagatac agagggactg ctggaatggt gtaaacggaa cctgggcctg    3960
gactgcgacg ataccttctt tcagaagaga atcgaggagt tcttcattac aggggaggga    4020
cactttaatg aagtgctgca gttccgcact ccaggcaccc tgtccacaac tgaatctaca    4080
cccgcagggc tgcctactgc cgagccattc aaatcctact tgccaagggg cttcctgagc    4140
atcgattccg ggtactatag cgccaagtgt tattccggca catccaactc tgggctgcag    4200
ctgatcaata ttactagaca cagcaccagg atcgtggaca cacctgggcc aaaaattaca    4260
aacctgaaga ctatcaactg cattaatctg aaagctagca tcttcaagga gcatcgcgag    4320
gtcgaaatta atgtgctgct gcctcaggtg gcagtcaacc tgtccaattg tcacgtggtc    4380
attaagtctc atgtctgcga ctacagtctg gacatcgatg gcgccgtgcg gctgcctcac    4440
atctaccatg agggagtctt tattccaggc acctacaaga tcgtgatcga caagaaaaac    4500
aagctgaatg atagatgtac actgttcact gactgcgtca tcaaagggag ggaggtgcgc    4560
aagggacagt ctgtcctgag acagtataaa actgaaatca ggattgggaa ggcttctacc    4620
ggaagtcgga gactgctgag tgaggaacca tcagacgatt gcattagccg cacccagctg    4680
ctgcgaacag agactgccga aatccacgga gataactacg gaggcccggg cgacaagatc    4740
accatttgta atggctctac aattgtggat cagcggctgg gaagtgagct gggctgctat    4800
```

```
actatcaaca gagtgaggtc cttcaaactg tgcgaaaact ctgctaccgg gaagaattgc    4860
gagattgact ccgtgcccgt caaatgtcga cagggatact gcctgcgaat cacccaggag    4920
ggaagaggac acgtgaagct gtcaagaggc agcgaggtgg tcctggacgc ctgtgatacc    4980
tcttgcgaaa tcatgattcc taaaggaaca ggcgacatcc tggtggattg cagcggggga    5040
cagcagcact ttctgaagga caacctgatc gatctggggt gtccaaaaat tcccctgctg    5100
ggaaagatgg ctatctacat ttgcaggatg agtaatcatc ccaaaaccac aatggcattc    5160
ctgttttggt tctcatttgg ctacgtgatc acctgcatcc tgtgcaaagc catcttctat    5220
ctgctgatca ttgtgggaac actgggcaaa cggctgaagc agtatagaga actgaagccc    5280
cagacctgca caatctgtga gactacccct gtgaacgcca ttgacgctga aatgcacgat    5340
ctgaactgta gctacaatat ttgcccctat tgtgcaagcc gactgacctc cgacggactg    5400
gcacgacatg tcatccagtg ccctaagcgg aaagagaagg tggaggaaac agaactgtac    5460
ctgaatctgg agaggattcc atgggtggtc cgcaaactgc tgcaggtgag tgagtcaaca    5520
ggcgtcgccc tgaagaggtc ctcttggctg atcgtcctgc tggtgctgtt tactgtcagc    5580
ctgtccccag tgcagtccgc tccaatcgga cagggaaaaa caattgaagc ataccgcgcc    5640
cgagagggt atacttctat ctgtctgttt gtgctgggat caatcctgtt cattgtcagc    5700
tgcctgatga agggcctggt cgattctgtg gggaacagtt tctttcccgg actgtccatt    5760
tgcaaaacct gttctatcag ttcaattaat ggctttgaga tcgaaagtca caagtgctac    5820
tgttcactgt tctgctgtcc ttattgccgc cattgttcca cagacaaaga gatccacaag    5880
ctgcatctgt caatttgcaa gaaaaggaag aaagggagca acgtcatgct ggccgtgtgc    5940
aagctgatgt gcttccgcgc caccatggag gtgagtaaca gggctctgtt tatccgctca    6000
atcattaata ccaccttcgt gctgtgcatc ctgattctgg cagtctgcgt ggtctctacc    6060
agtgccgtgg agatggaaaa tctgcccgct ggcacatggg agcgggagga agatctgact    6120
aacttttgtc accaggaatg ccaagtgact gagaccgaat gcctgtgccc ttacgaggca    6180
ctggtgctga gaaaaccact gttcctggac agcaccgcca aaggcatgaa gaacctgctg    6240
aacagcacca gcctggaaac atccctgtct atcgaggctc cctgggggc aattaacgtc    6300
cagagtacct ataagcctac cgtgtcaaca gctaatatcg cactgagctg gagctccgtc    6360
gagcacagag ggaacaaaat cctggtgagt ggaaggagtg aatcaattat gaagctggag    6420
gaaagaaccg gcatctcttg ggacctgggg gtggaggatg ctagcgaatc caagctgctg    6480
acagtgagcg tcatggacct gtcacagatg tacagccccg tctttgagta tctgtccggc    6540
gatcgacaag tgggagaatg gcccaaagcc acatgtactg gcgactgccc tgagagatgc    6600
gggtgtactt ctagtacctg tctgcacaag gaatggccac attcccgaaa ctggcggtgt    6660
aatccaacct ggtgctgggg agtggggaca ggatgcactt gctgtggcct ggacgtgaaa    6720
gatctgttta cagattacat gttcgtcaaa tggaaggtgg agtatatcaa dacagaagca    6780
atcgtgtgcg tggagctgac tagccaggaa cgccagtgct ccctgattga ggccggaacc    6840
cgattcaatc tgggccccgt gaccatcaca ctgagcgagc ctcgaaacat tcagcagaag    6900
ctgccacccg aaatcattac actgcaccca agaatcgagg aaggcttctt tgacctgatg    6960
catgtccaga aagtgctgtc tgccagtacc gtgtgcaagc tgcagagctg cacacacggg    7020
gtgcccggag atctgcaggt ctaccatatc ggaaacctgc tgaaaggcga caaagtgaat    7080
gggcacctga tccataagat tgagccccac tttaatacct cctggatgtc ttgggatggc    7140
tgtgacctgg attactattg caacatgggc gactggcctt cctgcactta caccggggtc    7200
```

```
acacagcaca atcatgcatc tttcgtgaac ctgctgaata tcgagaccga ttacacaaag   7260
aacttccact tccatagcaa gagggtgact gcacacgggg acaccccaca gctggatctg   7320
aaagctcgac caacctacgg agcaggagag atcacagtgc tggtcgaggt ggctgacatg   7380
gaactgcata ctaagaaaat cgaaatttct ggactgaagt tcgccagtct ggcttgcacc   7440
ggatgttatg catgctcaag cggcatcagc tgcaaagtcc ggattcacgt ggacgagcca   7500
gatgaactga ccgtccatgt gaagtccgac gatcccgatg tggtcgccgc ttcctctagt   7560
ctgatggcca ggaagctgga gtttggcact gactcaacct tcaaagcctt cagcgccatg   7620
cctaagacct ccctgtgctt ctacatcgtg gagcgcgaac actgtaaatc atgcagcgag   7680
gaagatacta agaaatgcgt gaacaccaag ctggaacagc cacagtccat cctgattgag   7740
cataaaggga ccatcattgg aaagcagaac agcacatgta ctgctaaggc atcttgctgg   7800
ctggagagtg tgaaatcatt cttttatggc ctgaagaaca tgctgagcgg catctttggg   7860
aacgtgttca tggggatttt cctgtttctg gcccccttta tcctgctgat tctgttcttt   7920
atgttcggat ggagaatcct gttctgcttt aaatgctgta ggcgcacacg aggcctgttc   7980
aaataccggc acctgaagga cgatgaggaa actggatatc gacggatcat tgagaagctg   8040
aacaataaga aaggcaaaaa caagctgctg gacggggaaa gactggctga tagaagaatc   8100
gcagaactgt ttagcaccaa gacccacatc gggcagtcta gccagattct tcatgtttgg   8160
accaaatcaa cttgtgatac catgctcaaa gaggcctcaa ttatatttga gtttttaatt   8220
tttatgaaaa aaactaacag caatcatgga agtccacgat tttgagaccg acagttcaa   8280 tgatttcaat gaagatgact atgccacaag agaattcctg aatcccgatg agcgcatgac   8340
gtacttgaat catgctgatt acaacctgaa ttctcctcta attagtgatg atattgacaa   8400
tttaatcagg aaattcaatt ctcttccaat tccctcgatg tgggatagta agaactggga   8460
tggagttctt gagatgttaa catcatgtca agccaatccc atctcaacat ctcagatgca   8520
taaatggatg ggaagttggt taatgtctga taatcatgat gccagtcaag ggtatagttt   8580
tttacatgaa gtggacaaag aggcagaaat aacatttgac gtggtggaga ccttcatccg   8640
cggctggggc aacaaaccaa ttgaatacat caaaaaggaa agatggactg actcattcaa   8700
aattctcgct tatttgtgtc aaaagttttt ggacttacac aagttgacat taatcttaaa   8760
tgctgtctct gaggtggaat tgctcaactt ggcgaggact ttcaaaggca agtcagaag   8820 aagttctcat ggaacgaaca tatgcaggat tagggttccc agcttgggtc ctactttat   8880 ttcagaagga tgggcttact tcaagaaact tgatattcta atggaccgaa actttctgtt   8940
aatggtcaaa gatgtgatta tagggaggat gcaaacggtg ctatccatgg tatgtagaat   9000
agacaacctg ttctcagagc aagacatctt ctcccttcta aatatctaca gaattggaga   9060
taaaattgtg gagaggcagg gaaattttc ttatgacttg attaaaatgg tggaaccgat   9120
atgcaacttg aagctgatga aattagcaag agaatcaagg cctttagtcc cacaattccc   9180
tcattttgaa aatcatatca agacttctgt tgatgaaggg gcaaaaattg accgaggtat   9240
aagattcctc catgatcaga taatgagtgt gaaaacagtg gatctcacac tggtgattta   9300
tggatcgttc agacattggg gtcatccttt tatagattat tacactggac tagaaaaatt   9360
acattcccaa gtaaccatga agaaagatat tgatgtgtca tatgcaaaag cacttgcaag   9420
tgatttagct cggattgttc tatttcaaca gttcaatgat cataaaaagt ggttcgtgaa   9480
tggagacttg ctccctcatg atcatccctt taaaagtcat gttaaagaaa atacatggcc   9540
```

```
cacagctgct caagttcaag attttggaga taaatggcat gaacttccgc tgattaaatg   9600
ttttgaaata cccgacttac tagacccatc gataatatac tctgacaaaa gtcattcaat   9660
gaataggtca gaggtgttga aacatgtccg aatgaatccg aacactccta tccctagtaa   9720
aaaggtgttg cagactatgt tggacacaaa ggctaccaat tggaaagaat tcttaaaga    9780 gattgatgag aagggcttag atgatgatga tctaattatt ggtcttaaag gaaaggagag   9840
ggaactgaag ttggcaggta gattttttctc cctaatgtct tggaaattgc gagaatactt  9900
tgtaattacc gaatatttga taaagactca tttcgtccct atgtttaaag gcctgacaat   9960
ggcggacgat ctaactgcag tcattaaaaa gatgttagat tcctcatccg gccaaggatt  10020
gaagtcatat gaggcaattt gcatagccaa tcacattgat tacgaaaaat ggaataacca  10080
ccaaaggaag ttatcaaacg gcccagtgtt ccgagttatg ggccagttct taggttatcc  10140
atccttaatc gagagaactc atgaattttt tgagaaaagt cttatatact acaatggaag  10200
accagacttg atgcgtgttc acaacaacac actgatcaat tcaacctccc aacgagtttg  10260
ttggcaagga caagagggtg gactggaagg tctacggcaa aaaggatgga gtatcctcaa  10320
tctactggtt attcaaagag aggctaaaat cagaaacact gctgtcaaag tcttggcaca  10380
aggtgataat caagttattt gcacacagta taaaacgaag aaatcgagaa acgttgtaga  10440
attacagggt gctctcaatc aaatggtttc taataatgag aaaattatga ctgcaatcaa  10500 aataggggaca gggaagttag acttttgat aaatgacgat gagactatgc aatctgcaga  10560
ttacttgaat tatggaaaaa taccgatttt ccgtggagtg attagagggt tagagaccaa  10620
gagatggtca cgagtgactt gtgtcaccaa tgaccaaata cccacttgtg ctaatataat  10680
gagctcagtt tccacaaatg ctctcaccgt agctcatttt gctgagaacc caatcaatgc  10740
catgatacag tacaattatt ttgggacatt tgctagactc ttgttgatga tgcatgatcc  10800
tgctcttcgt caatcattgt atgaagttca agataagata ccgggcttgc acagttctac  10860
tttcaaatac gccatgttgt atttggaccc ttccattgga ggagtgtcgg gcatgtcttt  10920
gtccaggttt ttgattagag ccttcccaga tcccgtaaca gaaagtctct cattctggag  10980
attcatccat gtacatgctc gaagtgagca tctgaaggag atgagtgcag tatttggaaa  11040
ccccgagata gccaagtttc gaataactca catagacaag ctagtagaag atccaacctc  11100
tctgaacatc gctatgggaa tgagtccagc gaacttgtta aagactgagg ttaaaaatg   11160 cttaatcgaa tcaagacaaa ccatcaggaa ccaggtgatt aaggatgcaa ccatatattt  11220
gtatcatgaa gaggatcggc tcagaagttt cttatggtca ataaatcctc tgttccctag  11280
atttttaagt gaattcaaat caggcacttt ttgggagtc gcagacgggc tcatcagtct  11340 attcaaaat tctcgtacta ttcggaactc ctttaagaaa aagtatcata ggaattgga   11400 tgatttgatt gtgaggagtg aggtatcctc ttttgacacat ttagggaaac ttcatttgag  11460
aaggggatca tgtaaaatgt ggacatgttc agctactcat gctgacacat taagatacaa  11520
atcctggggc cgtacagtta ttgggacaac tgtaccccat ccattagaaa tgttgggtcc  11580
acaacatcga aaagagactc cttgtgcacc atgtaacaca tcagggttca attatgtttc  11640
tgtgcattgt ccagacggga tccatgacgt ctttagttca cggggaccat tgcctgctta  11700
tctagggtct aaaacatctg aatctacatc tattttgcag ccttgggaaa gggaaagcaa  11760
agtcccactg attaaaagag ctacacgtct tagagatgct atctcttggt tgttgaacc   11820 cgactctaaa ctagcaatga ctatacttc taacatccac tctttaacag gcgaagaatg  11880
gaccaaaagg cagcatgggt tcaaaagaac agggtctgcc cttcataggt tttcgacatc  11940
```

```
tcggatgagc catggtgggt tcgcatctca gagcactgca gcattgacca ggttgatggc    12000
aactacagac accatgaggg atctgggaga tcagaatttc gactttttat tccaagcaac    12060
gttgctctat gctcaaatta ccaccactgt tgcaagagac ggatggatca ccagttgtac    12120
agatcattat catattgcct gtaagtcctg tttgagaccc atagaagaga tcaccctgga    12180
ctcaagtatg gactacacgc ccccagatgt atcccatgtg ctgaagacat ggaggaatgg    12240
ggaaggttcg tggggacaag agataaaaca gatctatcct ttagaaggga attggaagaa    12300
tttagcacct gctgagcaat cctatcaagt cggcagatgt ataggttttc tatatggaga    12360
cttggcgtat agaaaatcta ctcatgccga ggacagttct ctatttcctc tatctataca    12420
aggtcgtatt agaggtcgag gtttcttaaa agggttgcta gacggattaa tgagagcaag    12480
ttgctgccaa gtaatacacc ggagaagtct ggctcatttg aagaggccgg ccaacgcagt    12540
gtacggaggt ttgatttact tgattgataa attgagtgta tcacctccat tcctttctct    12600
tactagatca ggacctatta gagacgaatt agaaacgatt ccccacaaga tcccaacctc    12660
ctatccgaca agcaaccgtg atatgggggt gattgtcaga aattacttca ataccaatg    12720
ccgtctaatt gaaaagggaa aatacagatc acattattca caattatggt tattctcaga    12780
tgtcttatcc atagacttca ttggaccatt ctctatttcc accaccctct tgcaaatcct    12840
atacaagcca tttttatctg ggaaagataa gaatgagttg agagagctgg caaatctttc    12900
ttcattgcta agatcaggag aggggtggga agacatacat gtgaaattct tcaccaagga    12960
catattattg tgtccagagg aaatcagaca tgcttgcaag ttcgggattg ctaaggataa    13020
taataaagac atgagctatc ccccttgggg aagggaatcc agagggacaa ttacaacaat    13080
ccctgtttat tatacgacca ccccttaccc aaagatgcta gagatgcctc caagaatcca    13140
aaatcccctg ctgtccggaa tcaggttggg ccaattacca actggcgctc attataaaat    13200
tcggagtata ttcatgggaa tgggaatcca ttacagggac ttcttgagtt gtggagacgg    13260
ctccggaggg atgactgctg cattactacg agaaaatgtg catagcagag gaatattcaa    13320
tagtctgtta gaattatcag ggtcagtcat gcgaggcgcc tctcctgagc ccccagtgc    13380
cctagaaact ttaggaggag ataaatcgag atgtgtaaat ggtgaaacat gttgggaata    13440
tccatctgac ttatgtgacc caaggacttg ggactatttc ctccgactca agcaggctt    13500
ggggcttcaa attgatttaa ttgtaatgga tatggaagtt cgggattctt ctactagcct    13560
gaaaattgag acgaatgtta gaaattatgt gcaccggatt ttggatgagc aaggagttt    13620
aatctacaag acttatggaa catatatttg tgagagcgaa aagaatgcag taacaatcct    13680
tggtcccatg ttcaagacgg tcgacttagt tcaaacagaa tttagtagtt ctcaaacgtc    13740
tgaagtatat atggtatgta aaggtttgaa gaaattaatc gatgaaccca atcccgattg    13800
gtcttccatc aatgaatcct ggaaaaacct gtacgcattc cagtcatcag aacaggaatt    13860
tgccagagca aagaaggtta gtacatactt taccttgaca ggtattccct cccaattcat    13920
tcctgatcct tttgtaaaca ttgagactat gctacaaata ttcggagtac ccacgggtgt    13980
gtctcatgcg gctgccttaa aatcatctga tagacctgca gatttattga ccattagcct    14040
ttttatatg gcgattatat cgtattataa catcaatcat atcagagtag gaccgatacc    14100
tccgaacccc ccatcagatg gaattgcaca aaatgtgggg atcgctataa ctggtataag    14160
cttttggctg agtttgatgg agaaagacat tccactatat caacagtgtt tagcagttat    14220
ccagcaatca ttcccgatta ggtgggaggc tgtttcagta aaaggaggat acaagcagaa    14280
```

| | |
|---|---:|
| gtggagtact agaggtgatg ggctcccaaa agatacccga atttcagact ccttggcccc | 14340 |
| aatcgggaac tggatcagat ctctggaatt ggtccgaaac caagttcgtc taaatccatt | 14400 |
| caatgagatc ttgttcaatc agctatgtcg tacagtggat aatcatttga aatggtcaaa | 14460 |
| tttgcgaaga aacacaggaa tgattgaatg gatcaataga cgaatttcaa agaagaccg | 14520 |
| gtctatactg atgttgaaga gtgacctaca cgaggaaaac tcttggagag attaaaaaat | 14580 |
| catgaggaga ctccaaactt taagtatgaa aaaaactttg atccttaaga ccctcttgtg | 14640 |
| gttttattt tttatctggt tttgtggtct tcgtgggtcg gcatggcatc tccacctcct | 14700 |
| cgcggtccga cctgggcatc cgaaggagga cgtcgtccac tcggatggct aagggagggg | 14760 |
| cccccgcggg gctgctaaca aagcccgaaa ggaagctgag ttggctgctg ccaccgctga | 14820 |
| gcaataacta gcataacccc ttggggcctc taaacgggtc ttgaggggtt ttttgctgaa | 14880 |
| aggaggaact atatccggat cgagacctcg atactagtga gctcc | 14925 |

<210> SEQ ID NO 2
<211> LENGTH: 5055
<212> TYPE: DNA
<213> ORGANISM: Artificial Sequence
<220> FEATURE:
<223> OTHER INFORMATION: Recombinant DNA

<400> SEQUENCE: 2

| | |
|---|---:|
| atgcatatct cactgatgta cgctatcctg tgcctgcagc tgtgcggcct gggggaaact | 60 |
| cacggaagcc ataacgaaac tcgccataac aagaccgaca caatgaccac acctggcgat | 120 |
| aacccaagct ccgagccccc tgtgagcact gccctgtcca ttaccctgga tccttctact | 180 |
| gtgaccccaa ctacccctgc ttccggactg gagggatctg agaagtgta caccagccca | 240 |
| cccatcacaa ctggatctct gccactgagt gagaccacac cagaactgcc cgtgactacc | 300 |
| gggacagaca ctctgtctgc cggagacgtg gatccaagta cccagacagc aggagggacc | 360 |
| tcagctccaa ccgtgaggac aagcctgcct aactcaccaa gcactccctc cacccctcag | 420 |
| gatactcacc atcctgtccg caatctgctg tccgtgacct ctcctggccc agacgaaact | 480 |
| agtaccccat caggaacagg caaggagtct agtgccactt caagccccca ccccgtgagc | 540 |
| aataggcctc caacacccc tgcaactgcc cagggaccta ctgagaacga ttctcacaat | 600 |
| gctaccgagc atccagaatc actgacccag agcgcaacac ctggcctgat gacaagccca | 660 |
| actcagatcg tccaccccca gtccgccacc cctattacag tgcaggacac acatccaagt | 720 |
| cccactaacc ggtcaaaaag aaatctgaag atggagatca ttctgaccct gagccaggga | 780 |
| ctgaagaaat actatggcaa gatcctgagg ctgctgcagc tgaccctgga ggaagataca | 840 |
| gagggactgc tggaatggtg taaacggaac ctgggcctgg actgcacga taccttcttt | 900 |
| cagaagagaa tcgaggagtt cttcattaca ggggagggac actttaatga agtgctgcag | 960 |
| ttccgcactc caggcaccct gtccacaact gaatctacac ccgcagggct gcctactgcc | 1020 |
| gagccattca atcctactt tgccaagggc ttcctgagca tcgattccgg gtactatagc | 1080 |
| gccaagtgtt attccggcac ttccaactct gggctgcagc tgatcaatat tactagacac | 1140 |
| agcaccagga tcgtggacac acctgggcca aaaattacaa acctgaagac tatcaactgc | 1200 |
| attaatctga agctagcat cttcaaggag catcgcgagg tcgaaattaa tgtgctgctg | 1260 |
| cctcaggtgg cagtcaacct gtccaattgt cacgtggtca ttaagtctca tgtctgcgac | 1320 |
| tacagtctgg acatcgatgg cgccgtgcgg ctgcctcaca tctaccatga gggagtcttt | 1380 |
| attccaggca cctacaagat cgtgatcgac aagaaaaaca agctgaatga tagatgtaca | 1440 |

```
ctgttcactg actgcgtcat caaagggagg gaggtgcgca agggacagtc tgtcctgaga    1500
cagtataaaa ctgaaatcag gattgggaag gcttctaccg gaagtcggag actgctgagt   1560
gaggaaccat cagacgattg cattagccgc acccagctgc tgcgaacaga gactgccgaa   1620
atccacggag ataactacgg aggccccggc gacaagatca ccatttgtaa tggctctaca   1680
attgtggatc agcggctggg aagtgagctg ggctgctata ctatcaacag agtgaggtcc   1740
ttcaaactgt gcgaaaactc tgctaccggg aagaattgcg agattgactc cgtgcccgtc   1800
aaatgtcgac agggatactg cctgcgaatc acccaggagg aagaggaca cgtgaagctg    1860 tcaagaggca gcgaggtggt cctggacgcc tgtgatacct cttgcgaaat catgattcct   1920
aaaggaacag gcgacatcct ggtggattgc agcgggggac agcagcactt tctgaaggac   1980
aacctgatcg atctggggtg tccaaaaatt cccctgctgg gaaagatggc tatctacatt   2040
tgcaggatga gtaatcatcc caaaaccaca atggcattcc tgttttggtt ctcatttggc   2100
tacgtgatca cctgcatcct gtgcaaagcc atcttctatc tgctgatcat tgtgggaaca   2160
ctgggcaaac ggctgaagca gtatagagaa ctgaagcccc agacctgcac aatctgtgag   2220
actacccctg tgaacgccat tgacgctgaa atgcacgatc tgaactgtag ctacaatatt   2280
tgcccctatt gtgcaagccg actgacctcc gacggactgg cacgacatgt catccagtgc   2340
cctaagcgga aagagaaggt ggaggaaaca gaactgtacc tgaatctgga gaggattcca   2400
tgggtggtcc gcaaactgct gcaggtgagt gagtcaacag gcgtcgccct gaagaggtcc   2460
tcttggctga tcgtcctgct ggtgctgttt actgtcagcc tgtccccagt gcagtccgct   2520
ccaatcggac agggaaaaac aattgaagca taccgcgccc gagaggggta tacttctatc   2580
tgtctgtttg tgctgggatc aatcctgttc attgtcagct gcctgatgaa gggcctggtc   2640
gattctgtgg ggaacagttt cttttcccgga ctgtccattt gcaaaacctg ttctatcagt   2700
tcaattaatg gctttgagat cgaaagtcac aagtgctact gttcactgtt ctgctgtcct   2760
tattgccgcc attgttccac agacaaagag atccacaagc tgcatctgtc aatttgcaag   2820
aaaaggaaga aagggagcaa cgtcatgctg gccgtgtgca agctgatgtg cttccgcgcc   2880
accatggagg tgagtaacag ggctctgttt atccgctcaa tcattaatac caccttcgtg   2940
ctgtgcatcc tgattctggc agtctgcgtg gtctctacca gtgccgtgga gatggaaaat   3000
ctgcccgctg gcacatggga gcgggaggaa gatctgacta cttttgtca ccaggaatgc    3060 caagtgactg agaccgaatg cctgtgccct tacgaggcac tggtgctgag aaaaccactg   3120
ttcctggaca gcaccgccaa aggcatgaag aacctgctga acagcaccag cctggaaaca   3180
tccctgtcta tcgaggctcc ctgggggggca attaacgtcc agagtaccta taagcctacc    3240
gtgtcaacag ctaatatcgc actgagctgg agctccgtcg agcacagagg gaacaaaatc   3300
ctggtgagtg gaaggagtga atcaattatg aagctggagg aaagaaccgg catctcttgg   3360
gacctggggg tggaggatgc tagcgaatcc aagctgctga cagtgagcgt catggacctg   3420
tcacagatgt acagccccgt ctttgagtat ctgtccggcg atcgacaagt gggagaatgg   3480
cccaaagcca catgtactgg cgactgcccc gagagatgcg ggtgtacttc tagtacctgt   3540
ctgcacaagg aatggccaca ttcccgaaac tggcggtgta atccaacctg gtgctgggga   3600
gtggggacag gatgcacttg ctgtggcctg gacgtgaaag atctgtttac agattacatg   3660
ttcgtcaaat ggaaggtgga gtatatcaag acagaagcaa tcgtgtgcgt ggagctgact   3720
agccaggaac gccagtgctc cctgattgag gccggaaccc gattcaatct gggccccgtg   3780
```

```
accatcacac tgagcgagcc tcgaaacatt cagcagaagc tgccacccga aatcattaca    3840
ctgcacccaa gaatcgagga aggcttcttt gacctgatgc atgtccagaa agtgctgtct    3900
gccagtaccg tgtgcaagct gcagagctgc acacacgggg tgcccggaga tctgcaggtc    3960
taccatatcg gaaacctgct gaaaggcgac aaagtgaatg gcacctgat ccataagatt     4020 gagcccact ttaatacctc ctggatgtct tgggatggct gtgacctgga ttactattgc     4080
aacatgggcg actggccttc ctgcacttac accggggtca cacagcacaa tcatgcatct    4140
ttcgtgaacc tgctgaatat cgagaccgat tacacaaaga acttccactt ccatagcaag    4200
agggtgactg cacacgggga cacccacag ctggatctga aagctcgacc aacctacgga    4260
gcaggagaga tcacagtgct ggtcgaggtg gctgacatgg aactgcatac taagaaaatc    4320
gaaatttctg gactgaagtt cgccagtctg gcttgcaccg gatgttatgc atgctcaagc   4380
ggcatcagct gcaaagtccg gattcacgtg gacgagccag atgaactgac cgtccatgtg    4440
aagtccgacg atcccgatgt ggtcgccgct tcctctagtc tgatggccag gaagctggag    4500
tttggcactg actcaacctt caaagccttc agcgccatgc taagacctc cctgtgcttc     4560 tacatcgtgg agcgcgaaca ctgtaaatca tgcagcgagg aagatactaa gaatgcgtg     4620 aacaccaagc tggaacagcc acagtccatc ctgattgagc ataaagggac catcattgga    4680
aagcagaaca gcacatgtac tgctaaggca tcttgctggc tggagagtgt gaaatcattc    4740
ttttatggcc tgaagaacat gctgagcggc atctttggga acgtgttcat ggggattttc    4800
ctgtttctgg cccccttttat cctgctgatt ctgttcttta tgttcggatg gagaatcctg   4860
ttctgcttta aatgctgtag gcgcacacga ggcctgttca ataccggca cctgaaggac    4920 gatgaggaaa ctggatatcg acggatcatt gagaagctga acaataagaa aggcaaaaac    4980
aagctgctgg acggggaaag actggctgat agaagaatcg cagaactgtt tagcaccaag    5040
acccacatcg ggtag                                                     5055

<210> SEQ ID NO 3
<211> LENGTH: 14925
<212> TYPE: DNA
<213> ORGANISM: Artificial Sequence
<220> FEATURE:
<223> OTHER INFORMATION: Recombinant DNA

<400> SEQUENCE: 3
gacgaagaca aacaaaccat tattatcatt aaaaggctca ggagaaactt taacagtaat      60
caaaatgtct gttacagtca agagaatcat tgacaacaca gtcgtagttc caaaacttcc    120
tgcaaatgag gatccagtgg aatacccggc agattacttc agaaaatcaa aggagattcc    180
tctttacatc aatactacaa aaagtttgtc agatctaaga ggatatgtct accaaggcct    240
caaatccgga aatgtatcaa tcatacatgt caacagctac ttgtatggag cattaaagga    300
catccggggt aagttggata agattggtc aagtttcgga ataaacatcg ggaaagcagg    360
ggatacaatc ggaatatttg accttgtatc cttgaaagcc ctggacggcg tacttccaga    420
tggagtatcg gatgcttcca gaaccagcgc agatgacaaa tggttgcctt tgtatctact    480
tggcttatac agagtgggca gaacacaaat gcctgaatac agaaaaaagc tcatggatgg    540
gctgacaaat caatgcaaaa tgatcaatga acagtttgaa cctcttgtgc agaaggtcg    600 tgacattttt gatgtgtggg gaatgacag taattacaca aaaattgtcg ctgcagtgga    660
catgttcttc cacatgttca aaaaacatga atgtgcctcg ttcagatacg gaactattgt    720
ttccagattc aaagattgtg ctgcattggc aacatttgga cacctctgca aaataaccgg    780
```

```
aatgtctaca gaagatgtaa cgacctggat cttgaaccga aagttgcag atgaaatggt      840
ccaaatgatg cttccaggcc aagaaattga caaggccgat tcatacatgc cttatttgat      900
cgactttgga ttgtcttcta agtctccata ttcttccgtc aaaaaccctg ccttccactt      960
ctgggggcaa ttgacagctc ttctgctcag atccaccaga gcaaggaatg cccgacagcc     1020
tgatgacatt gagtatacat ctcttactac agcaggtttg ttgtacgctt atgcagtagg     1080
atcctctgcc gacttggcac aacagttttg tgttggagat aacaaataca ctccagatga     1140
tagtaccgga ggattgacga ctaatgcacc gccacaaggc agagatgtgg tcgaatggct     1200
cggatggttt gaagatcaaa acagaaaacc gactcctgat atgatgcagt atgcgaaaag     1260
agcagtcatg tcactgcaag gcctaagaga aagacaatt ggcaagtatg ctaagtcaga      1320
atttgacaaa tgaccctata attctcagat cacctattat atattatgct acatatgaaa     1380
aaaactaaca gatatcatgg ataatctcac aaaagttcgt gagtatctca agtcctattc     1440
tcgtctggat caggcggtag gagagataga tgagatcgaa gcacaacgag ctgaaaagtc     1500
caattatgag ttgttccaag aggatggagt ggaagagcat actaagccct cttattttca     1560
ggcagcagat gattctgaca cagaatctga accagaaatt gaagacaatc aaggcttgta     1620
tgcaccagat ccagaagctg agcaagttga aggctttata caggggcctt tagatgacta     1680
tgcagatgag aagtggatg ttgtatttac ttcggactgg aaacagcctg agcttgaatc      1740
tgacgagcat ggaaagacct acggttgac atcgccagag ggtttaagtg agagcagaa       1800
atcccagtgg ctttcgacga ttaaagcagt cgtgcaaagt gccaaatact ggaatctggc     1860
agagtgcaca tttgaagcat cgggagaagg ggtcattatg aaggagcgcc agataactcc     1920
ggatgtatat aaggtcactc cagtgatgaa cacacatccg tcccaatcag aagcagtatc     1980
agatgtttgg tctctctcaa agacatccat gactttccaa cccaagaaag caagtcttca     2040
gcctctcacc atatccttgg atgaattgtt ctcatctaga ggagagttca tctctgtcgg     2100
aggtgacgga cgaatgtctc ataaagaggc catcctgctc ggcctgagat acaaaaagtt     2160
gtacaatcag gcgagagtca aatattctct gtagactatg aaaaaaagta acagatatca     2220
cgatctaagt gttatcccaa tccattcatc atgagttcct taaagaagat tctcggtctg     2280
aaggggaaag gtaagaaatc taagaaatta gggatcgcac caccccctta tgaagaggac     2340
actagcatgg agtatgctcc gagcgctcca attgacaaat cctatttggg agttgacgag     2400
atggacacct atgatccgaa tcaattaaga tatgagaaat tcttctttac agtgaaaatg     2460
acggttagat ctaatcgtcc gttcagaaca tactcagatg tggcagccgc tgtatcccat     2520
tgggatcaca tgtacatcgg aatggcaggg aaacgtccct tctacaaaat cttggctttt     2580
ttgggttctt ctaatctaaa ggccactcca gcggtattgg cagatcaagg tcaaccagag     2640
tatcacgctc actgcgaagg cagggcttat ttgccacata ggatgggaa gaccccctccc      2700
atgctcaatg taccagagca cttcagaaga ccattcaata taggtcttta caagggaacg     2760
attgagctca caatgaccat ctacgatgat gagtcactgg aagcagctcc tatgatctgg     2820
gatcatttca attcttccaa attttctgat ttcagagaga aggccttaat gtttggcctg     2880
attgtcgaga aaaaggcatc tggagcgtgg gtcctggact ctatcggcca cttcaaatga     2940
gctagtctaa cttctagctt ctgaacaatc cccggtttac tcagtctccc ctaattccag     3000
cctctcgaac aactaatatc ctgtcttttc tatccctatg aaaaaaacta acagagatcg     3060
atctgtttac gcgttttcat catgcatatc tcactgatgt acgctatcct gtgcctgcag     3120
```

-continued

```
ctgtgcggcc tggggggaaac tcacggaagc cataacgaaa ctcgccataa caagaccgac  3180
acaatgacca cacctggcga taacccaagc tccgagcccc ctgtgagcac tgccctgtcc  3240
attaccctgg atccttctac tgtgacccca actacccctg cttccggact ggagggatct  3300
ggagaagtgt acaccagccc acccatcaca actggatctc tgccactgag tgagaccaca  3360
ccagaactgc ccgtgactac cgggacagac actctgtctg ccggagacgt ggatccaagt  3420
acccagacag caggagggac ctcagctcca accgtgagga caagcctgcc taactcacca  3480
agcactccct ccacccctca ggatactcac catcctgtcc gcaatctgct gtccgtgacc  3540
tctcctggcc cagacgaaac tagtacccca tcaggaacag gcaaggagtc tagtgccact  3600
tcaagccccc accccgtgag caataggcct ccaacacccc ctgcaactgc ccagggacct  3660
actgagaacg attctcacaa tgctaccgag catccagaat cactgaccca gagcgcaaca  3720
cctggcctga tgacaagccc aactcagatc gtccacccccc agtccgccac ccctattaca  3780
gtgcaggaca cacatccaag tcccactaac cggtcaaaaa gaaatctgaa gatggagatc  3840
attctgaccc tgagccaggg actgaagaaa tactatggca gatcctgag gctgctgcag  3900
ctgaccctgg aggaagatac agagggactg ctggaatggt gtaaacggaa cctgggcctg  3960
gactgcgacg atacccttctt tcagaagaga tcgaggagt tcttcattac aggggaggga  4020
cactttaatg aagtgctgca gttccgcact ccaggcaccc tgtccacaac tgaatctaca  4080
cccgcagggc tgcctactgc cgagccattc aaatcctact tgccaaggg cttcctgagc  4140
atcgattccg ggtactatag cgccaagtgt tattccggca catccaactc tgggctgcag  4200
ctgatcaata ttactagaca cagcaccagg atcgtggaca cacctgggcc aaaaattaca  4260
aacctgaaga ctatcaactg cattaatctg aaagctagca tcttcaagga gcatcgcgag  4320
gtcgaaatta atgtgctgct gcctcaggtg gcagtcaacc tgtccaattg tcacgtggtc  4380
attaagtctc atgtctgcga ctacagtctg gacatcgatg gcgccgtgcg gctgcctcac  4440
atctaccatg agggagtctt tattccaggc acctacaaga tcgtgatcga caagaaaaac  4500
aagctgaatg atagatgtac actgttcact gactgcgtca tcaaagggag ggaggtgcgc  4560
aagggacagt ctgtcctgag acagtataaa actgaaatca ggattgggaa ggcttctacc  4620
ggaagtcgga gactgctgag tgaggaacca tcagacgatt gcattagccg cacccagctg  4680
ctgcgaacag agactgccga aatccacgga gataactacg gaggcccgg cgacaagatc  4740
accatttgta atggctctac aattgtggat cagcggctgg gaagtgagct gggctgctat  4800
actatcaaca gagtgaggtc cttcaaactg tgcgaaaact ctgctaccgg gaagaattgc  4860
gagattgact ccgtgcccgt caaatgtcga cagggatact gcctgcgaat cacccaggag  4920
ggaagaggac acgtgaagct gtcaagaggc agcgaggtgg tcctgacgc ctgtgatacc  4980
tcttgcgaaa tcatgattcc taaaggaaca ggcgacatcc tggtggattg cagcggggga  5040
cagcagcact ttctgaagga caacctgatc gatctgggt gtccaaaaat tcccctgctg  5100
ggaaagatgg ctatctacat ttgcaggatg agtaatcatc ccaaaaccac aatggcattc  5160
ctgttttggt tctcatttgg ctacgtgatc acctgcatcc tgtgcaaagc catcttctat  5220
ctgctgatca ttgtgggaac actgggcaaa cggctgaagc agtatagaga actgaagccc  5280
cagacctgca caatctgtga gactacccct gtgaacgcca ttgacgctga aatgcacgat  5340
ctgaactgta gctacaatat ttgccccat tgtcaagcc gactgacctc cgacggactg  5400
gcacgacatg tcatccagtg ccctaagcgg aaagagaagg tggaggaaac agaactgtac  5460
ctgaatctgg agaggattcc atgggtggtc cgcaaactgc tgcaggtgag tgagtcaaca  5520
```

```
ggcgtcgccc tgaagaggtc ctcttggctg atcgtcctgc tggtgctgtt tactgtcagc    5580
ctgtccccag tgcagtccgc tccaatcgga cagggaaaaa caattgaagc ataccgcgcc    5640
cgagagtggt atacttctat ctgtctgttt gtgctgggat caatcctgtt cattgtcagc    5700
tgcctgatga agggcctggt cgattctgtg gggaacagtt tctttcccgg actgtccatt    5760
tgcaaaacct gttctatcag ttcaattaat ggctttgaga tcgaaagtca caagtgctac    5820
tgttcactgt tctgctgtcc ttattgccgc cattgttcca cagacaaaga gatccacaag    5880
ctgcatctgt caatttgcaa gaaaaggaag aaagggagca acgtcatgct ggccgtgtgc    5940
aagctgatgt gcttccgcgc caccatggag gtgagtaaca gggctctgtt tatccgctca    6000
atcattaata ccaccttcgt gctgtgcatc ctgattctgg cagtctgcgt ggtctctacc    6060
agtgccgtgg agatggaaaa tctgcccgct ggcacatggg agcgggagga agatctgact    6120
aactttttgtc accaggaatg ccaagtgact gagaccgaat gcctgtgccc ttacgaggca    6180
ctggtgctga gaaaaccact gttcctggac agcaccgcca aaggcatgaa gaacctgctg    6240
aacagcacca gcctggaaac atccctgtct atcgaggctc cctgggggggc aattaacgtc    6300
cagagtacct ataagcctac cgtgtcaaca gctaatatcg cactgagctg gagctccgtc    6360
gagcacagag ggaacaaaat cctggtgagt ggaaggagtg aatcaattat gaagctggag    6420
gaaagaaccg gcatctcttg ggacctgggg gtggaggatg ctagcgaatc caagctgctg    6480
acagtgagcg tcatggacct gtcacagatg tacagccccg tctttgagta tctgtccggc    6540
gatcgacaag tggagaatg gcccaaagcc acatgtactg gcgactgccc tgagagatgc    6600
gggtgtactt ctagtacctg tctgcacaag gaatggccac attcccgaaa ctggcggtgt    6660
aatccaacct ggtgctgggg agtggggaca ggatgcactt gctgtggcct ggacgtgaaa    6720
gatctgttta cagattacat gttcgtcaaa tggaaggtgg agtatatcaa gacagaagca    6780
atcgtgtgcg tggagctgac tagccaggaa cgccagtgct ccctgattga ggccggaacc    6840
cgattcaatc tgggccccgt gaccatcaca ctgagcgagc ctcgaaacat tcagcagaag    6900
ctgcccaccc gaaatcattac actgcaccca agaatcgagg aaggcttctt tgacctgatg    6960
catgtccaga aagtgctgtc tgccagtacc gtgtgcaagc tgcagagctg cacacacggg    7020
gtgcccggag atctgcaggt ctaccatatc ggaaacctgc tgaaaggcga caaagtgaat    7080
gggcacctga tccataagat tgagcccac tttaatacct cctggatgtc ttgggatggc    7140
tgtgacctgg attactattg caacatgggc gactggcctt cctgcactta caccgggtgc    7200
acacagcaca atcatgcatc tttcgtgaac ctgctgaata tcgagaccga ttacacaaag    7260
aacttccact tccatagcaa gagggtgact gcacacgggg acaccccaca gctggatctg    7320
aaagctcgac caacctacgg agcaggagag atcacagtgc tggtcgaggt ggctgacatg    7380
gaactgcata ctaagaaaat cgaaatttct ggactgaagt tcgccagtct ggcttgcacc    7440
ggatgttatg catgctcaag cggcatcagc tgcaaagtcc ggattcacgt ggacgagcca    7500
gatgaactga ccgtccatgt gaagtccgac gatcccgatg tggtcgccgc ttcctctagt    7560
ctgatggcca ggaagctgga gtttggcact gactcaacct tcaaagcctt cagcgccatg    7620
cctaagacct ccctgtgctt ctacatcgtg gagcgcgaac actgtaaatc atgcagcgag    7680
gaagatacta agaaatgcgt gaacaccaag ctggaacagc cacagtccat cctgattgag    7740
cataaagga ccatcattgg aaagcagaac agcacatgta ctgctaaggc atcttgctgg    7800
ctggagagtg tgaaatcatt cttttatggc ctgaagaaca tgctgagcgg catctttggg    7860
```

-continued

| | |
|---|---|
| aacgtgttca tggggatttt cctgtttctg gccccctta tcctgctgat tctgttcttt | 7920 |
| atgttcggat ggagaatcct gttctgcttt aaatgctgta ggcgcacacg aggcctgttc | 7980 |
| aaataccggc acctgaagga cgatgaggaa actggatatc gacggatcat tgagaagctg | 8040 |
| aacaataaga aaggcaaaaa caagctgctg gacggggaaa gactggctga tagaagaatc | 8100 |
| gcagaactgt ttagcaccaa gacccacatc gggcagtcta gccagattct tcatgtttgg | 8160 |
| accaaatcaa cttgtgatac catgctcaaa gaggcctcaa ttatatttga gttttaatt | 8220 |
| tttatgaaaa aaactaacag caatcatgga agtccacgat tttgagaccg acgagttcaa | 8280 |
| tgatttcaat gaagatgact atgccacaag agaattcctg aatcccgatg agcgcatgac | 8340 |
| gtacttgaat catgctgatt acaacctgaa ttctcctcta attagtgatg atattgacaa | 8400 |
| tttaatcagg aaattcaatt ctcttccaat tccctcgatg tgggatagta agaactggga | 8460 |
| tggagttctt gagatgttaa catcatgtca agccaatccc atctcaacat ctcagatgca | 8520 |
| taaatggatg ggaagttggt taatgtctga taatcatgat gccagtcaag ggtatagttt | 8580 |
| tttacatgaa gtggacaaag aggcagaaat aacatttgac gtggtggaga ccttcatccg | 8640 |
| cggctggggc aacaaaccaa ttgaatacat caaaaaggaa agatggactg actcattcaa | 8700 |
| aattctcgct tatttgtgtc aaaagttttt ggacttacac aagttgacat taatcttaaa | 8760 |
| tgctgtctct gaggtggaat tgctcaactt ggcgaggact ttcaaaggca aagtcagaag | 8820 |
| aagttctcat ggaacgaaca tatgcaggat tagggttccc agcttgggtc ctactttat | 8880 |
| ttcagaagga tgggcttact tcaagaaact tgatattcta atggaccgaa actttctgtt | 8940 |
| aatggtcaaa gatgtgatta tagggaggat gcaaacggtg ctatccatgg tatgtagaat | 9000 |
| agacaacctg ttctcagagc aagacatctt ctcccttcta aatatctaca gaattggaga | 9060 |
| taaaattgtg gagaggcagg gaaattttc ttatgacttg attaaaatgg tggaaccgat | 9120 |
| atgcaacttg aagctgatga aattagcaag agaatcaagg cctttagtcc cacaattccc | 9180 |
| tcattttgaa aatcatatca agacttctgt tgatgaaggg gcaaaaattg accgaggtat | 9240 |
| aagattcctc catgatcaga taatgagtgt gaaaacagtg gatctcacac tggtgattta | 9300 |
| tggatcgttc agacattggg gtcatccttt tatagattat tacactggac tagaaaaatt | 9360 |
| acattcccaa gtaaccatga agaaagatat tgatgtgtca tatgcaaaag cacttgcaag | 9420 |
| tgatttagct cggattgttc tatttcaaca gttcaatgat cataaaaagt ggttcgtgaa | 9480 |
| tggagacttg ctccctcatg atcatccctt taaaagtcat gttaaagaaa atacatggcc | 9540 |
| cacagctgct caagttcaag attttggaga taaatggcat gaacttccgc tgattaaatg | 9600 |
| ttttgaaata cccgacttac tagacccatc gataatatac tctgacaaaa gtcattcaat | 9660 |
| gaataggtca gaggtgttga acatgtccg aatgaatccg aacactccta tcccctagtaa | 9720 |
| aaaggtgttg cagactatgt tggacacaaa ggctaccaat tggaaagaat tcttaaaga | 9780 |
| gattgatgag aagggcttag atgatgatga tctaattatt ggtcttaaag gaaaggagag | 9840 |
| ggaactgaag ttggcaggta gatttttctc cctaatgtct tggaaattgc gagaatactt | 9900 |
| tgtaattacc gaatatttga taaagactca tttcgtccct atgtttaaag gcctgacaat | 9960 |
| ggcggacgat ctaactgcag tcattaaaaa gatgttagat tcctcatccg gccaaggatt | 10020 |
| gaagtcatat gaggcaattt gcatagccaa tcacattgat tacgaaaaat ggaataacca | 10080 |
| ccaaaggaag ttatcaaacg gcccagtgtt ccgagttatg ggccagttct taggttatcc | 10140 |
| atccttaatc gagagaactc atgaattttt tgagaaaagt cttatatact acaatggaag | 10200 |
| accagacttg atgcgtgttc acaacaacac actgatcaat tcaacctccc aacgagtttg | 10260 |

```
ttggcaagga caagagggtg gactggaagg tctacggcaa aaaggatgga gtatcctcaa    10320
tctactggtt attcaaagag aggctaaaat cagaaacact gctgtcaaag tcttggcaca    10380
aggtgataat caagttattt gcacacagta taaaacgaag aaatcgagaa acgttgtaga    10440
attacagggt gctctcaatc aaatggtttc taataatgag aaaattatga ctgcaatcaa    10500
aatagggaca gggaagttag acttttgat aaatgacgat gagactatgc aatctgcaga    10560
ttacttgaat tatggaaaaa taccgatttt ccgtggagtg attagagggt tagagaccaa    10620
gagatggtca cgagtgactt gtgtcaccaa tgaccaaata cccacttgtg ctaatataat    10680
gagctcagtt tccacaaatg ctctcaccgt agctcatttt gctgagaacc caatcaatgc    10740
catgatacag tacaattatt tgggacatt tgctagactc ttgttgatga tgcatgatcc    10800
tgctcttcgt caatcattgt atgaagttca agataagata ccgggcttgc acagttctac    10860
tttcaaatac gccatgttgt atttggaccc ttccattgga ggagtgtcgg gcatgtcttt    10920
gtccaggttt ttgattagag ccttcccaga tcccgtaaca gaaagtctct cattctggag    10980
attcatccat gtacatgctc gaagtgagca tctgaaggag atgagtgcag tatttggaaa    11040
ccccgagata gccaagtttc gaataactca catagacaag ctagtagaag atccaacctc    11100
tctgaacatc gctatgggaa tgagtccagc gaacttgtta aagactgagg ttaaaaaatg    11160
cttaatcgaa tcaagacaaa ccatcaggaa ccaggtgatt aaggatgcaa ccatatattt    11220
gtatcatgaa gaggatcggc tcagaagttt cttatggtca ataaatcctc tgttccctag    11280
atttttaagt gaattcaaat caggcacttt ttgggagtc gcagacgggc tcatcagtct    11340 attcaaaat tctcgtacta ttcggaactc ctttaagaaa agtatcata gggaattgga    11400 tgatttgatt gtgaggagtg aggtatcctc tttgacacat ttagggaaac ttcatttgag    11460
aaggggatca tgtaaaatgt ggacatgttc agctactcat gctgacacat taagatacaa    11520
atcctggggc cgtacagtta ttgggacaac tgtaccccat ccattagaaa tgttgggtcc    11580
acaacatcga aaagagactc cttgtgcacc atgtaacaca tcagggttca attatgtttc    11640
tgtgcattgt ccagacggga tccatgacgt ctttagttca cggggaccat tgcctgctta    11700
tctagggtct aaaacatctg aatctacatc tattttgcag ccttgggaaa gggaaagcaa    11760
agtcccactg attaaaagag ctacacgtct tagagatgct atctcttggt ttgttgaacc    11820
cgactctaaa ctagcaatga ctatactttc taacatccac tctttaacag gcgaagaatg    11880
gaccaaaagg cagcatgggt tcaaagaac agggtctgcc cttcataggt tttcgacatc    11940
tcggatgagc catggtgggt tcgcatctca gagcactgca gcattgacca ggttgatggc    12000
aactacagac accatgaggg atctgggaga tcagaatttc gacttttat tccaagcaac    12060 gttgctctat gctcaaatta ccaccactgt tgcaagagac ggatggatca ccagttgtac    12120
agatcattat catattgcct gtaagtcctg tttgagaccc atagaagaga tcaccctgga    12180
ctcaagtatg gactacacgc ccccagatgt atcccatgtg ctgaagacat ggaggaatgg    12240
ggaaggttcg tggggacaag agataaaaca gatctatcct ttagaaggga attggaagaa    12300
tttagcacct gctgagcaat cctatcaagt cggcagatgt ataggttttc tatatggaga    12360
cttggcgtat agaaaatcta ctcatgccga ggacagttcc ctatttcctc tatctataca    12420
aggtcgtatt agaggtcgag gtttcttaaa agggttgcta gacggattaa tgagagcaag    12480
ttgctgccaa gtaatacacc ggagaagtct ggctcatttg aagaggccgg ccaacgcagt    12540
gtacggaggt ttgatttact tgattgataa attgagtgta tcacctccat tcctttctct    12600
```

```
tactagatca ggacctatta gagacgaatt agaaacgatt ccccacaaga tcccaacctc    12660
ctatccgaca agcaaccgtg atatgggggt gattgtcaga aattacttca ataccaatg    12720 ccgtctaatt gaaaagggaa aatacagatc acattattca caattatggt tattctcaga    12780
tgtcttatcc atagacttca ttggaccatt ctctatttcc accaccctct tgcaaatcct    12840
atacaagcca tttttatctg ggaaagataa gaatgagttg agagagctgg caaatctttc    12900
ttcattgcta agatcaggag aggggtggga agacatacat gtgaaattct tcaccaagga    12960
catattattg tgtccagagg aaatcagaca tgcttgcaag ttcgggattg ctaaggataa    13020
taataaagac atgagctatc ccccttgggg aagggaatcc agaggacaa ttacaacaat     13080 ccctgtttat tatacgacca ccccttaccc aaagatgcta gagatgcctc caagaatcca    13140
aaatcccctg ctgtccggaa tcaggttggg ccaattacca actggcgctc attataaaat    13200
tcggagtata ttacatggaa tgggaatcca ttacagggac ttcttgagtt gtggagacgg    13260
ctccggaggg atgactgctg cattactacg agaaaatgtg catagcagag gaatattcaa    13320
tagtctgtta gaattatcag ggtcagtcat gcgaggcgcc tctcctgagc cccccagtgc    13380
cctagaaact ttaggaggag ataaatcgag atgtgtaaat ggtgaaacat gttgggaata    13440
tccatctgac ttatgtgacc caaggacttg ggactatttc ctccgactca aagcaggctt    13500
ggggcttcaa attgatttaa ttgtaatgga tatggaagtt cgggattctt ctactagcct    13560
gaaaattgag acgaatgtta gaattatgt gcaccggatt ttggatgagc aaggagtttt     13620
aatctacaag acttatggaa catatatttg tgagagcgaa aagaatgcag taacaatcct    13680
tggtcccatg ttcaagacgg tcgacttagt tcaaacagaa tttagtagtt ctcaaacgtc    13740
tgaagtatat atggtatgta aaggtttgaa gaaattaatc gatgaaccca atcccgattg    13800
gtcttccatc aatgaatcct ggaaaaacct gtacgcattc cagtcatcag aacaggaatt    13860
tgccagagca aagaaggtta gtacatactt taccttgaca ggtattccct cccaattcat    13920
tcctgatcct tttgtaaaca ttgagactat gctacaaata ttcggagtac ccacgggtgt    13980
gtctcatgcg gctgccttaa aatcatctga tagacctgca gatttattga ccattagcct    14040
tttttatatg gcgattatat cgtattataa catcaatcat atcagagtag gaccgatacc    14100
tccgaacccc ccatcagatg gaattgcaca aaatgtgggg atcgctataa ctggtataag    14160
cttttggctg agtttgatgg agaaagacat tccactatat caacagtgtt tagcagttat    14220
ccagcaatca ttcccgatta ggtgggaggc tgtttcagta aaaggaggat acaagcagaa    14280
gtggagtact agaggtgatg ggctcccaaa agatacccga atttcagact ccttggcccc    14340
aatcgggaac tggatcagat ctctggaatt ggtccgaaac caagttcgtc taaatccatt    14400
caatgagatc ttgttcaatc agctatgtcg tacagtggat aatcatttga atggtcaaa     14460 tttgcgaaga aacacaggaa tgattgaatg gatcaataga cgaatttcaa aagaagaccg    14520
gtctatactg atgttgaaga gtgacctaca cgaggaaaac tcttggagag attaaaaaat    14580
catgaggaga ctccaaactt taagtatgaa aaaaactttg atccttaaga ccctcttgtg    14640
gtttttattt tttatctggt tttgtggtct tcgtgggtcg gcatggcatc tccacctcct    14700
cgcggtccga cctgggcatc cgaaggagga cgtcgtccac tcggatggct aagggaggg    14760 ccccgcgggg gctgctaaca aagcccgaaa ggaagctgag ttggctgctg ccaccgctga    14820
gcaataacta gcataacccc ttggggcctc taaacgggtc ttgagggtt ttttgctgaa     14880 aggaggaact atatccggat cgagacctcg atactagtga gctcc                    14925
```

```
<210> SEQ ID NO 4
<211> LENGTH: 5013
<212> TYPE: DNA
<213> ORGANISM: Artificial Sequence
<220> FEATURE:
<223> OTHER INFORMATION: recombinant DNA
<220> FEATURE:
<221> NAME/KEY: CDS
<222> LOCATION: (1)..(5013)

<400> SEQUENCE: 4
```

| | | | | | | | | | | | | | | | | |
|---|---|---|---|---|---|---|---|---|---|---|---|---|---|---|---|---|
| atg | cat | atc | tca | ctg | atg | tac | gct | atc | ctg | tgc | ctg | cag | ctg | tgc | ggc | 48 |
| Met | His | Ile | Ser | Leu | Met | Tyr | Ala | Ile | Leu | Cys | Leu | Gln | Leu | Cys | Gly | |
| 1 | | | | 5 | | | | | 10 | | | | | 15 | | |
| ctg | ggg | gaa | act | cac | gga | agc | cat | aac | gaa | act | cgc | cat | aac | aag | acc | 96 |
| Leu | Gly | Glu | Thr | His | Gly | Ser | His | Asn | Glu | Thr | Arg | His | Asn | Lys | Thr | |
| | | | | 20 | | | | | 25 | | | | | 30 | | |
| gac | aca | atg | acc | aca | cct | ggc | gat | aac | cca | agc | tcc | gag | ccc | cct | gtg | 144 |
| Asp | Thr | Met | Thr | Thr | Pro | Gly | Asp | Asn | Pro | Ser | Ser | Glu | Pro | Pro | Val | |
| | | 35 | | | | | 40 | | | | | 45 | | | | |
| agc | act | gcc | ctg | tcc | att | acc | ctg | gat | cct | tct | act | gtg | acc | cca | act | 192 |
| Ser | Thr | Ala | Leu | Ser | Ile | Thr | Leu | Asp | Pro | Ser | Thr | Val | Thr | Pro | Thr | |
| | 50 | | | | | 55 | | | | | 60 | | | | | |
| acc | cct | gct | tcc | gga | ctg | gag | gga | tct | gga | gaa | gtg | tac | acc | agc | cca | 240 |
| Thr | Pro | Ala | Ser | Gly | Leu | Glu | Gly | Ser | Gly | Glu | Val | Tyr | Thr | Ser | Pro | |
| 65 | | | | | 70 | | | | | 75 | | | | | 80 | |
| ccc | atc | aca | act | gga | tct | ctg | cca | ctg | agt | gag | acc | aca | cca | gaa | ctg | 288 |
| Pro | Ile | Thr | Thr | Gly | Ser | Leu | Pro | Leu | Ser | Glu | Thr | Thr | Pro | Glu | Leu | |
| | | | | 85 | | | | | 90 | | | | | 95 | | |
| ccc | gtg | act | acc | ggg | aca | gac | act | ctg | tct | gcc | gga | gac | gtg | gat | cca | 336 |
| Pro | Val | Thr | Thr | Gly | Thr | Asp | Thr | Leu | Ser | Ala | Gly | Asp | Val | Asp | Pro | |
| | | | 100 | | | | | 105 | | | | | 110 | | | |
| agt | acc | cag | aca | gca | gga | ggg | acc | tca | gct | cca | acc | gtg | agg | aca | agc | 384 |
| Ser | Thr | Gln | Thr | Ala | Gly | Gly | Thr | Ser | Ala | Pro | Thr | Val | Arg | Thr | Ser | |
| | | 115 | | | | | 120 | | | | | 125 | | | | |
| ctg | cct | aac | tca | cca | agc | act | ccc | tcc | acc | cct | cag | gat | act | cac | cat | 432 |
| Leu | Pro | Asn | Ser | Pro | Ser | Thr | Pro | Ser | Thr | Pro | Gln | Asp | Thr | His | His | |
| | 130 | | | | | 135 | | | | | 140 | | | | | |
| cct | gtc | cgc | aat | ctg | ctg | tcc | gtg | acc | tct | cct | ggc | cca | gac | gaa | act | 480 |
| Pro | Val | Arg | Asn | Leu | Leu | Ser | Val | Thr | Ser | Pro | Gly | Pro | Asp | Glu | Thr | |
| 145 | | | | | 150 | | | | | 155 | | | | | 160 | |
| agt | acc | cca | tca | gga | aca | ggc | aag | gag | tct | agt | gcc | act | tca | agc | ccc | 528 |
| Ser | Thr | Pro | Ser | Gly | Thr | Gly | Lys | Glu | Ser | Ser | Ala | Thr | Ser | Ser | Pro | |
| | | | | 165 | | | | | 170 | | | | | 175 | | |
| cac | ccc | gtg | agc | aat | agg | cct | cca | aca | ccc | cct | gca | act | gcc | cag | gga | 576 |
| His | Pro | Val | Ser | Asn | Arg | Pro | Pro | Thr | Pro | Pro | Ala | Thr | Ala | Gln | Gly | |
| | | | 180 | | | | | 185 | | | | | 190 | | | |
| cct | act | gag | aac | gat | tct | cac | aat | gct | acc | gag | cat | cca | gaa | tca | ctg | 624 |
| Pro | Thr | Glu | Asn | Asp | Ser | His | Asn | Ala | Thr | Glu | His | Pro | Glu | Ser | Leu | |
| | | 195 | | | | | 200 | | | | | 205 | | | | |
| acc | cag | agc | gca | aca | cct | ggc | ctg | atg | aca | agc | cca | act | cag | atc | gtc | 672 |
| Thr | Gln | Ser | Ala | Thr | Pro | Gly | Leu | Met | Thr | Ser | Pro | Thr | Gln | Ile | Val | |
| | 210 | | | | | 215 | | | | | 220 | | | | | |
| cac | ccc | cag | tcc | gcc | acc | cct | att | aca | gtg | cag | gac | aca | cat | cca | agt | 720 |
| His | Pro | Gln | Ser | Ala | Thr | Pro | Ile | Thr | Val | Gln | Asp | Thr | His | Pro | Ser | |
| 225 | | | | | 230 | | | | | 235 | | | | | 240 | |
| ccc | act | aac | cgg | tca | aaa | aga | aat | ctg | aag | atg | gag | atc | att | ctg | acc | 768 |
| Pro | Thr | Asn | Arg | Ser | Lys | Arg | Asn | Leu | Lys | Met | Glu | Ile | Ile | Leu | Thr | |
| | | | | 245 | | | | | 250 | | | | | 255 | | |
| ctg | agc | cag | gga | ctg | aag | aaa | tac | tat | ggc | aag | atc | ctg | agg | ctg | ctg | 816 |
| Leu | Ser | Gln | Gly | Leu | Lys | Lys | Tyr | Tyr | Gly | Lys | Ile | Leu | Arg | Leu | Leu | |
| | | | 260 | | | | | 265 | | | | | 270 | | | |

```
cag ctg acc ctg gag gaa gat aca gag gga ctg ctg gaa tgg tgt aaa        864
Gln Leu Thr Leu Glu Glu Asp Thr Glu Gly Leu Leu Glu Trp Cys Lys
            275                 280                 285 cgg aac ctg ggc ctg gac tgc gac gat acc ttc ttt cag aag aga atc        912
Arg Asn Leu Gly Leu Asp Cys Asp Asp Thr Phe Phe Gln Lys Arg Ile
        290                 295                 300 gag gag ttc ttc att aca ggg gag gga cac ttt aat gaa gtg ctg cag        960
Glu Glu Phe Phe Ile Thr Gly Glu Gly His Phe Asn Glu Val Leu Gln
305                 310                 315                 320 ttc cgc act cca ggc acc ctg tcc aca act gaa tct aca ccc gca ggg       1008
Phe Arg Thr Pro Gly Thr Leu Ser Thr Thr Glu Ser Thr Pro Ala Gly
                325                 330                 335 ctg cct act gcc gag cca ttc aaa tcc tac ttt gcc aag ggc ttc ctg       1056
Leu Pro Thr Ala Glu Pro Phe Lys Ser Tyr Phe Ala Lys Gly Phe Leu
            340                 345                 350 agc atc gat tcc ggg tac tat agc gcc aag tgt tat tcc ggc aca tcc       1104
Ser Ile Asp Ser Gly Tyr Tyr Ser Ala Lys Cys Tyr Ser Gly Thr Ser
        355                 360                 365 aac tct ggg ctg cag ctg atc aat att act aga cac agc acc agg atc       1152
Asn Ser Gly Leu Gln Leu Ile Asn Ile Thr Arg His Ser Thr Arg Ile
    370                 375                 380 gtg gac aca cct ggg cca aaa att aca aac ctg aag act atc aac tgc       1200
Val Asp Thr Pro Gly Pro Lys Ile Thr Asn Leu Lys Thr Ile Asn Cys
385                 390                 395                 400 att aat ctg aaa gct agc atc ttc aag gag cat cgc gag gtc gaa att       1248
Ile Asn Leu Lys Ala Ser Ile Phe Lys Glu His Arg Glu Val Glu Ile
                405                 410                 415 aat gtg ctg ctg cct cag gtg gca gtc aac ctg tcc aat tgt cac gtg       1296
Asn Val Leu Leu Pro Gln Val Ala Val Asn Leu Ser Asn Cys His Val
            420                 425                 430 gtc att aag tct cat gtc tgc gac tac agt ctg gac atc gat ggc gcc       1344
Val Ile Lys Ser His Val Cys Asp Tyr Ser Leu Asp Ile Asp Gly Ala
        435                 440                 445 gtg cgg ctg cct cac atc tac cat gag gga gtc ttt att cca ggc acc       1392
Val Arg Leu Pro His Ile Tyr His Glu Gly Val Phe Ile Pro Gly Thr
    450                 455                 460 tac aag atc gtg atc gac aag aaa aac aag ctg aat gat aga tgt aca       1440
Tyr Lys Ile Val Ile Asp Lys Lys Asn Lys Leu Asn Asp Arg Cys Thr
465                 470                 475                 480 ctg ttc act gac tgc gtc atc aaa ggg agg gag gtg cgc aag gga cag       1488
Leu Phe Thr Asp Cys Val Ile Lys Gly Arg Glu Val Arg Lys Gly Gln
                485                 490                 495 tct gtc ctg aga cag tat aaa act gaa atc agg att ggg aag gct tct       1536
Ser Val Leu Arg Gln Tyr Lys Thr Glu Ile Arg Ile Gly Lys Ala Ser
            500                 505                 510 acc gga agt cgg aga gtg ctg agt gag gaa cca tca gac gat tgc att       1584
Thr Gly Ser Arg Arg Val Leu Ser Glu Glu Pro Ser Asp Asp Cys Ile
        515                 520                 525 agc cgc acc cag ctg ctg cga aca gag act gcc gaa atc cac gga gat       1632
Ser Arg Thr Gln Leu Leu Arg Thr Glu Thr Ala Glu Ile His Gly Asp
    530                 535                 540 aac tac gga ggc ccc ggc gac aag atc acc att tgt aat ggc tct aca       1680
Asn Tyr Gly Gly Pro Gly Asp Lys Ile Thr Ile Cys Asn Gly Ser Thr
545                 550                 555                 560 att gtg gat cag cgg ctg gga agt gag ctg ggc tgc tat act atc aac       1728
Ile Val Asp Gln Arg Leu Gly Ser Glu Leu Gly Cys Tyr Thr Ile Asn
                565                 570                 575 aga gtg agg tcc ttc aaa ctg tgc gaa aac tct gct acc ggg aag aat       1776
Arg Val Arg Ser Phe Lys Leu Cys Glu Asn Ser Ala Thr Gly Lys Asn
```

-continued

```
                580                     585                     590
tgc gag att gac tcc gtg ccc gtc aaa tgt cga cag gga tac tgc ctg      1824
Cys Glu Ile Asp Ser Val Pro Val Lys Cys Arg Gln Gly Tyr Cys Leu
            595                     600                     605 cga atc acc cag gag gga aga gga cac gtg aag ctg tca aga ggc agc      1872
Arg Ile Thr Gln Glu Gly Arg Gly His Val Lys Leu Ser Arg Gly Ser
610                     615                     620 gag gtg gtc ctg gac gcc tgt gat acc tct tgc gaa atc atg att cct      1920
Glu Val Val Leu Asp Ala Cys Asp Thr Ser Cys Glu Ile Met Ile Pro
625                     630                     635                 640 aaa gga aca ggc gac atc ctg gtg gat tgc agc ggg gga cag cag cac      1968
Lys Gly Thr Gly Asp Ile Leu Val Asp Cys Ser Gly Gly Gln Gln His
            645                     650                     655 ttt ctg aag gac aac ctg atc gat ctg ggt tgt cca aaa att ccc ctg      2016
Phe Leu Lys Asp Asn Leu Ile Asp Leu Gly Cys Pro Lys Ile Pro Leu
            660                     665                     670 ctg gga aag atg gct atc tac att tgc agg atg agt aat cat ccc aaa      2064
Leu Gly Lys Met Ala Ile Tyr Ile Cys Arg Met Ser Asn His Pro Lys
            675                     680                     685 acc aca atg gca ttc ctg ttt tgg ttc tca ttt ggc tac gtg atc acc      2112
Thr Thr Met Ala Phe Leu Phe Trp Phe Ser Phe Gly Tyr Val Ile Thr
690                     695                     700 tgc atc ctg tgc aaa gcc atc ttc tat ctg ctg atc att gtg gga aca      2160
Cys Ile Leu Cys Lys Ala Ile Phe Tyr Leu Leu Ile Ile Val Gly Thr
705                     710                     715                 720 ctg ggc aaa cgg ctg aag cag tat aga gaa ctg aag ccc cag acc tgc      2208
Leu Gly Lys Arg Leu Lys Gln Tyr Arg Glu Leu Lys Pro Gln Thr Cys
            725                     730                     735 aca atc tgt gag act acc cct gtg aac gcc att gac gct gaa atg cac      2256
Thr Ile Cys Glu Thr Thr Pro Val Asn Ala Ile Asp Ala Glu Met His
            740                     745                     750 gat ctg aac tgt agc tac aat att tgc ccc tat tgt gca agc cga ctg      2304
Asp Leu Asn Cys Ser Tyr Asn Ile Cys Pro Tyr Cys Ala Ser Arg Leu
            755                     760                     765 acc tcc gac gga ctg gca cga cat gtc atc cag tgc cct aag cgg aaa      2352
Thr Ser Asp Gly Leu Ala Arg His Val Ile Gln Cys Pro Lys Arg Lys
770                     775                     780 gag aag gtg gag gaa aca gaa ctg tac ctg aat ctg gag agg att cca      2400
Glu Lys Val Glu Glu Thr Glu Leu Tyr Leu Asn Leu Glu Arg Ile Pro
785                     790                     795                 800 tgg gtg gtc cgc aaa ctg ctg cag gtg agt gag tca aca ggc gtc gcc      2448
Trp Val Val Arg Lys Leu Leu Gln Val Ser Glu Ser Thr Gly Val Ala
            805                     810                     815 ctg aag agg tcc tct tgg ctg atc gtc ctg ctg gtg ctg ttt act gtc      2496
Leu Lys Arg Ser Ser Trp Leu Ile Val Leu Leu Val Leu Phe Thr Val
            820                     825                     830 agc ctg tcc cca gtg cag tcc gct cca atc gga cag gga aaa aca att      2544
Ser Leu Ser Pro Val Gln Ser Ala Pro Ile Gly Gln Gly Lys Thr Ile
            835                     840                     845 gaa gca tac cgc gcc cga gag ggg tat act tct atc tgt ctg ttt gtg      2592
Glu Ala Tyr Arg Ala Arg Glu Gly Tyr Thr Ser Ile Cys Leu Phe Val
850                     855                     860 ctg gga tca atc ctg ttc att gtc agc tgc ctg atg aag ggc ctg gtc      2640
Leu Gly Ser Ile Leu Phe Ile Val Ser Cys Leu Met Lys Gly Leu Val
865                     870                     875                 880 gat tct gtg ggg aac agt ttc ttt ccc gga ctg tcc att tgc aaa acc      2688
Asp Ser Val Gly Asn Ser Phe Phe Pro Gly Leu Ser Ile Cys Lys Thr
            885                     890                     895 tgt tct atc agt tca att aat ggc ttt gag atc gaa agt cac aag tgc      2736
```

```
                Cys Ser Ile Ser Ser Ile Asn Gly Phe Glu Ile Glu Ser His Lys Cys
                                900                 905                 910 tac tgt tca ctg ttc tgc tgt cct tat tgc cgc cat tgt tcc aca gac         2784
Tyr Cys Ser Leu Phe Cys Cys Pro Tyr Cys Arg His Cys Ser Thr Asp
            915                 920                 925 aaa gag atc cac aag ctg cat ctg tca att tgc aag aaa agg aag aaa         2832
Lys Glu Ile His Lys Leu His Leu Ser Ile Cys Lys Lys Arg Lys Lys
    930                 935                 940 ggg agc aac gtc atg ctg gcc gtg tgc aag ctg atg tgc ttc cgc gcc         2880
Gly Ser Asn Val Met Leu Ala Val Cys Lys Leu Met Cys Phe Arg Ala
945                 950                 955                 960 acc atg gag gtg agt aac agg gct ctg ttt atc cgc tca atc att aat         2928
Thr Met Glu Val Ser Asn Arg Ala Leu Phe Ile Arg Ser Ile Ile Asn
                965                 970                 975 acc acc ttc gtg ctg tgc atc ctg att ctg gca gtc tgc gtg gtc tct         2976
Thr Thr Phe Val Leu Cys Ile Leu Ile Leu Ala Val Cys Val Val Ser
            980                 985                 990 acc agt gcc gtg gag atg gaa aat ctg ccc gct ggc aca tgg gag cgg         3024
Thr Ser Ala Val Glu Met Glu Asn Leu Pro Ala Gly Thr Trp Glu Arg
        995                 1000                1005 gag gaa gat ctg act aac ttt tgt cac cag gaa tgc caa gtg act             3069
Glu Glu Asp Leu Thr Asn Phe Cys His Gln Glu Cys Gln Val Thr
    1010                1015                1020 gag acc gaa tgc ctg tgc cct tac gag gca ctg gtg ctg aga aaa             3114
Glu Thr Glu Cys Leu Cys Pro Tyr Glu Ala Leu Val Leu Arg Lys
    1025                1030                1035 cca ctg ttc ctg gac agc acc gcc aaa ggc atg aag aac ctg ctg             3159
Pro Leu Phe Leu Asp Ser Thr Ala Lys Gly Met Lys Asn Leu Leu
    1040                1045                1050 aac agc acc agc ctg gaa aca tcc ctg tct atc gag gct ccc tgg             3204
Asn Ser Thr Ser Leu Glu Thr Ser Leu Ser Ile Glu Ala Pro Trp
    1055                1060                1065 ggg gca att aac gtc cag agt acc tat aag cct acc gtg tca aca             3249
Gly Ala Ile Asn Val Gln Ser Thr Tyr Lys Pro Thr Val Ser Thr
    1070                1075                1080 gct aat atc gca ctg agc tgg agc tcc gtc gag cac aga ggg aac             3294
Ala Asn Ile Ala Leu Ser Trp Ser Ser Val Glu His Arg Gly Asn
    1085                1090                1095 aaa atc ctg gtg agt gga agg agt gaa tca att atg aag ctg gag             3339
Lys Ile Leu Val Ser Gly Arg Ser Glu Ser Ile Met Lys Leu Glu
    1100                1105                1110 gaa aga acc ggc atc tct tgg gac ctg ggg gtg gag gat gct agc             3384
Glu Arg Thr Gly Ile Ser Trp Asp Leu Gly Val Glu Asp Ala Ser
    1115                1120                1125 gaa tcc aag ctg ctg aca gtg agc gtc atg gac ctg tca cag atg             3429
Glu Ser Lys Leu Leu Thr Val Ser Val Met Asp Leu Ser Gln Met
    1130                1135                1140 tac agc ccc gtc ttt gag tat ctg tcc ggc gat cga caa gtg gga             3474
Tyr Ser Pro Val Phe Glu Tyr Leu Ser Gly Asp Arg Gln Val Gly
    1145                1150                1155 gaa tgg ccc aaa gcc aca tgt act ggc gac tgc cct gag aga tgc             3519
Glu Trp Pro Lys Ala Thr Cys Thr Gly Asp Cys Pro Glu Arg Cys
    1160                1165                1170 ggg tgt act tct agt acc tgt ctg cac aag gaa tgg cca cat tcc             3564
Gly Cys Thr Ser Ser Thr Cys Leu His Lys Glu Trp Pro His Ser
    1175                1180                1185 cga aac tgg cgg tgt aat cca acc tgg tgc tgg gga gtg ggg aca             3609
Arg Asn Trp Arg Cys Asn Pro Thr Trp Cys Trp Gly Val Gly Thr
    1190                1195                1200
```

-continued

| | | | | | | | | | | | | | | |
|---|---|---|---|---|---|---|---|---|---|---|---|---|---|---|
| gga | tgc | act | tgc | tgt | ggc | ctg | gac | gtg | aaa | gat | ctg | ttt | aca | gat |
| Gly | Cys | Thr | Cys | Cys | Gly | Leu | Asp | Val | Lys | Asp | Leu | Phe | Thr | Asp |
| 1205 | | | | 1210 | | | | | 1215 | | | | | |

3654

| tac | atg | ttc | gtc | aaa | tgg | aag | gtg | gag | tat | atc | aag | aca | gaa | gca |
|---|---|---|---|---|---|---|---|---|---|---|---|---|---|---|
| Tyr | Met | Phe | Val | Lys | Trp | Lys | Val | Glu | Tyr | Ile | Lys | Thr | Glu | Ala |
| 1220 | | | | 1225 | | | | | 1230 | | | | | |

3699

| atc | gtg | tgc | gtg | gag | ctg | act | agc | cag | gaa | cgc | cag | tgc | tcc | ctg |
|---|---|---|---|---|---|---|---|---|---|---|---|---|---|---|
| Ile | Val | Cys | Val | Glu | Leu | Thr | Ser | Gln | Glu | Arg | Gln | Cys | Ser | Leu |
| 1235 | | | | 1240 | | | | | 1245 | | | | | |

3744

| att | gag | gcc | gga | acc | cga | ttc | aat | ctg | ggc | ccc | gtg | acc | atc | aca |
|---|---|---|---|---|---|---|---|---|---|---|---|---|---|---|
| Ile | Glu | Ala | Gly | Thr | Arg | Phe | Asn | Leu | Gly | Pro | Val | Thr | Ile | Thr |
| 1250 | | | | 1255 | | | | | 1260 | | | | | |

3789

| ctg | agc | gag | cct | cga | aac | att | cag | cag | aag | ctg | cca | ccc | gaa | atc |
|---|---|---|---|---|---|---|---|---|---|---|---|---|---|---|
| Leu | Ser | Glu | Pro | Arg | Asn | Ile | Gln | Gln | Lys | Leu | Pro | Pro | Glu | Ile |
| 1265 | | | | 1270 | | | | | 1275 | | | | | |

3834

| att | aca | ctg | cac | cca | aga | atc | gag | gaa | ggc | ttc | ttt | gac | ctg | atg |
|---|---|---|---|---|---|---|---|---|---|---|---|---|---|---|
| Ile | Thr | Leu | His | Pro | Arg | Ile | Glu | Glu | Gly | Phe | Phe | Asp | Leu | Met |
| 1280 | | | | 1285 | | | | | 1290 | | | | | |

3879

| cat | gtc | cag | aaa | gtg | ctg | tct | gcc | agt | acc | gtg | tgc | aag | ctg | cag |
|---|---|---|---|---|---|---|---|---|---|---|---|---|---|---|
| His | Val | Gln | Lys | Val | Leu | Ser | Ala | Ser | Thr | Val | Cys | Lys | Leu | Gln |
| 1295 | | | | 1300 | | | | | 1305 | | | | | |

3924

| agc | tgc | aca | cac | ggg | gtg | ccc | gga | gat | ctg | cag | gtc | tac | cat | atc |
|---|---|---|---|---|---|---|---|---|---|---|---|---|---|---|
| Ser | Cys | Thr | His | Gly | Val | Pro | Gly | Asp | Leu | Gln | Val | Tyr | His | Ile |
| 1310 | | | | 1315 | | | | | 1320 | | | | | |

3969

| gga | aac | ctg | ctg | aaa | ggc | gac | aaa | gtg | aat | ggg | cac | ctg | atc | cat |
|---|---|---|---|---|---|---|---|---|---|---|---|---|---|---|
| Gly | Asn | Leu | Leu | Lys | Gly | Asp | Lys | Val | Asn | Gly | His | Leu | Ile | His |
| 1325 | | | | 1330 | | | | | 1335 | | | | | |

4014

| aag | att | gag | ccc | cac | ttt | aat | acc | tcc | tgg | atg | tct | tgg | gat | ggc |
|---|---|---|---|---|---|---|---|---|---|---|---|---|---|---|
| Lys | Ile | Glu | Pro | His | Phe | Asn | Thr | Ser | Trp | Met | Ser | Trp | Asp | Gly |
| 1340 | | | | 1345 | | | | | 1350 | | | | | |

4059

| tgt | gac | ctg | gat | tac | tat | tgc | aac | atg | ggc | gac | tgg | cct | tcc | tgc |
|---|---|---|---|---|---|---|---|---|---|---|---|---|---|---|
| Cys | Asp | Leu | Asp | Tyr | Tyr | Cys | Asn | Met | Gly | Asp | Trp | Pro | Ser | Cys |
| 1355 | | | | 1360 | | | | | 1365 | | | | | |

4104

| act | tac | acc | ggg | gtc | aca | cag | cac | aat | cat | gca | tct | ttc | gtg | aac |
|---|---|---|---|---|---|---|---|---|---|---|---|---|---|---|
| Thr | Tyr | Thr | Gly | Val | Thr | Gln | His | Asn | His | Ala | Ser | Phe | Val | Asn |
| 1370 | | | | 1375 | | | | | 1380 | | | | | |

4149

| ctg | ctg | aat | atc | gag | acc | gat | tac | aca | aag | aac | ttc | cac | ttc | cat |
|---|---|---|---|---|---|---|---|---|---|---|---|---|---|---|
| Leu | Leu | Asn | Ile | Glu | Thr | Asp | Tyr | Thr | Lys | Asn | Phe | His | Phe | His |
| 1385 | | | | 1390 | | | | | 1395 | | | | | |

4194

| agc | aag | agg | gtg | act | gca | cac | ggg | gac | acc | cca | cag | ctg | gat | ctg |
|---|---|---|---|---|---|---|---|---|---|---|---|---|---|---|
| Ser | Lys | Arg | Val | Thr | Ala | His | Gly | Asp | Thr | Pro | Gln | Leu | Asp | Leu |
| 1400 | | | | 1405 | | | | | 1410 | | | | | |

4239

| aaa | gct | cga | cca | acc | tac | gga | gca | gga | gag | atc | aca | gtg | ctg | gtc |
|---|---|---|---|---|---|---|---|---|---|---|---|---|---|---|
| Lys | Ala | Arg | Pro | Thr | Tyr | Gly | Ala | Gly | Glu | Ile | Thr | Val | Leu | Val |
| 1415 | | | | 1420 | | | | | 1425 | | | | | |

4284

| gag | gtg | gct | gac | atg | gaa | ctg | cat | act | aag | aaa | atc | gaa | att | tct |
|---|---|---|---|---|---|---|---|---|---|---|---|---|---|---|
| Glu | Val | Ala | Asp | Met | Glu | Leu | His | Thr | Lys | Lys | Ile | Glu | Ile | Ser |
| 1430 | | | | 1435 | | | | | 1440 | | | | | |

4329

| gga | ctg | aag | ttc | gcc | agt | ctg | gct | tgc | acc | gga | tgt | tat | gca | tgc |
|---|---|---|---|---|---|---|---|---|---|---|---|---|---|---|
| Gly | Leu | Lys | Phe | Ala | Ser | Leu | Ala | Cys | Thr | Gly | Cys | Tyr | Ala | Cys |
| 1445 | | | | 1450 | | | | | 1455 | | | | | |

4374

| tca | agc | ggc | atc | agc | tgc | aaa | gtc | cgg | att | cac | gtg | gac | gag | cca |
|---|---|---|---|---|---|---|---|---|---|---|---|---|---|---|
| Ser | Ser | Gly | Ile | Ser | Cys | Lys | Val | Arg | Ile | His | Val | Asp | Glu | Pro |
| 1460 | | | | 1465 | | | | | 1470 | | | | | |

4419

| gat | gaa | ctg | acc | gtc | cat | gtg | aag | tcc | gac | gat | ccc | gat | gtg | gtc |
|---|---|---|---|---|---|---|---|---|---|---|---|---|---|---|
| Asp | Glu | Leu | Thr | Val | His | Val | Lys | Ser | Asp | Asp | Pro | Asp | Val | Val |
| 1475 | | | | 1480 | | | | | 1485 | | | | | |

4464

| gcc | gct | tcc | tct | agt | ctg | atg | gcc | agg | aag | ctg | gag | ttt | ggc | act |
|---|---|---|---|---|---|---|---|---|---|---|---|---|---|---|
| Ala | Ala | Ser | Ser | Ser | Leu | Met | Ala | Arg | Lys | Leu | Glu | Phe | Gly | Thr |
| 1490 | | | | 1495 | | | | | 1500 | | | | | |

4509

-continued

| | | | | | | | | | | |
|---|---|---|---|---|---|---|---|---|---|---|
| gac | tca | acc | ttc | aaa | gcc | ttc | agc | gcc | atg | cct | aag | acc | tcc | ctg | 4554 |
| Asp | Ser | Thr | Phe | Lys | Ala | Phe | Ser | Ala | Met | Pro | Lys | Thr | Ser | Leu | |
| 1505 | | | | 1510 | | | | | 1515 | | | | | | |

```
gac tca acc ttc aaa gcc ttc agc gcc atg cct aag acc tcc ctg    4554
Asp Ser Thr Phe Lys Ala Phe Ser Ala Met Pro Lys Thr Ser Leu
    1505                1510                1515 tgc ttc tac atc gtg gag cgc gaa cac tgt aaa tca tgc agc gag    4599
Cys Phe Tyr Ile Val Glu Arg Glu His Cys Lys Ser Cys Ser Glu
1520                1525                1530 gaa gat act aag aaa tgc gtg aac acc aag ctg gaa cag cca cag    4644
Glu Asp Thr Lys Lys Cys Val Asn Thr Lys Leu Glu Gln Pro Gln
    1535                1540                1545 tcc atc ctg att gag cat aaa ggg acc atc att gga aag cag aac    4689
Ser Ile Leu Ile Glu His Lys Gly Thr Ile Ile Gly Lys Gln Asn
1550                1555                1560 agc aca tgt act gct aag gca tct tgc tgg ctg gag agt gtg aaa    4734
Ser Thr Cys Thr Ala Lys Ala Ser Cys Trp Leu Glu Ser Val Lys
    1565                1570                1575 tca ttc ttt tat ggc ctg aag aac atg ctg agc ggc atc ttt ggg    4779
Ser Phe Phe Tyr Gly Leu Lys Asn Met Leu Ser Gly Ile Phe Gly
1580                1585                1590 aac gtg ttc atg ggg att ttc ctg ttt ctg gcc ccc ttt atc ctg    4824
Asn Val Phe Met Gly Ile Phe Leu Phe Leu Ala Pro Phe Ile Leu
    1595                1600                1605 ctg att ctg ttc ttt atg ttc gga tgg aga atc ctg ttc tgc ttt    4869
Leu Ile Leu Phe Phe Met Phe Gly Trp Arg Ile Leu Phe Cys Phe
1610                1615                1620 aaa tgc tgt agg cgc aca cga ggc ctg ttc aaa tac cgg cac cgg    4914
Lys Cys Cys Arg Arg Thr Arg Gly Leu Phe Lys Tyr Arg His Arg
    1625                1630                1635 aag gac gat gag gaa act gga tat cga cag atc att gag aag ctg    4959
Lys Asp Asp Glu Glu Thr Gly Tyr Arg Gln Ile Ile Glu Lys Leu
1640                1645                1650 aac aat aag aaa ggc aaa aac aag ctg ctg gac ggg gaa aga ctg    5004
Asn Asn Lys Lys Gly Lys Asn Lys Leu Leu Asp Gly Glu Arg Leu
    1655                1660                1665 gct gat tga                                                    5013
Ala Asp
1670

<210> SEQ ID NO 5
<211> LENGTH: 1670
<212> TYPE: PRT
<213> ORGANISM: Artificial Sequence
<220> FEATURE:
<223> OTHER INFORMATION: Synthetic Construct

<400> SEQUENCE: 5

Met His Ile Ser Leu Met Tyr Ala Ile Leu Cys Leu Gln Leu Cys Gly
1               5                   10                  15

Leu Gly Glu Thr His Gly Ser His Asn Glu Thr Arg His Asn Lys Thr
            20                  25                  30

Asp Thr Met Thr Thr Pro Gly Asp Asn Pro Ser Ser Glu Pro Pro Val
        35                  40                  45

Ser Thr Ala Leu Ser Ile Thr Leu Asp Pro Ser Thr Val Thr Pro Thr
    50                  55                  60

Thr Pro Ala Ser Gly Leu Glu Gly Ser Gly Glu Val Tyr Thr Ser Pro
65                  70                  75                  80

Pro Ile Thr Thr Gly Ser Leu Pro Leu Ser Glu Thr Thr Pro Glu Leu
                85                  90                  95

Pro Val Thr Thr Gly Thr Asp Thr Leu Ser Ala Gly Asp Val Asp Pro
            100                 105                 110
```

Ser Thr Gln Thr Ala Gly Gly Thr Ser Ala Pro Thr Val Arg Thr Ser
            115                 120                 125

Leu Pro Asn Ser Pro Ser Thr Pro Ser Thr Pro Gln Asp Thr His His
        130                 135                 140

Pro Val Arg Asn Leu Leu Ser Val Thr Ser Pro Gly Pro Asp Glu Thr
145                 150                 155                 160

Ser Thr Pro Ser Gly Thr Gly Lys Glu Ser Ala Thr Ser Ser Pro
            165                 170                 175

His Pro Val Ser Asn Arg Pro Pro Thr Pro Pro Ala Thr Ala Gln Gly
            180                 185                 190

Pro Thr Glu Asn Asp Ser His Asn Ala Thr Glu His Pro Glu Ser Leu
            195                 200                 205

Thr Gln Ser Ala Thr Pro Gly Leu Met Thr Ser Pro Thr Gln Ile Val
            210                 215                 220

His Pro Gln Ser Ala Thr Pro Ile Thr Val Gln Asp Thr His Pro Ser
225                 230                 235                 240

Pro Thr Asn Arg Ser Lys Arg Asn Leu Lys Met Glu Ile Ile Leu Thr
            245                 250                 255

Leu Ser Gln Gly Leu Lys Lys Tyr Tyr Gly Lys Ile Leu Arg Leu Leu
            260                 265                 270

Gln Leu Thr Leu Glu Glu Asp Thr Glu Gly Leu Leu Glu Trp Cys Lys
            275                 280                 285

Arg Asn Leu Gly Leu Asp Cys Asp Asp Thr Phe Phe Gln Lys Arg Ile
            290                 295                 300

Glu Glu Phe Phe Ile Thr Gly Glu Gly His Phe Asn Glu Val Leu Gln
305                 310                 315                 320

Phe Arg Thr Pro Gly Thr Leu Ser Thr Thr Glu Ser Thr Pro Ala Gly
            325                 330                 335

Leu Pro Thr Ala Glu Pro Phe Lys Ser Tyr Phe Ala Lys Gly Phe Leu
            340                 345                 350

Ser Ile Asp Ser Gly Tyr Tyr Ser Ala Lys Cys Tyr Ser Gly Thr Ser
            355                 360                 365

Asn Ser Gly Leu Gln Leu Ile Asn Ile Thr Arg His Ser Thr Arg Ile
            370                 375                 380

Val Asp Thr Pro Gly Pro Lys Ile Thr Asn Leu Lys Thr Ile Asn Cys
385                 390                 395                 400

Ile Asn Leu Lys Ala Ser Ile Phe Lys Glu His Arg Glu Val Glu Ile
            405                 410                 415

Asn Val Leu Leu Pro Gln Val Ala Val Asn Leu Ser Asn Cys His Val
            420                 425                 430

Val Ile Lys Ser His Val Cys Asp Tyr Ser Leu Asp Ile Asp Gly Ala
            435                 440                 445

Val Arg Leu Pro His Ile Tyr His Glu Gly Val Phe Ile Pro Gly Thr
            450                 455                 460

Tyr Lys Ile Val Ile Asp Lys Lys Asn Lys Leu Asn Asp Arg Cys Thr
465                 470                 475                 480

Leu Phe Thr Asp Cys Val Ile Lys Gly Arg Glu Val Arg Lys Gly Gln
            485                 490                 495

Ser Val Leu Arg Gln Tyr Lys Thr Glu Ile Arg Ile Gly Lys Ala Ser
            500                 505                 510

Thr Gly Ser Arg Arg Val Leu Ser Glu Glu Pro Ser Asp Asp Cys Ile
            515                 520                 525

```
Ser Arg Thr Gln Leu Leu Arg Thr Glu Thr Ala Glu Ile His Gly Asp
    530                 535                 540

Asn Tyr Gly Gly Pro Gly Asp Lys Ile Thr Ile Cys Asn Gly Ser Thr
545                 550                 555                 560

Ile Val Asp Gln Arg Leu Gly Ser Glu Leu Gly Cys Tyr Thr Ile Asn
                565                 570                 575

Arg Val Arg Ser Phe Lys Leu Cys Glu Asn Ser Ala Thr Gly Lys Asn
                580                 585                 590

Cys Glu Ile Asp Ser Val Pro Lys Cys Arg Gln Gly Tyr Cys Leu
            595                 600                 605

Arg Ile Thr Gln Glu Gly Arg Gly His Val Lys Leu Ser Arg Gly Ser
    610                 615                 620

Glu Val Val Leu Asp Ala Cys Asp Thr Ser Cys Glu Ile Met Ile Pro
625                 630                 635                 640

Lys Gly Thr Gly Asp Ile Leu Val Asp Cys Ser Gly Gly Gln Gln His
                645                 650                 655

Phe Leu Lys Asp Asn Leu Ile Asp Leu Gly Cys Pro Lys Ile Pro Leu
                660                 665                 670

Leu Gly Lys Met Ala Ile Tyr Ile Cys Arg Met Ser Asn His Pro Lys
            675                 680                 685

Thr Thr Met Ala Phe Leu Phe Trp Phe Ser Phe Gly Tyr Val Ile Thr
    690                 695                 700

Cys Ile Leu Cys Lys Ala Ile Phe Tyr Leu Leu Ile Ile Val Gly Thr
705                 710                 715                 720

Leu Gly Lys Arg Leu Lys Gln Tyr Arg Glu Leu Lys Pro Gln Thr Cys
                725                 730                 735

Thr Ile Cys Glu Thr Thr Pro Val Asn Ala Ile Asp Ala Glu Met His
            740                 745                 750

Asp Leu Asn Cys Ser Tyr Asn Ile Cys Pro Tyr Cys Ala Ser Arg Leu
    755                 760                 765

Thr Ser Asp Gly Leu Ala Arg His Val Ile Gln Cys Pro Lys Arg Lys
770                 775                 780

Glu Lys Val Glu Glu Thr Glu Leu Tyr Leu Asn Leu Glu Arg Ile Pro
785                 790                 795                 800

Trp Val Val Arg Lys Leu Leu Gln Val Ser Glu Ser Thr Gly Val Ala
                805                 810                 815

Leu Lys Arg Ser Ser Trp Leu Ile Val Leu Leu Val Leu Phe Thr Val
            820                 825                 830

Ser Leu Ser Pro Val Gln Ser Ala Pro Ile Gly Gln Gly Lys Thr Ile
    835                 840                 845

Glu Ala Tyr Arg Ala Arg Glu Gly Tyr Thr Ser Ile Cys Leu Phe Val
850                 855                 860

Leu Gly Ser Ile Leu Phe Ile Val Ser Cys Leu Met Lys Gly Leu Val
865                 870                 875                 880

Asp Ser Val Gly Asn Ser Phe Phe Pro Gly Leu Ser Ile Cys Lys Thr
                885                 890                 895

Cys Ser Ile Ser Ser Ile Asn Gly Phe Glu Ile Glu Ser His Lys Cys
            900                 905                 910

Tyr Cys Ser Leu Phe Cys Cys Pro Tyr Cys Arg His Cys Ser Thr Asp
    915                 920                 925

Lys Glu Ile His Lys Leu His Leu Ser Ile Cys Lys Lys Arg Lys Lys
930                 935                 940

Gly Ser Asn Val Met Leu Ala Val Cys Lys Leu Met Cys Phe Arg Ala
```

```
                945                 950                 955                 960
           Thr Met Glu Val Ser Asn Arg Ala Leu Phe Ile Arg Ser Ile Ile Asn
                           965                 970                 975
           Thr Thr Phe Val Leu Cys Ile Leu Ile Leu Ala Val Cys Val Val Ser
                           980                 985                 990
           Thr Ser Ala Val Glu Met Glu Asn Leu Pro Ala Gly Thr Trp Glu Arg
                           995                 1000                1005
           Glu Glu Asp Leu Thr Asn Phe Cys His Gln Glu Cys Gln Val Thr
               1010                1015                1020
           Glu Thr Glu Cys Leu Cys Pro Tyr Glu Ala Leu Val Leu Arg Lys
               1025                1030                1035
           Pro Leu Phe Leu Asp Ser Thr Ala Lys Gly Met Lys Asn Leu Leu
               1040                1045                1050
           Asn Ser Thr Ser Leu Glu Thr Ser Leu Ser Ile Glu Ala Pro Trp
               1055                1060                1065
           Gly Ala Ile Asn Val Gln Ser Thr Tyr Lys Pro Thr Val Ser Thr
               1070                1075                1080
           Ala Asn Ile Ala Leu Ser Trp Ser Ser Val Glu His Arg Gly Asn
               1085                1090                1095
           Lys Ile Leu Val Ser Gly Arg Ser Glu Ser Ile Met Lys Leu Glu
               1100                1105                1110
           Glu Arg Thr Gly Ile Ser Trp Asp Leu Gly Val Glu Asp Ala Ser
               1115                1120                1125
           Glu Ser Lys Leu Leu Thr Val Ser Val Met Asp Leu Ser Gln Met
               1130                1135                1140
           Tyr Ser Pro Val Phe Glu Tyr Leu Ser Gly Asp Arg Gln Val Gly
               1145                1150                1155
           Glu Trp Pro Lys Ala Thr Cys Thr Gly Asp Cys Pro Glu Arg Cys
               1160                1165                1170
           Gly Cys Thr Ser Ser Thr Cys Leu His Lys Glu Trp Pro His Ser
               1175                1180                1185
           Arg Asn Trp Arg Cys Asn Pro Thr Trp Cys Trp Gly Val Gly Thr
               1190                1195                1200
           Gly Cys Thr Cys Cys Gly Leu Asp Val Lys Asp Leu Phe Thr Asp
               1205                1210                1215
           Tyr Met Phe Val Lys Trp Lys Val Glu Tyr Ile Lys Thr Glu Ala
               1220                1225                1230
           Ile Val Cys Val Glu Leu Thr Ser Gln Glu Arg Gln Cys Ser Leu
               1235                1240                1245
           Ile Glu Ala Gly Thr Arg Phe Asn Leu Gly Pro Val Thr Ile Thr
               1250                1255                1260
           Leu Ser Glu Pro Arg Asn Ile Gln Gln Lys Leu Pro Pro Glu Ile
               1265                1270                1275
           Ile Thr Leu His Pro Arg Ile Glu Glu Gly Phe Phe Asp Leu Met
               1280                1285                1290
           His Val Gln Lys Val Leu Ser Ala Ser Thr Val Cys Lys Leu Gln
               1295                1300                1305
           Ser Cys Thr His Gly Val Pro Gly Asp Leu Gln Val Tyr His Ile
               1310                1315                1320
           Gly Asn Leu Leu Lys Gly Asp Lys Val Asn Gly His Leu Ile His
               1325                1330                1335
           Lys Ile Glu Pro His Phe Asn Thr Ser Trp Met Ser Trp Asp Gly
               1340                1345                1350
```

| Cys Asp Leu Asp Tyr Tyr Cys Asn Met Gly Asp Trp Pro Ser Cys
      1355                1360                1365

Thr Tyr Thr Gly Val Thr Gln His Asn His Ala Ser Phe Val Asn
      1370                1375                1380

Leu Leu Asn Ile Glu Thr Asp Tyr Thr Lys Asn Phe His Phe His
      1385                1390                1395

Ser Lys Arg Val Thr Ala His Gly Asp Thr Pro Gln Leu Asp Leu
      1400                1405                1410

Lys Ala Arg Pro Thr Tyr Gly Ala Gly Glu Ile Thr Val Leu Val
      1415                1420                1425

Glu Val Ala Asp Met Glu Leu His Thr Lys Ile Glu Ile Ser
      1430                1435                1440

Gly Leu Lys Phe Ala Ser Leu Ala Cys Thr Gly Cys Tyr Ala Cys
      1445                1450                1455

Ser Ser Gly Ile Ser Cys Lys Val Arg Ile His Val Asp Glu Pro
      1460                1465                1470

Asp Glu Leu Thr Val His Val Lys Ser Asp Asp Pro Asp Val Val
      1475                1480                1485

Ala Ala Ser Ser Ser Leu Met Ala Arg Lys Leu Glu Phe Gly Thr
      1490                1495                1500

Asp Ser Thr Phe Lys Ala Phe Ser Ala Met Pro Lys Thr Ser Leu
      1505                1510                1515

Cys Phe Tyr Ile Val Glu Arg Glu His Cys Lys Ser Cys Ser Glu
      1520                1525                1530

Glu Asp Thr Lys Lys Cys Val Asn Thr Lys Leu Glu Gln Pro Gln
      1535                1540                1545

Ser Ile Leu Ile Glu His Lys Gly Thr Ile Ile Gly Lys Gln Asn
      1550                1555                1560

Ser Thr Cys Thr Ala Lys Ala Ser Cys Trp Leu Glu Ser Val Lys
      1565                1570                1575

Ser Phe Phe Tyr Gly Leu Lys Asn Met Leu Ser Gly Ile Phe Gly
      1580                1585                1590

Asn Val Phe Met Gly Ile Phe Leu Phe Leu Ala Pro Phe Ile Leu
      1595                1600                1605

Leu Ile Leu Phe Phe Met Phe Gly Trp Arg Ile Leu Phe Cys Phe
      1610                1615                1620

Lys Cys Cys Arg Arg Thr Arg Gly Leu Phe Lys Tyr Arg His Arg
      1625                1630                1635

Lys Asp Asp Glu Glu Thr Gly Tyr Arg Gln Ile Ile Glu Lys Leu
      1640                1645                1650

Asn Asn Lys Lys Gly Lys Asn Lys Leu Leu Asp Gly Glu Arg Leu
      1655                1660                1665

Ala Asp
      1670

<210> SEQ ID NO 6
<211> LENGTH: 5055
<212> TYPE: DNA
<213> ORGANISM: Artificial Sequence
<220> FEATURE:
<223> OTHER INFORMATION: Recombinant DNA

<400> SEQUENCE: 6
atgcatatct cactgatgta cgctatcctg tgcctgcagc tgtgcggcct gggggaaact    60

-continued

```
cacggaagcc ataacgaaac tcgccataac aagaccgaca caatgaccac acctggcgat      120
aacccaagct ccgagccccc tgtgagcact gccctgtcca ttaccctgga tccttctact      180
gtgaccccaa ctacccctgc ttccggactg gagggatctg gagaagtgta caccagccca      240
cccatcacaa ctggatctct gccactgagt gagaccacac cagaactgcc cgtgactacc      300
gggacagaca ctctgtctgc cggagacgtg gatccaagta cccagacagc aggagggacc      360
tcagctccaa ccgtgaggac aagcctgcct aactcaccaa gcactccctc cacccctcag      420
gatactcacc atcctgtccg caatctgctg tccgtgacct ctcctggccc agacgaaact      480
agtaccccat caggaacagg caaggagtct agtgccactt caagccccca ccccgtgagc      540
aataggcctc caacaccccc tgcaactgcc cagggaccta ctgagaacga ttctcacaat      600
gctaccgagc atccagaatc actgacccag agcgcaacac ctggcctgat gacaagccca      660
actcagatcg tccaccccca gtccgccacc cctattacag tgcaggacac acatccaagt      720
cccactaacc ggtcaaaaag aaatctgaag atggagatca ttctgaccct gagccaggga      780
ctgaagaaat actatggcaa gatcctgagg ctgctgcagc tgaccctgga ggaagataca      840
gagggactgc tggaatggtg taaacgaaac ctgggcctgg actgcgacga taccttcttt      900
cagaagagaa tcgaggagtt cttcattaca ggggagggac actttaatga agtgctgcag      960
ttccgcactc caggcaccct gtccacaact gaatctacac ccgcagggct gcctactgcc     1020
gagccattca aatcctactt tgccaagggc ttcctgagca tcgattccgg gtactatagc     1080
gccaagtgtt attccggcac atccaactct gggctgcagc tgatcaatat tactagacac     1140
agcaccagga tcgtggacac acctgggcca aaaattacaa acctgaagac tatcaactgc     1200
attaatctga agctagcat cttcaaggag catcgcgagg tcgaaattaa tgtgctgctg     1260
cctcaggtgg cagtcaacct gtccaattgt cacgtggtca ttaagtctca tgtctgcgac     1320
tacagtctgg acatcgatgg cgccgtgcgg ctgcctcaca tctaccatga gggagtcttt     1380
attccaggca cctacaagat cgtgatcgac aagaaaaaca agctgaatga tagatgtaca     1440
ctgttcactg actgcgtcat caaagggagg gaggtgcgca agggacagtc tgtcctgaga     1500
cagtataaaa ctgaaatcag gattgggaag gcttctaccg gaagtcggag actgctgagt     1560
gaggaaccat cagacgattg cattagccgc acccagctgc tgcgaacaga gactgccgaa     1620
atccacggag ataactacgg aggccccggc gacaagatca ccatttgtaa tggctctaca     1680
attgtggatc agcggctggg aagtgagctg ggctgctata ctatcaacag agtgaggtcc     1740
ttcaaactgt gcgaaaactc tgctaccggg aagaattgcg agattgactc cgtgcccgtc     1800
aaatgtcgac agggatactg cctgcgaatc acccaggagg gaagaggaca cgtgaagctg     1860
tcaagaggca gcgaggtggt cctggacgcc tgtgatacct cttgcgaaat catgattcct     1920
aaaggaacag gcgacatcct ggtggattgc agcggggac agcagcactt tctgaaggac     1980
aacctgatcg atctggggtg tccaaaaatt cccctgctgg aaagatggc tatctacatt     2040 tgcaggatga gtaatcatcc caaaaccaca atggcattcc tgtttggtt ctcatttggc     2100 tacgtgatca cctgcatcct gtgcaaagcc atcttctatc tgctgatcat tgtgggaaca     2160
ctgggcaaac ggctgaagca gtatagagaa ctgaagcccc agacctgcac aatctgtgag     2220 actaccctg tgaacgccat tgcgctgaa atgcacgatc tgaactgtag ctacaatatt     2280 tgccctatt gtgcaagccg actgacctcc gacggactgg cacgacatgt catccagtgc     2340
cctaagcgga aagagaaggt ggaggaaaca gaactgtacc tgaatctgga gaggattcca     2400
tgggtggtcc gcaaactgct gcaggtgagt gagtcaacag gcgtcgccct gaagaggtcc     2460
```

```
tcttggctga tcgtcctgct ggtgctgttt actgtcagcc tgtccccagt gcagtccgct    2520
ccaatcggac agggaaaaac aattgaagca taccgcgccc gagagggta tacttctatc     2580 tgtctgtttg tgctgggatc aatcctgttc attgtcagct gcctgatgaa gggcctggtc    2640
gattctgtgg ggaacagttt ctttcccgga ctgtccattt gcaaaacctg ttctatcagt    2700
tcaattaatg gctttgagat cgaaagtcac aagtgctact gttcactgtt ctgctgtcct    2760
tattgccgcc attgttccac agacaaagag atccacaagc tgcatctgtc aatttgcaag    2820
aaaaggaaga aagggagcaa cgtcatgctg ccgtgtgca agctgatgtg cttccgcgcc     2880
accatggagg tgagtaacag ggctctgttt atccgctcaa tcattaatac caccttcgtg    2940
ctgtgcatcc tgattctggc agtctgcgtg gtctctacca gtgccgtgga tggaaaat     3000 ctgcccgctg gcacatggga gcgggaggaa gatctgacta acttttgtca ccaggaatgc    3060
caagtgactg agaccgaatg cctgtgccct tacgaggcac tggtgctgag aaaaccactg    3120
ttcctggaca gcaccgccaa aggcatgaag aacctgctga acagcaccag cctggaaaca    3180
tccctgtcta tcgaggctcc ctgggggggca attaacgtcc agagtaccta taagcctacc    3240
gtgtcaacag ctaatatcgc actgagctgg agctccgtcg agcacagagg gaacaaaatc    3300
ctggtgagtg gaaggagtga atcaattatg aagctggagg aaagaaccgg catctcttgg    3360
gacctggggg tggaggatgc tagcgaatcc aagctgctga cagtgagcgt catggacctg    3420
tcacagatgt acagccccgt ctttgagtat ctgtccggcg atcgacaagt gggagaatgg    3480
cccaaagcca catgtactgg cgactgccct gagagatgcg ggtgtacttc tagtacctgt    3540
ctgcacaagg aatggccaca ttcccgaaac tggcggtgta atccaacctg gtgctgggga    3600
gtggggacag gatgcacttg ctgtggcctg gacgtgaaag atctgtttac agattacatg    3660
ttcgtcaaat ggaaggtgga gtatatcaag acagaagcaa tcgtgtgcgt ggagctgact    3720
agccaggaac gccagtgctc cctgattgag gccggaaccc gattcaatct gggcccccgtg    3780 accatcacac tgagcgagcc tcgaaacatt cagcagaagc tgccacccga aatcattaca    3840
ctgcacccaa gaatcgagga aggcttcttt gacctgatgc atgtccagaa agtgctgtct    3900
gccagtaccg tgtgcaagct gcagagctgc acacacgggg tgcccggaga tctgcaggtc    3960
taccatatcg gaaacctgct gaaaggcgac aaagtgaatg gcacctgat ccataagatt     4020 gagcccact ttaatacctc ctggatgtct tgggatggct gtgacctgga ttactattgc     4080
aacatgggcg actggccttc ctgcacttac accggggtca cacagcacaa tcatgcatct    4140
ttcgtgaacc tgctgaatat cgagaccgat tacacaaaga acttccactt ccatagcaag    4200
agggtgactg cacacgggga caccccacag ctggatctga agctcgacc aacctacgga     4260 gcaggagaga tcagtgctct ggtcgaggtg gctgacatgg aactgcatac taagaaaatc    4320
gaaatttctg gactgaagtt cgccagtctg gcttgcaccg gatgttatgc atgctcaagc    4380
ggcatcagct gcaaagtccg gattcacgtg gacgagccag atgaactgac cgtccatgtg    4440
aagtccgacg atcccgatgt ggtcgccgct tcctctagtc tgatggccag gaagctggag    4500
tttggcactg actcaacctt caaagccttc agcgccatgc ctaagacctc cctgtgcttc    4560
tacatcgtgg agcgcgaaca ctgtaaatca tgcagcgagg aagatactaa gaaatgcgtg    4620
aacaccaagc tggaacagcc acagtccatc ctgattgagc ataaagggac catcattgga    4680
aagcagaaca gcacatgtac tgctaaggca tcttgctggc tggagagtgt gaaatcattc    4740
ttttatggcc tgaagaacat gctgagcggc atctttggga acgtgttcat ggggattttc    4800
```

```
ctgtttctgg ccccctttat cctgctgatt ctgttcttta tgttcggatg gagaatcctg    4860
ttctgcttta aatgctgtag gcgcacacga ggcctgttca aataccggca cctgaaggac    4920
gatgaggaaa ctggatatcg acggatcatt gagaagctga acaataagaa aggcaaaaac    4980
aagctgctgg acggggaaag actggctgat agaagaatcg cagaactgtt tagcaccaag    5040
acccacatcg ggcag                                                    5055
```

<210> SEQ ID NO 7
<211> LENGTH: 1670
<212> TYPE: PRT
<213> ORGANISM: Artificial Sequence
<220> FEATURE:
<223> OTHER INFORMATION: Recombinant Protein

<400> SEQUENCE: 7

```
Met His Ile Ser Leu Met Tyr Ala Ile Leu Cys Leu Gln Leu Cys Gly
1               5                   10                  15

Leu Gly Glu Thr His Gly Ser His Asn Glu Thr Arg His Asn Lys Thr
            20                  25                  30

Asp Thr Met Thr Thr Pro Gly Asp Asn Pro Ser Ser Glu Pro Pro Val
        35                  40                  45

Ser Thr Ala Leu Ser Ile Thr Leu Asp Pro Ser Thr Val Thr Pro Thr
    50                  55                  60

Thr Pro Ala Ser Gly Leu Glu Gly Ser Gly Glu Val Tyr Thr Ser Pro
65                  70                  75                  80

Pro Ile Thr Thr Gly Ser Leu Pro Leu Ser Glu Thr Thr Pro Glu Leu
                85                  90                  95

Pro Val Thr Thr Gly Thr Asp Thr Leu Ser Ala Gly Asp Val Asp Pro
            100                 105                 110

Ser Thr Gln Thr Ala Gly Gly Thr Ser Ala Pro Thr Val Arg Thr Ser
        115                 120                 125

Leu Pro Asn Ser Pro Ser Thr Pro Ser Thr Pro Gln Asp Thr His His
    130                 135                 140

Pro Val Arg Asn Leu Leu Ser Val Thr Ser Pro Gly Pro Asp Glu Thr
145                 150                 155                 160

Ser Thr Pro Ser Gly Thr Gly Lys Glu Ser Ser Ala Thr Ser Ser Pro
                165                 170                 175

His Pro Val Ser Asn Arg Pro Pro Thr Pro Ala Thr Ala Gln Gly
            180                 185                 190

Pro Thr Glu Asn Asp Ser His Asn Ala Thr Glu His Pro Glu Ser Leu
        195                 200                 205

Thr Gln Ser Ala Thr Pro Gly Leu Met Thr Ser Pro Thr Gln Ile Val
    210                 215                 220

His Pro Gln Ser Ala Thr Pro Ile Thr Val Gln Asp Thr His Pro Ser
225                 230                 235                 240

Pro Thr Asn Arg Ser Lys Arg Asn Leu Lys Met Glu Ile Ile Leu Thr
                245                 250                 255

Leu Ser Gln Gly Leu Lys Lys Tyr Tyr Gly Lys Ile Leu Arg Leu Leu
            260                 265                 270

Gln Leu Thr Leu Glu Glu Asp Thr Glu Gly Leu Leu Glu Trp Cys Lys
        275                 280                 285

Arg Asn Leu Gly Leu Asp Cys Asp Asp Thr Phe Phe Gln Lys Arg Ile
    290                 295                 300

Glu Glu Phe Phe Ile Thr Gly Glu Gly His Phe Asn Glu Val Leu Gln
305                 310                 315                 320
```

```
Phe Arg Thr Pro Gly Thr Leu Ser Thr Thr Glu Ser Thr Pro Ala Gly
                325                 330                 335

Leu Pro Thr Ala Glu Pro Phe Lys Ser Tyr Phe Ala Lys Gly Phe Leu
            340                 345                 350

Ser Ile Asp Ser Gly Tyr Tyr Ser Ala Lys Cys Tyr Ser Gly Thr Ser
        355                 360                 365

Asn Ser Gly Leu Gln Leu Ile Asn Ile Thr Arg His Ser Thr Arg Ile
    370                 375                 380

Val Asp Thr Pro Gly Pro Lys Ile Thr Asn Leu Lys Thr Ile Asn Cys
385                 390                 395                 400

Ile Asn Leu Lys Ala Ser Ile Phe Lys Glu His Arg Glu Val Glu Ile
                405                 410                 415

Asn Val Leu Leu Pro Gln Val Ala Val Asn Leu Ser Asn Cys His Val
            420                 425                 430

Val Ile Lys Ser His Val Cys Asp Tyr Ser Leu Asp Ile Asp Gly Ala
        435                 440                 445

Val Arg Leu Pro His Ile Tyr His Glu Gly Val Phe Ile Pro Gly Thr
    450                 455                 460

Tyr Lys Ile Val Ile Asp Lys Lys Asn Lys Leu Asn Asp Arg Cys Thr
465                 470                 475                 480

Leu Phe Thr Asp Cys Val Ile Lys Gly Arg Glu Val Arg Lys Gly Gln
                485                 490                 495

Ser Val Leu Arg Gln Tyr Lys Thr Glu Ile Arg Ile Gly Lys Ala Ser
            500                 505                 510

Thr Gly Ser Arg Arg Val Leu Ser Glu Glu Pro Ser Asp Asp Cys Ile
        515                 520                 525

Ser Arg Thr Gln Leu Leu Arg Thr Glu Thr Ala Glu Ile His Gly Asp
    530                 535                 540

Asn Tyr Gly Gly Pro Gly Asp Lys Ile Thr Ile Cys Asn Gly Ser Thr
545                 550                 555                 560

Ile Val Asp Gln Arg Leu Gly Ser Glu Leu Gly Cys Tyr Thr Ile Asn
                565                 570                 575

Arg Val Arg Ser Phe Lys Leu Cys Glu Asn Ser Ala Thr Gly Lys Asn
            580                 585                 590

Cys Glu Ile Asp Ser Val Pro Val Lys Cys Arg Gln Gly Tyr Cys Leu
        595                 600                 605

Arg Ile Thr Gln Glu Gly Arg Gly His Val Lys Leu Ser Arg Gly Ser
    610                 615                 620

Glu Val Val Leu Asp Ala Cys Asp Thr Ser Cys Glu Ile Met Ile Pro
625                 630                 635                 640

Lys Gly Thr Gly Asp Ile Leu Val Asp Cys Ser Gly Gly Gln Gln His
                645                 650                 655

Phe Leu Lys Asp Asn Leu Ile Asp Leu Gly Cys Pro Lys Ile Pro Leu
            660                 665                 670

Leu Gly Lys Met Ala Ile Tyr Ile Cys Arg Met Ser Asn His Pro Lys
        675                 680                 685

Thr Thr Met Ala Phe Leu Phe Trp Phe Ser Phe Gly Tyr Val Ile Thr
    690                 695                 700

Cys Ile Leu Cys Lys Ala Ile Phe Tyr Leu Leu Ile Ile Val Gly Thr
705                 710                 715                 720

Leu Gly Lys Arg Leu Lys Gln Tyr Arg Glu Leu Lys Pro Gln Thr Cys
                725                 730                 735
```

```
Thr Ile Cys Glu Thr Thr Pro Val Asn Ala Ile Asp Ala Glu Met His
            740                 745                 750

Asp Leu Asn Cys Ser Tyr Asn Ile Cys Pro Tyr Cys Ala Ser Arg Leu
        755                 760                 765

Thr Ser Asp Gly Leu Ala Arg His Val Ile Gln Cys Pro Lys Arg Lys
    770                 775                 780

Glu Lys Val Glu Thr Glu Leu Tyr Leu Asn Leu Glu Arg Ile Pro
785                 790                 795                 800

Trp Val Val Arg Lys Leu Leu Gln Val Ser Gly Ser Thr Gly Val Ala
                805                 810                 815

Leu Lys Arg Ser Ser Trp Leu Ile Val Leu Leu Val Leu Phe Thr Val
            820                 825                 830

Ser Leu Ser Pro Val Gln Ser Ala Pro Ile Gly Gln Gly Lys Thr Ile
        835                 840                 845

Glu Ala Tyr Arg Ala Arg Glu Gly Tyr Thr Ser Ile Cys Leu Phe Val
    850                 855                 860

Leu Gly Ser Ile Leu Phe Ile Val Ser Cys Leu Met Lys Gly Leu Val
865                 870                 875                 880

Asp Ser Val Gly Asn Ser Phe Phe Pro Gly Leu Ser Ile Cys Lys Thr
                885                 890                 895

Cys Ser Ile Ser Ser Ile Asn Gly Phe Glu Ile Glu Ser His Lys Cys
            900                 905                 910

Tyr Cys Ser Leu Phe Cys Cys Pro Tyr Cys Arg His Cys Ser Thr Asp
        915                 920                 925

Lys Glu Ile His Lys Leu His Leu Ser Ile Cys Lys Lys Arg Lys Lys
    930                 935                 940

Gly Ser Asn Val Met Leu Ala Val Cys Lys Leu Met Cys Phe Arg Ala
945                 950                 955                 960

Thr Met Glu Val Ser Asn Arg Ala Leu Phe Ile Arg Ser Ile Ile Asn
                965                 970                 975

Thr Thr Phe Val Leu Cys Ile Leu Ile Leu Ala Val Cys Val Val Ser
            980                 985                 990

Thr Ser Ala Val Glu Met Glu Asn Leu Pro Ala Gly Thr Trp Glu Arg
        995                 1000                1005

Glu Glu Asp Leu Thr Asn Phe Cys His Gln Glu Cys Gln Val Thr
    1010                1015                1020

Glu Thr Glu Cys Leu Cys Pro Tyr Glu Ala Leu Val Leu Arg Lys
    1025                1030                1035

Pro Leu Phe Leu Asp Ser Thr Ala Lys Gly Met Lys Asn Leu Leu
    1040                1045                1050

Asn Ser Thr Ser Leu Glu Thr Ser Leu Ser Ile Glu Ala Pro Trp
    1055                1060                1065

Gly Ala Ile Asn Val Gln Ser Thr Tyr Lys Pro Thr Val Ser Thr
    1070                1075                1080

Ala Asn Ile Ala Leu Ser Trp Ser Ser Val Glu His Arg Gly Asn
    1085                1090                1095

Lys Ile Leu Val Ser Gly Arg Ser Glu Ser Ile Met Lys Leu Glu
    1100                1105                1110

Glu Arg Thr Gly Ile Ser Trp Asp Leu Gly Val Glu Asp Ala Ser
    1115                1120                1125

Glu Ser Lys Leu Leu Thr Val Ser Val Met Asp Leu Ser Gln Met
    1130                1135                1140

Tyr Ser Pro Val Phe Glu Tyr Leu Ser Gly Asp Arg Gln Val Gly
```

|   |   | 1145 |   |   |   | 1150 |   |   |   | 1155 |   |
|---|---|---|---|---|---|---|---|---|---|---|---|
| Glu | Trp | Pro | Lys | Ala | Thr | Cys | Thr | Gly | Asp | Cys | Pro |
|   |   | 1160 |   |   |   | 1165 |   |   |   | 1170 |   |
| Glu | Arg | Cys |   |   |   |   |   |   |   |   |   |

Glu Trp Pro Lys Ala Thr Cys Thr Gly Asp Cys Pro
         1160              1165              1170
Glu Arg Cys

Gly Cys Thr Ser Ser Thr Cys Leu His Lys Glu Trp
         1175              1180              1185
Pro His Ser

Arg Asn Trp Arg Cys Asn Pro Thr Trp Cys Trp Gly
         1190              1195              1200
Val Gly Thr

Gly Cys Thr Cys Cys Gly Leu Asp Val Lys Asp Leu
         1205              1210              1215
Phe Thr Asp

Tyr Met Phe Val Lys Trp Lys Val Glu Tyr Ile Lys
         1220              1225              1230
Thr Glu Ala

Ile Val Cys Val Glu Leu Thr Ser Gln Glu Arg Gln
         1235              1240              1245
Cys Ser Leu

Ile Glu Ala Gly Thr Arg Phe Asn Leu Gly Pro Val
         1250              1255              1260
Thr Ile Thr

Leu Ser Glu Pro Arg Asn Ile Gln Gln Lys Leu Pro
         1265              1270              1275
Pro Glu Ile

Ile Thr Leu His Pro Arg Ile Glu Glu Gly Phe Phe
         1280              1285              1290
Asp Leu Met

His Val Gln Lys Val Leu Ser Ala Ser Thr Val Cys
         1295              1300              1305
Lys Leu Gln

Ser Cys Thr His Gly Val Pro Gly Asp Leu Gln Val
         1310              1315              1320
Tyr His Ile

Gly Asn Leu Leu Lys Gly Asp Lys Val Asn Gly His
         1325              1330              1335
Leu Ile His

Lys Ile Glu Pro His Phe Asn Thr Ser Trp Met Ser
         1340              1345              1350
Trp Asp Gly

Cys Asp Leu Asp Tyr Tyr Cys Asn Met Gly Asp Trp
         1355              1360              1365
Pro Ser Cys

Thr Tyr Thr Gly Val Thr Gln His Asn His Ala Ser
         1370              1375              1380
Phe Val Asn

Leu Leu Asn Ile Glu Thr Asp Tyr Thr Lys Asn Phe
         1385              1390              1395
His Phe His

Ser Lys Arg Val Thr Ala His Gly Asp Thr Pro Gln
         1400              1405              1410
Leu Asp Leu

Lys Ala Arg Pro Thr Tyr Gly Ala Gly Glu Ile Thr
         1415              1420              1425
Val Leu Val

Glu Val Ala Asp Met Glu Leu His Thr Lys Lys Ile
         1430              1435              1440
Glu Ile Ser

Gly Leu Lys Phe Ala Ser Leu Ala Cys Thr Gly Cys
         1445              1450              1455
Tyr Ala Cys

Ser Ser Gly Ile Ser Cys Lys Val Arg Ile His Val
         1460              1465              1470
Asp Glu Pro

Asp Glu Leu Thr Val His Val Lys Ser Asp Asp Pro
         1475              1480              1485
Asp Val Val

Ala Ala Ser Ser Ser Leu Met Ala Arg Lys Leu Glu
         1490              1495              1500
Phe Gly Thr

Asp Ser Thr Phe Lys Ala Phe Ser Ala Met Pro Lys
         1505              1510              1515
Thr Ser Leu

Cys Phe Tyr Ile Val Glu Arg Glu His Cys Lys Ser
         1520              1525              1530
Cys Ser Glu

Glu Asp Thr Lys Lys Cys Val Asn Thr Lys Leu Glu
         1535              1540              1545
Gln Pro Gln

-continued

```
Ser Ile Leu Ile Glu His Lys Gly Thr Ile Ile Gly Lys Gln Asn
    1550                1555                1560

Ser Thr Cys Thr Ala Lys Ala Ser Cys Trp Leu Glu Ser Val Lys
    1565                1570                1575

Ser Phe Phe Tyr Gly Leu Lys Asn Met Leu Ser Gly Ile Phe Gly
    1580                1585                1590

Asn Val Phe Met Gly Ile Phe Leu Phe Leu Ala Pro Phe Ile Leu
    1595                1600                1605

Leu Ile Leu Phe Phe Met Phe Gly Trp Arg Ile Leu Phe Cys Phe
    1610                1615                1620

Lys Cys Cys Arg Arg Thr Arg Gly Leu Phe Lys Tyr Arg His Arg
    1625                1630                1635

Lys Asp Asp Glu Glu Thr Gly Tyr Arg Gln Ile Ile Glu Lys Leu
    1640                1645                1650

Asn Asn Lys Lys Gly Lys Asn Lys Leu Leu Asp Gly Glu Arg Leu
    1655                1660                1665

Ala Asp
    1670

<210> SEQ ID NO 8
<211> LENGTH: 1684
<212> TYPE: PRT
<213> ORGANISM: Artificial Sequence
<220> FEATURE:
<223> OTHER INFORMATION: Recombinant Protein

<400> SEQUENCE: 8

Met His Ile Ser Leu Met Tyr Ala Ile Leu Cys Leu Gln Leu Cys Gly
1               5                   10                  15

Leu Gly Glu Thr His Gly Ser His Asn Glu Thr Arg His Asn Lys Thr
                20                  25                  30

Asp Thr Met Thr Thr Pro Gly Asp Asn Pro Ser Ser Glu Pro Pro Val
            35                  40                  45

Ser Thr Ala Leu Ser Ile Thr Leu Asp Pro Ser Thr Val Thr Pro Thr
        50                  55                  60

Thr Pro Ala Ser Gly Leu Glu Gly Ser Gly Glu Val Tyr Thr Ser Pro
65                  70                  75                  80

Pro Ile Thr Thr Gly Ser Leu Pro Leu Ser Glu Thr Thr Pro Glu Leu
                85                  90                  95

Pro Val Thr Thr Gly Thr Asp Thr Leu Ser Ala Gly Asp Val Asp Pro
            100                 105                 110

Ser Thr Gln Thr Ala Gly Gly Thr Ser Ala Pro Thr Val Arg Thr Ser
        115                 120                 125

Leu Pro Asn Ser Pro Ser Thr Pro Ser Thr Pro Gln Asp Thr His His
    130                 135                 140

Pro Val Arg Asn Leu Leu Ser Val Thr Ser Pro Gly Pro Asp Glu Thr
145                 150                 155                 160

Ser Thr Pro Ser Gly Thr Gly Lys Glu Ser Ser Ala Thr Ser Ser Pro
                165                 170                 175

His Pro Val Ser Asn Arg Pro Thr Pro Ala Thr Ala Gln Gly
            180                 185                 190

Pro Thr Glu Asn Asp Ser His Asn Ala Thr Glu His Pro Glu Ser Leu
        195                 200                 205

Thr Gln Ser Ala Thr Pro Gly Leu Met Thr Ser Pro Thr Gln Ile Val
    210                 215                 220
```

-continued

His Pro Gln Ser Ala Thr Pro Ile Thr Val Gln Asp Thr His Pro Ser
225                 230                 235                 240

Pro Thr Asn Arg Ser Lys Arg Asn Leu Lys Met Glu Ile Ile Leu Thr
            245                 250                 255

Leu Ser Gln Gly Leu Lys Lys Tyr Tyr Gly Lys Ile Leu Arg Leu Leu
        260                 265                 270

Gln Leu Thr Leu Glu Glu Asp Thr Glu Gly Leu Leu Glu Trp Cys Lys
    275                 280                 285

Arg Asn Leu Gly Leu Asp Cys Asp Asp Thr Phe Phe Gln Lys Arg Ile
290                 295                 300

Glu Glu Phe Phe Ile Thr Gly Glu Gly His Phe Asn Glu Val Leu Gln
305                 310                 315                 320

Phe Arg Thr Pro Gly Thr Leu Ser Thr Thr Glu Ser Thr Pro Ala Gly
                325                 330                 335

Leu Pro Thr Ala Glu Pro Phe Lys Ser Tyr Phe Ala Lys Gly Phe Leu
            340                 345                 350

Ser Ile Asp Ser Gly Tyr Tyr Ser Ala Lys Cys Tyr Ser Gly Thr Ser
        355                 360                 365

Asn Ser Gly Leu Gln Leu Ile Asn Ile Thr Arg His Ser Thr Arg Ile
370                 375                 380

Val Asp Thr Pro Gly Pro Lys Ile Thr Asn Leu Lys Thr Ile Asn Cys
385                 390                 395                 400

Ile Asn Leu Lys Ala Ser Ile Phe Lys Glu His Arg Glu Val Glu Ile
                405                 410                 415

Asn Val Leu Leu Pro Gln Val Ala Val Asn Leu Ser Asn Cys His Val
            420                 425                 430

Val Ile Lys Ser His Val Cys Asp Tyr Ser Leu Asp Ile Asp Gly Ala
        435                 440                 445

Val Arg Leu Pro His Ile Tyr His Glu Gly Val Phe Ile Pro Gly Thr
450                 455                 460

Tyr Lys Ile Val Ile Asp Lys Lys Asn Lys Leu Asn Asp Arg Cys Thr
465                 470                 475                 480

Leu Phe Thr Asp Cys Val Ile Lys Gly Arg Glu Val Arg Lys Gly Gln
                485                 490                 495

Ser Val Leu Arg Gln Tyr Lys Thr Glu Ile Arg Ile Gly Lys Ala Ser
            500                 505                 510

Thr Gly Ser Arg Arg Leu Leu Ser Glu Glu Pro Ser Asp Asp Cys Ile
        515                 520                 525

Ser Arg Thr Gln Leu Leu Arg Thr Glu Thr Ala Glu Ile His Gly Asp
530                 535                 540

Asn Tyr Gly Gly Pro Gly Asp Lys Ile Thr Ile Cys Asn Gly Ser Thr
545                 550                 555                 560

Ile Val Asp Gln Arg Leu Gly Ser Glu Leu Gly Cys Tyr Thr Ile Asn
                565                 570                 575

Arg Val Arg Ser Phe Lys Leu Cys Glu Asn Ser Ala Thr Gly Lys Asn
            580                 585                 590

Cys Glu Ile Asp Ser Val Pro Val Lys Cys Arg Gln Gly Tyr Cys Leu
        595                 600                 605

Arg Ile Thr Gln Glu Gly Arg Gly His Val Lys Leu Ser Arg Gly Ser
610                 615                 620

Glu Val Val Leu Asp Ala Cys Asp Thr Ser Cys Glu Ile Met Ile Pro
625                 630                 635                 640

-continued

```
Lys Gly Thr Gly Asp Ile Leu Val Asp Cys Ser Gly Gln Gln His
            645                 650                 655

Phe Leu Lys Asp Asn Leu Ile Asp Leu Gly Cys Pro Lys Ile Pro Leu
        660                 665                 670

Leu Gly Lys Met Ala Ile Tyr Ile Cys Arg Met Ser Asn His Pro Lys
        675                 680                 685

Thr Thr Met Ala Phe Leu Phe Trp Phe Ser Phe Gly Tyr Val Ile Thr
    690                 695                 700

Cys Ile Leu Cys Lys Ala Ile Phe Tyr Leu Leu Ile Ile Val Gly Thr
705                 710                 715                 720

Leu Gly Lys Arg Leu Lys Gln Tyr Arg Glu Leu Lys Pro Gln Thr Cys
        725                 730                 735

Thr Ile Cys Glu Thr Thr Pro Val Asn Ala Ile Asp Ala Glu Met His
        740                 745                 750

Asp Leu Asn Cys Ser Tyr Asn Ile Cys Pro Tyr Cys Ala Ser Arg Leu
        755                 760                 765

Thr Ser Asp Gly Leu Ala Arg His Val Ile Gln Cys Pro Lys Arg Lys
    770                 775                 780

Glu Lys Val Glu Glu Thr Glu Leu Tyr Leu Asn Leu Glu Arg Ile Pro
785                 790                 795                 800

Trp Val Val Arg Lys Leu Leu Gln Val Ser Glu Ser Thr Gly Val Ala
                805                 810                 815

Leu Lys Arg Ser Ser Trp Leu Ile Val Leu Leu Val Leu Phe Thr Val
            820                 825                 830

Ser Leu Ser Pro Val Gln Ser Ala Pro Ile Gly Gln Gly Lys Thr Ile
        835                 840                 845

Glu Ala Tyr Arg Ala Arg Glu Gly Tyr Thr Ser Ile Cys Leu Phe Val
    850                 855                 860

Leu Gly Ser Ile Leu Phe Ile Val Ser Cys Leu Met Lys Gly Leu Val
865                 870                 875                 880

Asp Ser Val Gly Asn Ser Phe Phe Pro Gly Leu Ser Ile Cys Lys Thr
                885                 890                 895

Cys Ser Ile Ser Ser Ile Asn Gly Phe Glu Ile Glu Ser His Lys Cys
        900                 905                 910

Tyr Cys Ser Leu Phe Cys Cys Pro Tyr Cys Arg His Cys Ser Thr Asp
    915                 920                 925

Lys Glu Ile His Lys Leu His Leu Ser Ile Cys Lys Lys Arg Lys Lys
        930                 935                 940

Gly Ser Asn Val Met Leu Ala Val Cys Lys Leu Met Cys Phe Arg Ala
945                 950                 955                 960

Thr Met Glu Val Ser Asn Arg Ala Leu Phe Ile Arg Ser Ile Ile Asn
                965                 970                 975

Thr Thr Phe Val Leu Cys Ile Leu Ile Leu Ala Val Cys Val Val Ser
            980                 985                 990

Thr Ser Ala Val Glu Met Glu Asn Leu Pro Ala Gly Thr Trp Glu Arg
        995                 1000                1005

Glu Glu Asp Leu Thr Asn Phe Cys His Gln Glu Cys Gln Val Thr
        1010                1015                1020

Glu Thr Glu Cys Leu Cys Pro Tyr Glu Ala Leu Val Leu Arg Lys
        1025                1030                1035

Pro Leu Phe Leu Asp Ser Thr Ala Lys Gly Met Lys Asn Leu Leu
        1040                1045                1050

Asn Ser Thr Ser Leu Glu Thr Ser Leu Ser Ile Glu Ala Pro Trp
```

```
            1055                1060                1065

Gly Ala Ile Asn Val Gln Ser Thr Tyr Lys Pro Thr Val Ser Thr
            1070                1075                1080

Ala Asn Ile Ala Leu Ser Trp Ser Ser Val Glu His Arg Gly Asn
            1085                1090                1095

Lys Ile Leu Val Ser Gly Arg Ser Glu Ser Ile Met Lys Leu Glu
            1100                1105                1110

Glu Arg Thr Gly Ile Ser Trp Asp Leu Gly Val Glu Asp Ala Ser
            1115                1120                1125

Glu Ser Lys Leu Leu Thr Val Ser Val Met Asp Leu Ser Gln Met
            1130                1135                1140

Tyr Ser Pro Val Phe Glu Tyr Leu Ser Gly Asp Arg Gln Val Gly
            1145                1150                1155

Glu Trp Pro Lys Ala Thr Cys Thr Gly Asp Cys Pro Glu Arg Cys
            1160                1165                1170

Gly Cys Thr Ser Ser Thr Cys Leu His Lys Glu Trp Pro His Ser
            1175                1180                1185

Arg Asn Trp Arg Cys Asn Pro Thr Trp Cys Trp Gly Val Gly Thr
            1190                1195                1200

Gly Cys Thr Cys Cys Gly Leu Asp Val Lys Asp Leu Phe Thr Asp
            1205                1210                1215

Tyr Met Phe Val Lys Trp Lys Val Glu Tyr Ile Lys Thr Glu Ala
            1220                1225                1230

Ile Val Cys Val Glu Leu Thr Ser Gln Glu Arg Gln Cys Ser Leu
            1235                1240                1245

Ile Glu Ala Gly Thr Arg Phe Asn Leu Gly Pro Val Thr Ile Thr
            1250                1255                1260

Leu Ser Glu Pro Arg Asn Ile Gln Gln Lys Leu Pro Pro Glu Ile
            1265                1270                1275

Ile Thr Leu His Pro Arg Ile Glu Glu Gly Phe Phe Asp Leu Met
            1280                1285                1290

His Val Gln Lys Val Leu Ser Ala Ser Thr Val Cys Lys Leu Gln
            1295                1300                1305

Ser Cys Thr His Gly Val Pro Gly Asp Leu Gln Val Tyr His Ile
            1310                1315                1320

Gly Asn Leu Leu Lys Gly Asp Lys Val Asn Gly His Leu Ile His
            1325                1330                1335

Lys Ile Glu Pro His Phe Asn Thr Ser Trp Met Ser Trp Asp Gly
            1340                1345                1350

Cys Asp Leu Asp Tyr Tyr Cys Asn Met Gly Asp Trp Pro Ser Cys
            1355                1360                1365

Thr Tyr Thr Gly Val Thr Gln His Asn His Ala Ser Phe Val Asn
            1370                1375                1380

Leu Leu Asn Ile Glu Thr Asp Tyr Thr Lys Asn Phe His Phe His
            1385                1390                1395

Ser Lys Arg Val Thr Ala His Gly Asp Thr Pro Gln Leu Asp Leu
            1400                1405                1410

Lys Ala Arg Pro Thr Tyr Gly Ala Gly Glu Ile Thr Val Leu Val
            1415                1420                1425

Glu Val Ala Asp Met Glu Leu His Thr Lys Lys Ile Glu Ile Ser
            1430                1435                1440

Gly Leu Lys Phe Ala Ser Leu Ala Cys Thr Gly Cys Tyr Ala Cys
            1445                1450                1455
```

| Ser | Ser | Gly | Ile | Ser | Cys | Lys | Val | Arg | Ile | His | Val | Asp | Glu | Pro |
|-----|-----|-----|-----|-----|-----|-----|-----|-----|-----|-----|-----|-----|-----|-----|
| 1460 | | | | 1465 | | | | | 1470 | | | | | |

Asp Glu Leu Thr Val His Val Lys Ser Asp Asp Pro Asp Val Val
1475            1480              1485

Ala Ala Ser Ser Ser Leu Met Ala Arg Lys Leu Glu Phe Gly Thr
1490            1495              1500

Asp Ser Thr Phe Lys Ala Phe Ser Ala Met Pro Lys Thr Ser Leu
1505            1510              1515

Cys Phe Tyr Ile Val Glu Arg Glu His Cys Lys Ser Cys Ser Glu
1520            1525              1530

Glu Asp Thr Lys Lys Cys Val Asn Thr Lys Leu Glu Gln Pro Gln
1535            1540              1545

Ser Ile Leu Ile Glu His Lys Gly Thr Ile Ile Gly Lys Gln Asn
1550            1555              1560

Ser Thr Cys Thr Ala Lys Ala Ser Cys Trp Leu Glu Ser Val Lys
1565            1570              1575

Ser Phe Phe Tyr Gly Leu Lys Asn Met Leu Ser Gly Ile Phe Gly
1580            1585              1590

Asn Val Phe Met Gly Ile Phe Leu Phe Leu Ala Pro Phe Ile Leu
1595            1600              1605

Leu Ile Leu Phe Phe Met Phe Gly Trp Arg Ile Leu Phe Cys Phe
1610            1615              1620

Lys Cys Cys Arg Arg Thr Arg Gly Leu Phe Lys Tyr Arg His Leu
1625            1630              1635

Lys Asp Asp Glu Glu Thr Gly Tyr Arg Arg Ile Ile Glu Lys Leu
1640            1645              1650

Asn Asn Lys Lys Gly Lys Asn Lys Leu Leu Asp Gly Glu Arg Leu
1655            1660              1665

Ala Asp Arg Arg Ile Ala Glu Leu Phe Ser Thr Lys Thr His Ile
1670            1675              1680

Gly

<210> SEQ ID NO 9
<211> LENGTH: 9853
<212> TYPE: DNA
<213> ORGANISM: Artificial Sequence
<220> FEATURE:
<223> OTHER INFORMATION: Recombinant DNA

<400> SEQUENCE: 9
gacgaagaca aacaaaccat tattatcatt aaaaggctca ggagaaactt taacagtaat     60
caaaatgtct gttacagtca agagaatcat tgacaacaca gtcgtagttc caaaacttcc    120
tgcaaatgag gatccagtgg aatacccggc agattacttc agaaaatcaa aggagattcc    180
tctttacatc aatactacaa aaagtttgtc agatctaaga ggatatgtct accaaggcct    240
caaatccgga aatgtatcaa tcatacatgt caacagctac ttgtatggag cattaaagga    300
catccggggt aagttggata agattggtc aagtttcgga ataaacatcg ggaaagcagg    360
ggatacaatc ggaatatttg accttgtatc cttgaaagcc ctggacggcg tacttccaga    420
tggagtatcg gatgcttcca gaaccagcgc agatgacaaa tggttgcctt gtatctact    480 tggcttatac agagtgggca gaacacaaat gcctgaatac agaaaaaagc tcatggatgg    540
gctgacaaat caatgcaaaa tgatcaatga acagttgaa cctcttgtgc agaaggtcg    600 tgacattttt gatgtgtggg gaaatgacag taattacaca aaaattgtcg ctgcagtgga    660

```
catgttcttc cacatgttca aaaaacatga atgtgcctcg ttcagatacg gaactattgt      720
ttccagattc aaagattgtg ctgcattggc aacatttgga cacctctgca aaataaccgg      780
aatgtctaca gaagatgtaa cgacctggat cttgaaccga gaagttgcag atgaaatggt      840
ccaaatgatg cttccaggcc aagaaattga caaggccgat tcatacatgc cttatttgat      900
cgactttgga ttgtcttcta agtctccata ttcttccgtc aaaaaccctg ccttccactt      960
ctgggggcaa ttgacagctc ttctgctcag atccaccaga gcaaggaatg cccgacagcc     1020
tgatgacatt gagtatacat ctcttactac agcaggtttg ttgtacgctt atgcagtagg     1080
atcctctgcc gacttggcac aacagttttg tgttggagat aacaaataca ctccagatga     1140
tagtaccgga ggattgacga ctaatgcacc gccacaaggc agagatgtgg tcgaatggct     1200
cggatggttt gaagatcaaa acagaaaacc gactcctgat atgatgcagt atgcgaaaag     1260
agcagtcatg tcactgcaag gcctaagaga aagacaatt ggcaagtatg ctaagtcaga     1320
atttgacaaa tgaccctata attctcagat cacctattat atattatgct acatatgaaa     1380
aaaactaaca gatatcatgg ataatctcac aaaagttcgt gagtatctca gtcctattc     1440 tcgtctggat caggcggtag gagagataga tgagatcgaa gcacaacgag ctgaaaagtc     1500
caattatgag ttgttccaag aggatggagt ggaagagcat actaagccct cttattttca     1560
ggcagcagat gattctgaca cagaatctga accagaaatt gaagacaatc aaggcttgta     1620
tgcaccagat ccagaagctg agcaagttga aggctttata caggggcctt tagatgacta     1680
tgcagatgag gaagtggatg ttgtatttac ttcggactgg aaacagcctg agcttgaatc     1740
tgacgagcat ggaaagacct tacggttgac atcgccagag ggtttaagtg gagagcagaa     1800
atcccagtgg ctttcgacga ttaaagcagt cgtgcaaagt gccaaatact ggaatctggc     1860
agagtgcaca tttgaagcat cgggagaagg ggtcattatg aaggagcgcc agataactcc     1920
ggatgtatat aaggtcactc cagtgatgaa cacacatccg tcccaatcag aagcagtatc     1980
agatgtttgg tctctctcaa agacatccat gactttccaa cccaagaaag caagtcttca     2040
gcctctcacc atatccttgg atgaattgtt ctcatctaga ggagagttca tctctgtcgg     2100
aggtgacgga cgaatgtctc ataaagaggc catcctgctc ggcctgagat acaaaaagtt     2160
gtacaatcag gcgagagtca atattctct gtagactatg aaaaaaagta acagatatca     2220
cgatctaagt gtcatcccaa tccattcatc atgagttcct taaagaagat tctcggtctg     2280
aaggggaaag gtaagaaatc taagaaatta gggatcgcac cacccccta tgaagaggac     2340 actagcatga agtatgctcc gagcgctcca attgacaaat cctatttgg agttgacgag     2400 atggacacct atgatccgaa tcaattaaga tatgagaaat tcttctttac agtgaaaatg     2460
acggttagat ctaatcgtcc gttcagaaca tactcagatg tggcagccgc tgtatcccat     2520
tgggatcaca tgtacatcgg aatggcaggg aaacgtccct tctacaaaat cttggctttt     2580
ttgggttctt ctaatctaaa ggccactcca gcggtattgg cagatcaagg tcaaccagag     2640
tatcacgctc actgcgaagg cagggcttat ttgccacata ggatggggaa gaccccctccc     2700 atgctcaatg taccagagca cttcagaaga ccattcaata taggtctta caagggaacg     2760 attgagctca caatgaccat ctacgatgat gagtcactgg aagcagctcc tatgatctgg     2820
gatcatttca attcttccaa attttctgat ttcagagaga aggccttaat gtttggcctg     2880
attgtcgaga aaaaggcatc tggagcgtgg gtcctggact ctatcggcca cttcaaatga     2940
gctagtctaa cttctagctt ctgaacaatc cccggtttac tcagtctccc ctaattccag     3000
```

```
cctctcgaac aactaatatc ctgtcttttc tatccctatg aaaaaaacta acagagatcg   3060
atctgtttac cagattcttc atgtttggac caaatcaact tgtgatacca tgctcaaaga   3120
ggcctcaatt atatttgagt ttttaatttt tatgaaaaaa actaacagca atcatggaag   3180
tccacgattt tgagaccgac gagttcaatg atttcaatga agatgactat gccacaagag   3240
aattcctgaa tcccgatgag cgcatgacgt acttgaatca tgctgattac aacctgaatt   3300
ctcctctaat tagtgatgat attgacaatt taatcaggaa attcaattct cttccaattc   3360
cctcgatgtg ggatagtaag aactgggatg gagttcttga gatgttaaca tcatgtcaag   3420
ccaatcccat ctcaacatct cagatgcata aatggatggg aagttggtta atgtctgata   3480
atcatgatgc cagtcaaggg tatagttttt tacatgaagt ggacaaagag gcagaaataa   3540
catttgacgt ggtggagacc ttcatccgcg gctggggcaa caaaccaatt gaatacatca   3600
aaaaggaaag atggactgac tcattcaaaa ttctcgctta tttgtgtcaa aagttttgg    3660 acttacacaa gttgacatta atcttaaatg ctgtctctga ggtggaattg ctcaacttgg   3720
cgaggacttt caaaggcaaa gtcagaagaa gttctcatgg aacgaacata tgcaggatta   3780
gggttcccag cttgggtcct acttttattt cagaaggatg ggcttacttc aagaaacttg   3840
atattctaat ggaccgaaac tttctgttaa tggtcaaaga tgtgattata gggaggatgc   3900
aaacggtgct atccatggta tgtagaatag acaacctgtt ctcagagcaa gacatcttct   3960
cccttctaaa tatctacaga attggagata aaattgtgga gaggcaggga aattttctt    4020 atgacttgat taaatggtg gaaccgatat gcaacttgaa gctgatgaaa ttagcaagag   4080
aatcaaggcc tttagtccca caattccctc attttgaaaa tcatatcaag acttctgttg   4140 atgaagggc aaaaattgac cgaggtataa gattcctcca tgatcagata atgagtgtga   4200
aaacagtgga tctcacactg gtgatttatg gatcgttcag acattgggt catccttta   4260 tagattatta cactggacta gaaaaattac attcccaagt aaccatgaag aaagatattg   4320
atgtgtcata tgcaaaagca cttgcaagtg atttagctcg gattgttcta tttcaacagt   4380
tcaatgatca taaaaagtgg ttcgtgaatg gagacttgct ccctcatgat catcccttta   4440
aaagtcatgt taaagaaaat acatggccca cagctgctca agttcaagat tttggagata   4500
aatggcatga acttccgctg attaaatgtt ttgaaatacc cgacttacta gacccatcga   4560
taatatactc tgacaaaagt cattcaatga ataggtcaga ggtgttgaaa catgtccgaa   4620
tgaatccgaa cactcctatc cctagtaaaa aggtgttgca gactatgttg gacacaaagg   4680
ctaccaattg gaaagaattt cttaaagaga ttgatgagaa gggcttagat gatgatgatc   4740
taattattgg tcttaaagga aaggagaggg aactgaagtt ggcaggtaga ttttctccc    4800 taatgtcttg gaaattgcga gaatactttg taattaccga atatttgata aagactcatt   4860
tcgtccctat gtttaaaggc ctgacaatgg cggacgatct aactgcagtc attaaaaaga   4920
tgttagattc ctcatccggc caaggattga agtcatatga ggcaatttgc atagccaatc   4980
acattgatta cgaaaaatgg aataaccacc aaaggaagtt atcaaacggc ccagtgttcc   5040
gagttatggg ccagttctta ggttatccat ccttaatcga gagaactcat gaatttttg    5100 agaaaagtct tatatactac aatggaagac cagacttgat gcgtgttcac aacaacacac   5160
tgatcaattc aacctcccaa cgagtttgtt ggcaaggaca gagggtgga ctggaaggtc    5220 tacggcaaaa aggatggagt atcctcaatc tactggttat tcaaagagag gctaaaatca   5280
gaaacactgc tgtcaaagtc ttggcacaag gtgataatca agttatttgc acacagtata   5340
aaacgaagaa atcgagaaac gttgtagaat tacagggtgc tctcaatcaa atggtttcta   5400
```

```
ataatgagaa aattatgact gcaatcaaaa tagggacagg gaagttagga cttttgataa    5460
atgacgatga gactatgcaa tctgcagatt acttgaatta tggaaaaata ccgatttttcc   5520 gtggagtgat tagagggtta gagaccaaga gatggtcacg agtgacttgt gtcaccaatg    5580
accaaatacc cacttgtgct aatataatga gctcagtttc cacaaatgct ctcaccgtag    5640
ctcattttgc tgagaaccca atcaatgcca tgatacagta caattatttt gggacatttg    5700
ctagactctt gttgatgatg catgatcctg ctcttcgtca atcattgtat gaagttcaag    5760
ataagatacc gggcttgcac agttctactt tcaaatacgc catgttgtat ttggacccctt   5820 ccattggagg agtgtcgggc atgtctttgt ccaggttttt gattagagcc ttcccagatc    5880
ccgtaacaga aagtctctca ttctggagat tcatccatgt acatgctcga agtgagcatc    5940
tgaaggagat gagtgcagta tttggaaacc ccgagatagc caagtttcga ataactcaca    6000
tagacaagct agtagaagat ccaacctctc tgaacatcgc tatgggaatg agtccagcga    6060
acttgttaaa gactgaggtt aaaaaatgct taatcgaatc aagacaaacc atcaggaacc    6120
aggtgattaa ggatgcaacc atatatttgt atcatgaaga ggatcggctc agaagtttct    6180
tatggtcaat aaatcctctg ttccctagat ttttaagtga attcaaatca ggcacttttt    6240
tgggagtcgc agacgggctc atcagtctat ttcaaaattc tcgtactatt cggaactcct    6300
ttaagaaaaa gtatcatagg gaattggatg atttgattgt gaggagtgag gtatcctctt    6360
tgacacattt agggaaactt catttgagaa ggggatcatg taaaatgtgg acatgttcag    6420
ctactcatgc tgacacatta agatacaaat cctggggccg tacagttatt gggacaactg    6480
taccccatcc attagaaatg ttgggtccac aacatcgaaa agagactcct tgtgcaccat    6540
gtaacacatc agggttcaat tatgtttctg tgcattgtcc agacgggatc catgacgtct    6600
ttagttcacg gggaccattg cctgcttatc tagggtctaa aacatctgaa tctacatcta    6660
ttttgcagcc ttgggaaagg gaaagcaaag tcccactgat taaaagagct acacgtctta    6720
gagatgctat ctcttggttt gttgaacccg actctaaact agcaatgact atactttcta    6780
acatccactc tttaacaggc gaagaatgga ccaaaaggca gcatgggttc aaaagaacag    6840
ggtctgccct tcataggttt tcgacatctc ggatgagcca tggtgggttc gcatctcaga    6900
gcactgcagc attgaccagg ttgatggcaa ctacagacac catgagggat ctgggagatc    6960
agaatttcga cttttttattc caagcaacgt tgctctatgc tcaaattacc accactgttg    7020
caagagacgg atggatcacc agttgtacag atcattatca tattgcctgt aagtcctgtt    7080
tgagacccat agaagagatc accctggact caagtatgga ctacacgccc ccagatgtat    7140
cccatgtgct gaagacatgg aggaatgggg aaggttcgtg gggacaagag ataaaacaga    7200
tctatccttt agaagggaat tggaagaatt tagcacctgc tgagcaatcc tatcaagtcg    7260
gcagatgtat aggttttcta tatggagact ggcgtatag aaaatctact catgccgagg    7320
acagttctct atttcctcta tctatacaag gtcgtattag aggtcgaggt ttcttaaaag    7380
ggttgctaga cggattaatg agagcaagtt gctgccaagt aatacaccgg agaagtctgg    7440
ctcatttgaa gaggccggcc aacgcagtgt acggaggttt gatttacttg attgataaat    7500
tgagtgtatc acctccattc ctttctctta ctagatcagg acctattaga gacgaattag    7560
aaacgattcc ccacaagatc ccaacctcct atccgacaag caaccgtgat atgggggtga    7620
ttgtcagaaa ttacttcaaa taccaatgcc gtctaattga aaagggaaaa tacagatcac    7680
attattcaca attatggtta ttctcagatg tcttatccat agacttcatt ggaccattct    7740
```

```
ctatttccac cacccctcttg caaatcctat acaagccatt tttatctggg aaagataaga    7800
atgagttgag agagctggca aatctttctt cattgctaag atcaggagag gggtggggaag   7860
acatacatgt gaaattcttc accaaggaca tattattgtg tccagaggaa atcagacatg    7920
cttgcaagtt cgggattgct aaggataata ataaagacat gagctatccc ccttggggaa    7980
gggaatccag agggacaatt acaacaatcc ctgtttatta tacgaccacc ccttacccaa    8040
agatgctaga gatgcctcca agaatcccaaa atccccctgct gtccggaatc aggttgggcc   8100
aattaccaac tggcgctcat tataaaattc ggagtatatt acatggaatg gaatccatt     8160
acagggactt cttgagttgt ggagacggct ccggagggat gactgctgca ttactacgag    8220
aaaatgtgca tagcagagga atattcaata gtctgttaga attatcaggg tcagtcatgc    8280
gaggcgcctc tcctgagccc cccagtgccc tagaaacttt aggaggagat aaatcgagat    8340
gtgtaaatgg tgaaacatgt tgggaatatc catctgactt atgtgaccca aggacttggg   8400
actatttcct ccgactcaaa gcaggcttgg ggcttcaaat tgatttaatt gtaatggata    8460
tggaagttcg ggattcttct actagcctga aaattgagac gaatgttaga aattatgtgc    8520
accggatttt ggatgagcaa ggagttttaa tctacaagac ttatgaaaca tatatttgtg    8580
agagcgaaaa gaatgcagta acaatccttg gtcccatgtt caagacggtc gacttagttc    8640
aaacagaatt tagtagttct caaacgtctg aagtatatat ggtatgtaaa ggtttgaaga    8700
aattaatcga tgaacccaat cccgattggt cttccatcaa tgaatcctgg aaaaacctgt    8760
acgcattcca gtcatcagaa caggaatttg ccagagcaaa gaaggttagt acatacttta    8820
ccttgacagg tattccctcc caattcattc ctgatccttt tgtaaacatt gagactatgc    8880
tacaaatatt cggagtaccc acgggtgtgt ctcatgcggc tgccttaaaa tcatctgata    8940
gacctgcaga tttattgacc attagccttt tttatatggc gattatatcg tattataaca    9000
tcaatcatat cagagtagga ccgatacctc cgaaccccccc atcagatgga attgcacaaa    9060
atgtgggat cgctataact ggtataagct tttggctgag tttgatggag aaagacattc    9120
cactatatca acagtgttta gcagttatcc agcaatcatt cccgattagg tgggaggctg    9180
tttcagtaaa aggaggatac aagcagaagt ggagtactag aggtgatggg ctcccaaaag    9240
atacccgaat ttcagactcc ttggccccaa tcgggaactg gatcagatct ctggaattgg    9300
tccgaaacca agttcgtcta aatccattca atgagatctt gttcaatcag ctatgtcgta    9360
cagtggataa tcatttgaaa tggtcaaatt tgcgaagaaa cacaggaatg attgaatgga    9420
tcaatagacg aatttcaaaa gaagaccggt ctatactgat gttgaagagt gacctacacg    9480
aggaaaactc ttggagagat taaaaaatca tgaggagact ccaaacttta agtatgaaaa    9540
aaactttgat ccttaagacc ctcttgtggt tttattttt tatctggttt tgtggtcttc     9600
gtgggtcggc atggcatctc cacctcctcg cggtccgacc tgggcatccg aaggaggacg    9660
tcgtccactc ggatggctaa gggaggggcc cccgcggggc tgctaacaaa gcccgaaagg    9720
aagctgagtt ggctgctgcc accgctgagc aataactagc ataaccccctt ggggcctcta  9780
aacgggtctt gagggggtttt ttgctgaaag gaggaactat atccggatcg agacctcgat    9840
actagtgagc tcc                                                      9853
```

<210> SEQ ID NO 10
<211> LENGTH: 9853
<212> TYPE: DNA
<213> ORGANISM: Artificial Sequence
<220> FEATURE:
<223> OTHER INFORMATION: Recombinant DNA

<400> SEQUENCE: 10

```
gacgaagaca aacaaaccat tattatcatt aaaaggctca ggagaaactt taacagtaat    60
caaaatgtct gttacagtca agagaatcat tgacaacaca gtcatagttc caaaacttcc   120
tgcaaatgag gatccagtgg aatacccggc agattacttc agaaaatcaa aggagattcc   180
tctttacatc aatactacaa aaagtttgtc agatctaaga ggatatgtct accaaggcct   240
caaatccgga aatgtatcaa tcatacatgt caacagctac ttgtatggag cattaaagga   300
catccggggt aagttggata agattggtc aagtttcgga ataaacatcg ggaaagcagg    360
ggatacaatc ggaatatttg accttgtatc cttgaaagcc ctggacggcg tacttccaga   420
tggagtatcg gatgcttcca gaaccagcgc agatgacaaa tggttgcctt tgtatctact   480
tggcttatac agagtgggca gaacacaaat gcctgaatac agaaaaaagc tcatggatgg   540
gctgacaaat caatgcaaaa tgatcaatga acagtttgaa cctcttgtgc agaaggtcg    600
tgacattttt gatgtgtggg gaaatgacag taattacaca aaaattgtcg ctgcagtgga   660
catgttcttc cacatgttca aaaacatga atgtgcctcg ttcagatacg gaactattgt    720
ttccagattc aaagattgtg ctgcattggc aacatttgga cacctctgca aaataaccgg   780
aatgtctaca gaagatgtaa cgacctggat cttgaaccga gaagttgcag atgaaatggt   840
ccaaatgatg cttccaggcc aagaaattga caaggccgat tcatacatgc cttatttgat   900
cgactttgga ttgtcttcta agtctccata ttcttccgtc aaaaaccctg ccttccactt   960
ctggggcaa ttgacagctc ttctgctcag atccaccaga gcaaggaatg cccgacagcc   1020
tgatgacatt gagtatacat ctcttactac agcaggtttg ttgtacgctt atgcagtagg  1080
atcctctgcc gacttggcac aacagttttg tgttggagat aacaaataca ctccagatga  1140
tagtaccgga ggattgacga ctaatgcacc gccacaaggc agagatgtgg tcgaatggct  1200
cggatggttt gaagatcaaa acagaaaacc gactcctgat atgatgcagt atgcgaaaag  1260
agcagtcatg tcactgcaag gcctaagaga aagacaatt ggcaagtatg ctaagtcaga   1320
atttgacaaa tgaccctata attctcagat cacctattat atattatgct acatatgaaa  1380
aaaactaaca gatatcatgg ataatctcac aaaagttcgt gagtatctca agtcctattc  1440
tcgtctggat caggcggtag gagagataga tgagatcgaa gcacaacgag ctgaaaagtc  1500
caattatgag ttgttccaag aggatggagt ggaagagcat actaagccct cttattttca  1560
ggcagcagat gattctgaca cagaatctga accagaaatt gaagacaatc aaggtttgta  1620
tgcacaggat ccagaagctg agcaagttga aggctttata caggggcctt tagatgacta  1680
tgcagatgag gaagtggatg ttgtatttac ttcggactgg aaaccacctg agcttgaatc  1740
tgacgagcat ggaaagacct tacggttgac atcgccagag ggtttaagtg agagcagaa   1800
atcccagtgg ctttcgacga ttaaagcagt cgtgcaaagt gccaaatact ggaatctggc  1860
agagtgcaca tttgaagcat cgggagaagg ggtcattatg aaggagcgcc agataactcc  1920
ggatgtatat aaggtcactc cagtgatgaa cacacatccg tcccaatcag aagcagtatc  1980
agatgttgg tctctctcaa agacatccat gactttccaa cccaagaaag caagtcttca   2040
gcctctcacc atatccttgg atgaattgtt ctcatctaga ggagagttca tctctgtcgg  2100
aggtgacgga cgaatgtctc ataaagaggc catcctgctc ggcctgagat acaaaaagtt  2160
gtacaatcag gcgagagtca atattctct gtagactatg aaaaaaagta acagatatca   2220
cgatctaagt gttatcccaa tccattcatc atgagttcct taaagaagat tctcggtctg  2280
```

```
aaggggaaag gtaagaaatc taagaaatta gggatcgcac caccccctta tgaagaggac    2340
actagcatgg agtatgctcc gagcgctcca attgacaaat cctattttgg agttgacgag    2400
atggacacct atgatccgaa tcaattaaga tatgagaaat tcttctttac agtgaaaatg    2460
acggttagat ctaatcgtcc gttcagaaca tactcgatg tggcagccgc tgtatcccat     2520
tgggatcaca tgtacatcgg aatggcaggg aaacgtccct tctacaaaat cttggctttt    2580
ttgggttctt ctaatctaaa ggccactcca gcggtattgg cagatcaagg tcaaccagag    2640
tatcacactc actgcgaagg cagggcttat ttgccacata ggatggggaa gacccctccc    2700
atgctcaatg taccagagca cttcagaaga ccattcaata taggtcttta caagggaacg    2760
attgagctca caatgaccat ctacgatgat gagtcactgg aagcagctcc tatgatctgg    2820
gatcatttca attcttccaa attttctgat ttcagagaga aggccttaat gtttggcctg    2880
attgtcgaga aaaggcatc tggagcgtgg gtcctggatt ctatcagcca cttcaaatga     2940
gctagtctaa cttctagctt ctgaacaatc cccggtttac tcagtctctc ctaattccag    3000
cctctcgaac aactaatatc ctgtcttttc tatccctatg aaaaaaacta acagagatcg    3060
atctgtttac gagattcttc atgtttggac caaatcaact tgtgatacca tgctcaaaga    3120
ggcctcaatt atatttgagt ttttaatttt tatgaaaaaa actaacagca atcatggaag    3180
tccacgattt tgagaccgac gagttcaatg atttcaatga agatgactat gccacaagag    3240
aattcctgaa tcccgatgag cgcatgacgt acttgaatca tgctgattac aacctgaatt    3300
ctcctctaat tagtgatgat attgacaatt taatcaggaa attcaattct cttccaattc    3360
cctcgatgtg ggatagtaag aactgggatg gagttcttga gatgttaaca tcatgtcaag    3420
ccaatcccat ctcaacatct cagatgcata aatggatggg aagttggtta atgtctgata    3480
atcatgatgc cagtcaaggg tatagttttt tacatgaagt ggacaaagag gcagaaataa    3540
catttgacgt ggtggagacc ttcatccgcg gctggggcaa caaaccaatt gaatacatca    3600
aaaaggaaag atggactgac tcattcaaaa ttctcgctta tttgtgtcaa aagttttggg    3660
acttacacaa gttgacatta atcttaaatg ctgtctctga ggtggaattg ctcaacttgg    3720
cgaggacttt caaaggcaaa gtcagaagaa gttctcatgg aacgaacata tgcaggatta    3780
gggttcccag cttgggtcct acttttattt cagaaggatg ggcttacttc aagaaacttg    3840
atattctaat ggaccgaaac tttctgttaa tggtcaaaga tgtgattata gggaggatgc    3900
aaacggtgct atccatggta tgtagaatag acaacctgtt ctcagagcaa gacatcttct    3960
cccttctaaa tatctacaga attggagata aaattgtgga gaggcaggga attttttctt    4020
atgacttgat taaaatggtg gaaccgatat gcaacttgaa gctgatgaaa ttagcaagag    4080
aatcaaggcc tttagtccca caattccctc attttgaaaa tcatatcaag acttctgttg    4140 atgaagggc aaaaattgac cgaggtataa gattcctcca tgatcagata atgagtgtga     4200
aaacagtgga tctcacactg gtgatttatg gatcgttcag acattggggt catccttta    4260 tagattatta cactggacta gaaaaattac attcccaagt aaccatgaag aaagatattg    4320
atgtgtcata tgcaaaagca cttgcaagtg atttagctcg gattgttcta tttcaacagt    4380
tcaatgatca taaaaagtgg ttcgtgaatg agagacttgct ccctcatgat catccctta    4440 aaagtcatgt taaagaaaat acatggccca cagctgctca agttcaagat tttggagata    4500
aatggcatga acttccgctg attaaatgtt ttgaaatacc cgacttacta gacccatcga    4560
taatatactc tgacaaaagt cattcaatga ataggtcaga ggtgttgaaa catgtccgaa    4620
tgaatccgaa cactcctatc cctagtaaaa aggtgttgca gactatgttg gacacaaagg    4680
```

```
ctaccaattg gaaagaattt cttaaagaga ttgatgagaa gggcttagat gatgatgatc   4740
taattattgg tcttaaagga aaggagaggg aactgaagtt ggcaggtaga ttttctccc    4800 taatgtcttg gaaattgcga gaatactttg taattaccga atatttgata aagactcatt   4860
tcgtccctat gtttaaaggc ctgacaatgg cggacgatct aactgcagtc attaaaaga    4920 tgttagattc ctcatccggc caaggattga agtcatatga ggcaatttgc atagccaatc   4980
acattgatta cgaaaaatgg aataaccacc aaaggaagtt atcaaacggc ccagtgttcc   5040
gagttatggg ccagttctta ggttatccat ccttaatcga gagaactcat gaattttttg   5100
agaaaagtct tatatactac aatggaagac cagacttgat gcgtgttcac aacaacacac   5160
tgatcaattc aacctcccaa cgagtttgtt ggcaaggaca gagggtgga ctggaaggtc    5220 tacggcaaaa aggatggact atcctcaatc tactggttat tcaaagagag gctaaaatca   5280
gaaacactgc tgtcaaagtc ttggcacaag gtgataatca agttatttgc acacagtata   5340
aaacgaagaa atcgagaaac gttgtagaat tacagggtgc tctcaatcaa atggtttcta   5400
ataatgagaa aattatgact gcaatcaaaa tagggacagg gaagttagga cttttgataa    5460
atgacgatga gactatgcaa tctgcagatt acttgaatta tggaaaaata ccgatttttcc   5520 gtggagtgat tagagggtta gagaccaaga gatggtcacg agtgacttgt gtcaccaatg   5580
accaaatacc cacttgtgct aatataatga gctcagtttc cacaaatgct ctcaccgtag    5640
ctcattttgc tgagaaccca atcaatgcca tgatacagta caattatttt gggacatttg   5700
ctagactctt gttgatgatg catgatcctg ctcttcgtca atcattgtat gaagttcaag   5760
ataagatacc gggcttgcac agttctactt tcaaatacgc catgttgtat ttggacccctt   5820 ccattggagg agtgtcgggc atgtctttgt ccaggttttt gattagagcc ttcccagatc   5880
ccgtaacaga aagtctctca ttctggagat tcatccatgt acatgctcga agtgagcatc   5940
tgaaggagat gagtgcagta tttggaaacc ccgagatagc caagtttcga ataactcaca   6000
tagacaagct agtagaagat ccaacctctc tgaacatcgc tatgggaatg agtccagcga   6060
acttgttaaa gactgaggtt aaaaaatgct taatcgaatc aagacaaacc atcaggaacc   6120
aggtgattaa ggatgcaacc atatatttgt atcatgaaga ggatcggctc agaagtttct   6180
tatggtcaat aaatcctctg ttccctagat ttttaagtga attcaaatca ggcactttt    6240 tgggagtcgc agacgggctc atcagtctat ttcaaaattc tcgtactatt cggaactcct   6300
ttaagaaaaa gtatcatagg gaattggatg atttgattgt gaggagtgag gtatcctctt    6360
tgacacattt agggaaactt catttgagaa ggggatcatg taaaatgtgg acatgttcag   6420
ctactcatgc tgacacatta agatacaaat cctggggccg tacagttatt gggacaactg    6480
taccccatcc attagaaatg ttgggtccac aacatcgaaa agagactcct tgtgcaccat    6540
gtaacacatc agggttcaat tatgtttctg tgcattgtcc agacgggatc catgacgtct    6600
ttagttcacg gggaccattg cctgcttatc tagggtctaa aacatctgaa tctacatcta    6660
ttttgcagcc ttgggaaagg gaaagcaaag tcccactgat taaaagagct acacgtctta    6720
gagatgctat ctcttggttt gttgaacccg actctaaact agcaatgact atactttcta    6780
acatccactc tttaacaggc gaagaatgga ccaaaaggca gcatgggttc aaaagaacag   6840
ggtctgccct tcataggttt tcgacatctc ggatgagcca tggtgggttc gcatctcaga   6900
gcactgcagc attgaccagg ttgatggcaa ctacagacac catgagggat ctgggagatc    6960
agaatttcga cttttttattc caagcaacgt tgctctatgc tcaaattacc accactgttg    7020
```

```
caagagacgg atggatcacc agttgtacag atcattatca tattgcctgt aagtcctgtt    7080
tgagacccat agaagagatc accctggact caagtatgga ctacacgccc ccagatgtat    7140
cccatgtgct gaagacatgg aggaatgggg aaggttcgtg gggacaagag ataaaacaga    7200
tctatccttt agaagggaat tggaagaatt tagcacctgc tgagcaatcc tatcaagtcg    7260
gcagatgtat aggttttcta tatggagact ggcgtatag aaaatctact catgccgagg    7320
acagttctct atttcctcta tctatacaag gtcgtattag aggtcgaggt ttcttaaaag    7380
ggttgctaga cggattaatg agagcaagtt gctgccaagt aatacaccgg agaagtctgg    7440
ctcatttgaa gaggccggcc aacgcagtgt acggaggttt gatttacttg attgataaat    7500
tgagtgtatc acctccattc ctttctctta ctagatcagg acctattaga gacgaattag    7560
aaacgattcc ccacaagatc ccaacctcct atccgacaag caaccgtgat atggggggtga    7620
ttgtcagaaa ttacttcaaa taccaatgcc gtctaattga aaagggaaaa tacagatcac    7680
attattcaca attatggtta ttctcagatg tcttatccat agacttcatt ggaccattct    7740
ctatttccac caccctcttg caaatcctat acaagccatt tttatctggg aaagataaga    7800
atgagttgag agagctggca aatctttctt cattgctaag atcaggagag gggtgggaag    7860
acatacatgt gaaattcttc accaaggaca tattattgtg tccagaggaa atcagacatg    7920
cttgcaagtt cgggattgct aaggataata ataaagacat gagctatccc ccttggggaa    7980
gggaatccag agggacaatt acaacaatcc ctgtttatta tacgaccacc ccttacccaa    8040
agatgctaga gatgcctcca agaatccaaa atccctgct gtccggaatc aggttgggcc    8100
aattaccaac tggcgctcat tataaaattc ggagtatatt acatggaatg ggaatccatt    8160
acagggactt cttgagttgt ggagacggct ccggagggat gactgctgca ttactacgag    8220
aaaatgtgca tagcagagga atattcaata gtctgttaga attatcaggg tcagtcatgc    8280
gaggcgcctc tcctgagccc cccagtgccc tagaaacttt aggaggagat aaatcgagat    8340
gtgtaaatgg tgaaacatgt tgggaatatc catctgactt atgtgaccca aggacttggg    8400
actatttcct ccgactcaaa gcaggcttgg ggcttcaaat tgatttaatt gtaatggata    8460
tggaagttcg ggattcttct actagcctga aaattgagac gaatgttaga aattatgtgc    8520
accggatttt ggatgagcaa ggagttttaa tctacaagac ttatggaaca tatatttgtg    8580
agagcgaaaa gaatgcagta acaatccttg gtcccatgtt caagacggtc gacttagttc    8640
aaacagaatt tagtagttct caaacgtctg aagtatatat ggtatgtaaa ggtttgaaga    8700
aattaatcga tgaacccaat cccgattggt cttccatcaa tgaatcctgg aaaaacctgt    8760
acgcattcca gtcatcagaa caggaatttg ccagagcaaa gaaggttagt acatacttta    8820
ccttgacagg tattccctcc caattcattc ctgatccttt tgtaaacatt gagactatgc    8880
tacaaatatt cggagtaccc acgggtgtgt ctcatgcggc tgccttaaaa tcatctgata    8940
gacctgcaga tttattgacc attagccttt tttatatggc gattatatcg tattataaca    9000
tcaatcatat cagagtagga ccgatacctc cgaaccccc atcagatgga attgcacaaa    9060
atgtggggat cgctataact ggtataagct tttggctgag tttgatggag aaagacattc    9120
cactatatca acagtgttta gcagttatcc agcaatcatt cccgattagg tgggaggctg    9180
tttcagtaaa aggaggatac aagcagaagt ggagtactag aggtgatggg ctcccaaaag    9240
atacccgaac ttcagactcc ttggccccaa tcgggaactg gatcagatct ctggaattgg    9300
tccgaaacca agttcgtcta aatccattca atgagatctt gttcaatcag ctatgtcgta    9360
cagtggataa tcatttgaaa tggtcaaatt tgcgaagaaa cacaggaatg attgaatgga    9420
```

```
tcaatagacg aatttcaaaa gaagaccggt ctatactgat gttgaagagt gacctacacg    9480
aggaaaactc ttggagagat taaaaaatca tgaggagact ccaaacttta agtatgaaaa    9540
aaactttgat ccttaagacc ctcttgtggt ttttatttt tatctggttt tgtggtcttc     9600
gtgggtcggc atggcatctc cacctcctcg cggtccgacc tgggcatccg aaggaggacg    9660
tcgtccactc ggatggctaa gggaggggcc cccgcggggc tgctaacaaa gcccgaaagg    9720
aagctgagtt ggctgctgcc accgctgagc aataactagc ataaccccctt ggggcctcta   9780 aacgggtctt gaggggtttt ttgctgaaag gaggaactat atccggatcg agacctcgat    9840
actagtgagc tcc                                                       9853
```

VESICULAR STOMATITIS VECTORS ENCODING CRIMEAN-CONGO HEMORRHAGIC FEVER ANTIGEN

RELATED APPLICATION

This application claims priority to U.S. Provisional Application No. 62/848,277 filed May 15, 2019, which is incorporated herein by reference in its entirety.

STATEMENT REGARDING FEDERALLY FUNDED RESEARCH

None.

REFERENCE TO SEQUENCE LISTING

A sequence listing required by 37 CFR 1.821-1.825 is being submitted electronically with this application. The sequence listing is incorporated herein by reference.

BACKGROUND

Crimean-Congo hemorrhagic fever (CCHF) is a widespread tick-borne viral disease that can affect humans. It is a member of the Bunyavirales order of RNA viruses. Clinical disease is rare in infected mammals, but it is commonly severe in infected humans. Outbreaks of illness are usually attributable to handling infected animals or contact with infected people.

The causative organism is found in Asia, Eastern Europe, the Middle East, a belt across central Africa and South Africa and Madagascar. The main environmental reservoir and vector for the virus is hard ticks. Ticks carry the virus to domestic animal stock. Sheep, goats and cattle can develop viremia, but tend not to fall ill. Tick species that have been identified as infected with this virus include *Argas reflexus*, *Hyalomma anatolicum*, *Hyalomma detritum*, *Hyalomma marginatum* and *Rhipicephalus sanguineus*.

The onset of CCHF is sudden, with initial signs and symptoms including headache, high fever, back pain, joint pain, stomach pain, and vomiting. Red eyes, a flushed face, a red throat, and petechiae (red spots) on the skin are common. Symptoms may also include jaundice, and in severe cases, changes in mood and sensory perception. As the illness progresses, large areas of severe bruising, severe nosebleeds, and uncontrolled bleeding at injection sites can be seen, beginning on about the fourth day of illness and lasting for about two weeks.

Animal herders, livestock workers, and slaughterhouses in endemic areas are at risk of CCHF. Healthcare workers in endemic areas are at risk of infection through unprotected contact with infectious blood and body fluids. Individuals and international travelers with contact to livestock in endemic regions may also be exposed. In documented outbreaks of CCHF, fatality rates in hospitalized patients have ranged from 5% to as high as 80%.

Previous attempts to develop preventative treatment include a USSR/Bulgarian CCHF vaccine developed in 1974 comprised an inactivated antigen from CCHF virus strain V42/81. It was generated from suckling mouse brain preparations, and so is unsuitable for FDA approval in the U.S. There is also a recombinantly produced construct comprising G1 ($G_C$), or G2 (Gn) glycoprotein ectodomains or portions thereof. However, no study exists to suggest any efficacy for this approach. Full effectiveness of this construct may be limited to the specific strain where the selected glycoproteins originated. There is no established virus-specific treatment. Ribavirin is thought to be effective in vitro, and has been used in human subjects during outbreaks. There are conflicting reports as to ribavirin effectiveness, with the more recent ones showing limited to no effectiveness against CCHF virus in vivo.

The Department of Defense views CCHF virus as a potential threat to the U.S. armed forces when operating in countries endemic to the virus. These geographical locations include but are not limited to Afghanistan, Pakistan, and the Middle East. The need for preventative treatment was underscored by death of a U.S. soldier from CCHF in 2009.

There remains a need for additional diagnostic, prophylactic, and therapeutic compositions and methods for CCHF.

SUMMARY

Certain embodiments are directed generally to compositions and methods related to recombinant vesicular stomatitis virus vectors (ΔGrVSV) encoding Crimean-Congo Hemorrhagic Fever glycoprotein precursor (CCHFV-GPC) and forming a recombinant vesicular stomatitis virus vector encoding Crimean-Congo Hemorrhagic Fever glycoprotein precursor (ΔGrVSV-CCHFV-GPC). In certain instance such compositions and methods can be but are not necessarily 100% effective against lethal CCHFV challenge with a single injection, as demonstrated in a mouse model, and can be effective across multiple species of CCHFV.

In certain embodiments the ΔGrVSV-CCHFV-GPC is replication competent. The replication competent ΔGrVSV-CCHFV-GPC can have a nucleotide sequence that is, is at least or is about 90, 91, 92, 93, 94, 95, 96, 97, 98, 99, to 100% identical to the nucleic acid sequence of SEQ ID NO:1. In certain instances the replication competent ΔGrVSV-CCHFV-GPC contains 20 single nucleotide polymorphisms throughout the genome, including mutations in the CCHFV-GPC. In certain aspects, the replication competent ΔGrVSV-CCHFV-GPC contains 1, 2, 3, 4, 5, 6, 7, 8, 9, 10, 11, 12, 13, 14, 15, 16, 17, 18, 19, or 20 variant nucleotides at one or more positions selected from position(s) 104, 1615, 1626, 1627, 1725, 1726, 2233, 2647, 2919, 2926, 2989, 4182, 4633, 7994, 8024, 8092, 8134, 8143, 10311, and/or 14322 of SEQ ID NO:1, wherein in an 1, 2, 3, 4, 5, 6, 7, 8, 9, 10, 11, 12, 13, 14, 15, 16, 17, 18, or 19 variants can be specifically excluded individually or in various combinations. In a particular aspect, the variant(s) are one or more of A104G, T1615C, A1626C, G1627A, C1725A, A1726G, T2233C, A2647G, T2919C, A2926G, T2989C, T4182A, C4633G, T7994G, G8024A, A8092T, T8134C, G8143C, C10311G, and/or C14322T of SEQ ID NO:1, wherein in an 1, 2, 3, 4, 5, 6, 7, 8, 9, 10, 11, 12, 13, 14, 15, 16, 17, 18, or 19 variants can be specifically excluded. SEQ ID NO:9 provides the nucleic acid sequence of a variant VSV backbone as compared to the VSV backbone of SEQ ID NO:10. In certain aspects the GPC mutant results in a 14 amino acid truncation at the C-terminal end of the glycoprotein precursor protein (SEQ ID NO:5 or SEQ ID NO:7), as compared to the full length SEQ ID NO:8. Certain embodiments are directed to an expression vector configured to express or overexpress a CCHFV-GPC described herein. In certain instances the amino acid sequence of CCHFV-GPC protein encoded by nucleic acids described herein is, is at least or is about 90, 91, 92, 93, 94, 95, 96, 97. 98. 99, to 100% identical to the amino acid sequence of SEQ ID NO:5 or SEQ ID NO:7 or the amino acid sequence of SEQ ID NO:8.

In certain embodiments the nucleic acid segment encoding the CCHFV-GPC is codon optimized. In certain instances the nucleic acid segment encoding the codon optimized CCHFV-GPC is 95, 96, 97, 98, 99, to 100% identical to nucleic acid sequence of SEQ ID NO:2. Certain embodiments are directed to an expression vector configured to express or overexpress a codon optimized nucleic acid encoding CCHFV-GPC as described herein. In certain aspect the optimized CCHFV-GPC provides an increase in production of CCHFV glycoproteins allowing localization in the plasma membrane and enabling uptake by VSV viruses budding from the cell surface.

Certain embodiments are directed to a replication deficient recombinant Vesicular Stomatitis Virus (rVSV) vector comprising a VSV glycoprotein deficient VSV (ΔGrVSV) genome encoding a Crimean-Congo Hemorrhagic Fever virus (CCHFV) glycoprotein precursor (GPC)(ΔGrVSV-CCHFV-GPC). In certain instance the replication deficient recombinant ΔGrVSV-CCHFV-GPC has a nucleic acid sequence that is, is at least, or is about 90, 91, 92, 93, 94, 95, 96, 97, 98, 99, to 100% identical to the nucleic acid sequence of SEQ ID NO:4.

In addition to constitutive expression, transcription can be controlled and/or driven by other expression systems in other expression platforms (mammalian cells vs. insect cells vs. bacteria) with T7 or PolII or T3 or Lac promoters etc. In certain aspects, the transcription of the nucleic acid sequence encoding the CCHFV-GPC is driven by a chicken actin promoter.

In certain aspects, the nucleic acid sequence encoding the CCHFV-GPC (SEQ ID NO:5) from the replication competent ΔGrVSV-CCHFV-GPC is 99.07% identical to the nucleic acid sequence of SEQ ID NO:4.

In certain aspects, the nucleic acid sequence encoding the CCHFV-GPC (SEQ ID NO:7) from the replication deficient ΔGrVSV-CCHFV-GPC is also 99.96% identical to the nucleic acid sequence of SEQ ID NO:6.

In certain aspects, the encoded CCHFV-GPC (SEQ ID NO:2) from the replication competent ΔGrVSV-CCHFV-GPC has an amino acid sequence that is 99.8% identical to the fully intact codon-optimized CCHFV-GPC amino acid sequence of SEQ ID NO:8.

In certain aspects, the vector backbone of the replication competent ΔGrVSV-CCHFV-GPC (SEQ ID NO:9) has a nucleic acid sequence that is 99.86% identical to the starting vector ΔGrVSV SEQ ID NO:10.

In certain embodiments a vector described herein can included in an expression cassette. The expression cassette can be further included in an expression vector, such as a plasmid vector, that expresses the ΔGrVSV-CCHFV-GPC nucleic acid.

Certain embodiments are directed to a recombinant Vesicular Stomatitis Virus (rVSV) comprising a Crimean-Congo Hemorrhagic Fever virus (CCHFV) glycoprotein (rVSV-CCHFV-GP) $G_N$ and/or $G_C$.

Other embodiments can include a vaccine composition including a vector or a virus as described herein.

Certain embodiments are directed to methods of producing an immune response in a mammal comprising administering one or more of a vector, a virus, or a vaccine as described herein to a mammal, and in particular a human. The virus, vector, or vaccine can be administered by injection, inhalation, or instillation.

Certain embodiments are directed to methods for producing a replication competent recombinant Vesicular Stomatitis Virus comprising a Crimean-Congo Hemorrhagic Fever virus glycoprotein precursor vector (ΔGrVSV-CCHFV-GPC) comprising the step of passaging a VSV glycoprotein complemented recombinant Vesicular Stomatitis Virus encoding Crimean-Congo Hemorrhagic Fever virus glycoprotein precursor (VSV-G*-ΔGrVSV-CCHFV-GPC) in a non-complementing VSV glycoprotein cell line and isolating a replication competent ΔGrVSV-CCHFV-GPC vector.

Other embodiments are directed to methods of producing replication competent recombinant Vesicular Stomatitis Virus encoding a Crimean-Congo Hemorrhagic Fever virus glycoprotein virus (ΔGrVSV-CCHFV-GP), comprising infecting a cell culture with the isolated replication competent ΔGrVSV-CCHFV-GPC vector and isolating ΔGrVSV-CCHFV-GP virus produced by the infected cells.

Certain embodiments are directed to kits comprising one or more of (a) at least one dose of a replication competent recombinant Vesicular Stomatitis Virus comprising a Crimean-Congo Hemorrhagic Fever virus glycoprotein precursor vector (ΔGrVSV-CCHFV-GPC); or (b) at least one dose of a replication competent recombinant Vesicular Stomatitis Virus comprising a Crimean-Congo Hemorrhagic Fever virus glycoprotein virus (ΔGrVSV-CCHFV-GP).

Other embodiments are directed to methods for identifying a subject infected with or exposed to Crimean-Congo Hemorrhagic Fever virus comprising the steps of: (a) contacting a biological sample with a recombinant Vesicular Stomatitis Virus comprising a Crimean-Congo Hemorrhagic Fever virus glycoprotein virus (ΔGrVSV-CCHFV-GP) or a cell expressing a recombinant Vesicular Stomatitis Virus comprising a Crimean-Congo Hemorrhagic Fever virus glycoprotein precursor vector (ΔGrVSV-CCHFV-GPC) forming a Crimean-Congo Hemorrhagic Fever glycoprotein/antibody complex with Crimean-Congo Hemorrhagic Fever glycoprotein specific antibodies present in the sample; and (b) detecting glycoprotein/antibody complexes.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

As used herein, "rVSV" is used to refer to a recombinant vesicular stomatitis virus.

The terms "protein", "peptide", "polypeptide", and "amino acid sequence" are used interchangeably herein to refer to polymers of amino acid residues of any length. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the term "variant" refers to a polypeptide or nucleic acid differing from a reference nucleic acid or polypeptide, but retaining essential properties thereof. Generally, variants are overall closely similar, and, in many regions, identical to the reference nucleic acid or polypeptide. A variant can include one or more nucleotide or amino acid substitutions.

As used herein the term "mutant" refers to a protein or polypeptide in which one or more amino acids are added and/or substituted and/or deleted and/or inserted at the N-terminus, and/or the C-terminus, and/or within the native amino acid sequences of the proteins or polypeptides disclosed herein. As used herein the term "mutant" can refer to a nucleic acid molecule that encodes a mutant protein. Moreover, the term "mutant" refers to any shorter or longer version of the protein or nucleic acid herein.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" or "heterologous nucleic acid sequence" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

As regards codon optimization, the nucleic acid molecules of the invention have a nucleotide sequence that encodes the antigens of the invention and may be designed to employ codons that are used in the genes of the subject in which the antigen is to be produced. Many viruses use a large number of rare codons and, by altering these codons to correspond to codons commonly used in the desired subject, enhanced expression of the antigens may be achieved. In a preferred embodiment, the codons used are "humanized" codons, i.e., the codons are those that appear frequently in highly expressed human genes (Andre et al., *J. Virol.* 72:1497-1503, 1998) instead of those codons that are frequently used by a virus. Such codon usage provides for efficient expression of the transgenic proteins in human cells. Any suitable method of codon optimization may be used.

Certain embodiments encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the antigen, epitope, immunogen, peptide or polypeptide of interest.

For the purposes of the present invention, sequence identity is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin and Altschul, *Proc. Natl. Acad. Sci. USA* 1990; 87: 2264-2268, modified as in Karlin and Altschul, *Proc. Natl. Acad. Sci. USA* 1993; 90: 5873-5877. Another example of a mathematical algorithm used for comparison of sequences is the algorithm of Myers and Miller, CABIOS 1988; 4: 11-17. Such an algorithm is incorporated into the ALIGN™ program (version 2.0) which is part of the GCG sequence alignment software package. When utilizing the ALIGN™ program for comparing amino acid sequences, a PAM 120 weight residue table, a gap length penalty of 12, and a gap penalty of 4 may be used. Yet another useful algorithm for identifying regions of local sequence similarity and alignment is the FASTA algorithm as described in Pearson and Lipman, *Proc. Natl. Acad. Sci. USA* 1988; 85: 2444-2448.

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antigens described herein may be used in accordance with the present invention. In certain embodiments, the antigens may be used in vitro (such as using cell-free expression systems) and/or in cultured cells grown in vitro in order to produce the encoded CCHFV antigens which may then be used for various applications such as in the production of proteinaceous vaccines. For such applications, any vector that allows expression of the antigen(s) in vivo, in vitro and/or in cultured cells may be used.

For applications where it is desired that the antigen(s) be expressed in vivo, for example when the transgenes of the invention are used in DNA or DNA-containing vaccines, any vector that allows for the expression of the antigen(s) described herein and is safe for use in vivo may be used. In preferred embodiments the vectors used are safe for use in humans, mammals and/or laboratory animals.

For the antigen(s) described herein to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes or coding regions described herein may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the invention. For example, suitable promoters and/or enhancers may be selected from the Eukaryotic Promoter Database (EPDB).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1. rVSV-CCHFV-GPC vectors design and vaccine study strategy. (A) Generating a replication deficient vaccine vector: Genome organization comparing VSV (wild-type) genome (in grey arrows) and the rVSV vector expressing the CCHFV-GPC codon optimized open reading frame. N; nucleoprotein, P; phosphoprotein, M; matrix protein, and L; large polymerase protein. The rVSV-CCHFV-GPC vector had natural VSV glycoprotein gene (yellow arrow) exchanged with the open reading frame coding for the full glycoprotein precursor gene (GPC) of CCHFV (red arrow). Using a T7 driven DNA clone recovery system, complemented VSV-G* recombinant was generated containing the CCHFV-GPC open reading frame (VSV-G*-ΔGrVSV-CCHFV-GPC). (B) Generating a replication competent vaccine vector: VSV-G*-ΔGrVSV-CCHFV-GPC is infectious due to the VSV-G complementation; however, VSV-G is needed in trans to effectively replicate in cell culture. Multiple passages of this vector through VSV-G complemented and un-complemented BHK cells resulted in a replication competent vaccine vector (ΔGrVSV-ΔCCHFV-GPC). Next generation sequencing revealed six nonsynonymous mutations in the open reading frame of the CCHFV-GPC. These mutations resulted in the truncation of fourteen amino acids off the end of GPC C-terminal tail of the glycoprotein ($G_C$).

FIG. 2. Characterization of rVSV-CCHFV-GPC vectors. (A) Single-cycle growth kinetics comparing rVSV wild-type (Isolate: Indiana) tagged with GFP (rVSV-GFP), VSV-G*-ΔGrVSV-CCHFV-GPC, ΔGrVSV-ΔCCHFV-GPC, and CCHFV (Isolate: IbAr10200) all at MOI 0.1 in BHK cells. Data shown are a mean±standard deviation from three biological replicates, titrated by plaque assay in duplicate. Complemented VSV-G* BHK (via transfection with pCAGGS-VSV-$G_{Indiana}$) were used for VSV-G*-ΔGrVSV-CCHFV-GPC kinetics and plaque assays. (B) Phase and fluorescence microscopy of MOI 3 and MOI 0.01 infected SW-13-CDC (VSV-G*-ΔGrVSV-CCHFV-GPC) and BHK (ΔGrVSV-ΔCCHFV-GPC) cells at 10× objectives, stained with α-CCHFV-$G_C$ MAb 8A1 using a FITC-conjugated secondary at 24 and 96 hpi, respectively. (C) Coomassie of approximately 100 ng of loaded 20% sucrose cushioned/semi-purified and gradient purified particles on 4-16% gradient TGX gels. 1: rVSV-GFP, 2: VSV-G*-ΔGrVSV-CCHFV-GPC, 3: ΔGrVSV-ΔCCHFV-GPC, and 4: CCHFV. Particle preps were stained with Coomassie Fluor Orange. (D) Western blot of approximately 100 ng of loaded 20% sucrose cushioned/semi-purified and iodixanol gradient purified particles on 4-16% gradient TGX gels. 1: rVSV-GFP, 2: VSV-G*-ΔGrVSV-CCHFV-GPC, 3: ΔGrVSV-ΔCCHFV-GPC, and 4: CCHFV. Particle preparations were stained with α-CCHFV-$G_C$ MAb 11E7 using an HRP-conjugated secondary. (E) Transmission electron micrographs of rVSV-GFP and replication competent ΔGrVSV-ΔCCHFV-GPC particles from BHK cells, semi-purified using a 20% sucrose cushion or purified using iodixanol gradient centrifugation, negatively stained with 2% aqueous uranyl acetate, immunolabeled with α-CCHFV-$G_C$ MAb 11E7 and a secondary 15 nm gold labeled secondary. Samples were fixed with 2% glutaraldehyde. Images 2(B), 2(C), 2(D), and 2(E) were adjusted for brightness, contrast, and formatted for size for display purposes. Size markers are indicated in each image for reference.

FIG. 3. Pilot in vivo CCHFV vaccine study. (A) Experimental conditions including animal type, number, group, prime/boost/challenge conditions, routes, dose amounts, and schedule. Flow chart showing vaccination (triangles), sampling days (arrows), and day of challenge (*). (B) Kaplan-Meier survival curve of challenged animal groups. Group is indicated by color which corresponds to the colored triangles outlined in FIG. 3A, above. (C) Averaged weights from all groups collected each day for 35 days pre-challenge and 28 days post challenge total. (D) Averaged temperatures from all groups collected each day for 35 days pre-challenge and 28 days post challenge total.

DESCRIPTION

Figure 4:
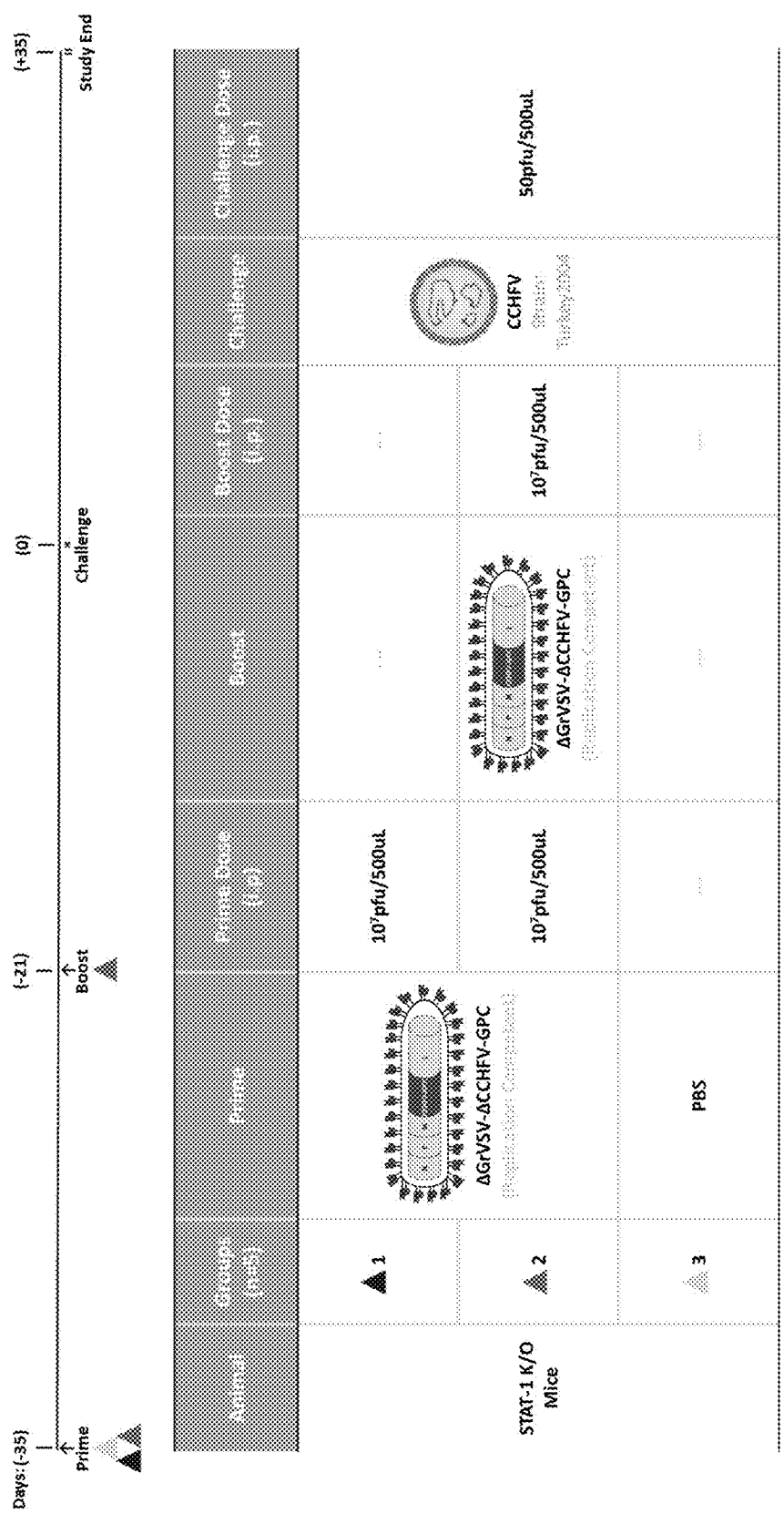
FIG. 4. Second in vivo CCHFV vaccine study. Experimental conditions including animal type, number, group, prime/boost/challenge conditions, routes, dose amounts, and schedule. Flow chart showing vaccination (triangles), sampling days (arrows), and day of challenge (*).

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The Crimean-Congo hemorrhagic fever (CCHF) virus is a member of the genus Nairovirus, family Bunyaviridae. The negative sense RNA genome is composed of three segments—Small (S), Middle (M) and Large (L). The L segment is 11-14.4 kilobases in length while the M and S segments are 4.4-6.3 and 1.7-2.1 kilobases long respectively. The L segment encodes the RNA polymerase; the M segment encodes the envelope proteins ($G_C$ and $G_N$); and the S segment encodes the nucleocapsid protein. The envelope protein is initially translated as a glycoprotein precursor which is then cleaved into the mature structural glycoprotein products ($G_N$ and $G_C$) and non-structural glycoproteins.

Crimean-Congo hemorrhagic fever virus (CCHFV) is a highly pathogenic zoonotic agent in the Orthonairovirus genus within Nairoviridae (1). The principal reservoirs for CCHFV are ixodid hard ticks primarily belonging to the genus *Hyalomma* (2). These ticks maintain the virus in nature by feeding on small mammals, ungulates, and birds within thirty countries across the Eastern hemisphere (3). Human infection can occur from the bite of an infected tick, exposure to infected animal products, or through nosocomial transmission (4). CCHFV case-fatality rates in most outbreaks range from 3-30%, though higher rates have been documented in some instances (3, 5). CCHFV is categorized as a Category A priority pathogen by the National Institutes of Health due to its associated morbidity and mortality, potential for public health/societal impact, as well as a lack of approved therapeutic options or US/EU licensed vaccines for treatment. The guanosine analogue ribavirin has been suggested as a therapeutic when given early in human infections; however, efficacy has not been clearly demonstrated in clinical trials for CCHF (6). For these reasons, vaccines and therapeutic countermeasures against CCHFV are currently under development.

Full or partial mature CCHFV particles contain single stranded, tri-partite, negative sense RNA genomes with small (S), medium (M), and large (L) segments, respectively encoding the structural nucleoprotein (NP), two envelope proteins ($G_N$ and $G_C$) and the viral RNA-dependent-RNA-polymerase (RdRp) (3). The M-segment contains a 5.1 kilobase open-reading frame which codes for a glycoprotein precursor polypeptide (GPC) (7). Host cell processing, cleavage events, and post-translational modifications of this GPC yield the two mature structural glycoproteins $G_N$ and $G_C$, along with several non-structural glycoproteins which aid in structural $G_N$ and $G_C$ maturation (7-12). The two glycoproteins are likely responsible for pertinent events in the viral replication cycle such as viral attachment, cell entry, tissue tropism(s), and induction of protective immune response as seen similarly with other members of Bunyavirales (13, 14). The latter has been demonstrated for CCHFV using monoclonal antibodies (MAb) directed against $G_N$ and $G_C$, which have demonstrated in vitro neutralization in tissue culture and in vivo passive protection in suckling mice (13-15). These data suggest that the GPC would be an important antiviral target for therapeutic and vaccine efforts.

Currently, there are several experimental vaccine candidates that have relied on the GPC as an antigenic component, which have been evaluated in immunocompromised signal transducer and activator of transcription 1 knock-out ($STAT-1^{-/-}$), interferon $\alpha/\beta$ receptor knock-out (IFNAR), or interferon receptor antibody transiently suppressed (IS) mouse models for CCHFV, as they recapitulate clinical illness and are uniformly lethal models for CCHF (16-20). Vaccine candidate approaches have focused on either DNA expression of CCHFV antigens in host tissues, replication deficient viral-like particles, inactivated whole virus preparations, subunit antigen preparations, or vectored vaccinia virus vaccines (16, 20-25). Two of these preparations, a prime and boost strategy using modified recombinant Vaccinia virus (strain: Ankara) [MVA] encoding the GPC, and a prime, boost, and boost strategy with a DNA based vaccine encoding separate NP, $G_N$, and $G_C$ antigens, have provided promising results with up to 100% protection in the $IFNAR^{K/O}$ animal model (23, 25). Although the NP by itself in the MVA platform has failed to provide protection (26).

Recombinant vesicular stomatitis viruses (rVSV) have been developed and evaluated as promising experimental vaccines for several pathogens, often requiring only a single-dose to induce protection (27-31). The rVSV platform has been experimentally evaluated for both durability and safety (32-34), and two rVSV vaccines, one for human immunodeficiency virus (HIV) (35) and a second for Zaire ebolavirus (EBOV), have been tested in human clinical trials (36-38). For these reasons, the inventors contemplate that rVSV vectors expressing CCHFV-GPC could elicit a protective response in a lethal animal model for CCHF. The aim of our study was to design, generate, characterize, and evaluate a rVSV vector encoding the CCHFV-GPC as an experimental vaccine for CCHFV.

I. RECOMBINANT VIRUS

Vesicular Stomatitis Virus (VSV) is a non-segmented negative-stranded RNA virus and belongs to the family Rhabdoviridae, genus Vesiculovirus. Its simple structure and rapid high-titered growth in mammalian and many other cell types has made it a preferential tool for molecular and cell biologists in the past 30 years. This was even strengthened with the establishment of the reverse genetics system for VSV.

VSV encodes five proteins, nucleocapsid protein (N), phosphoprotein (P), matrix protein (M), surface glycoprotein (G), and RNA dependent RNA polymerase (L). The N, P, and L proteins of VSV are required for synthesis of positive sense and negative sense genomic RNAs and mRNA, which are necessary for the synthesis of VSV proteins.

In certain embodiments, a recombinant vesicular stomatitis virus (rVSV) can be a full length VSV or a VSV lacking all or part of a surface glycoprotein encoding region (ΔGrVSV) that includes heterologous nucleic acid segment that is capable of inducing an immune response in a subject by expression of an epitope of a CCHFV. The rVSV of the present invention may induce humoral, cellular, and/or mucosal immune responses.

The rVSVs of the present invention can be prepared using techniques known in the art and/or described herein. In one embodiment, the rVSVs may be introduced in a host cell under conditions suitable for the replication and expression of the rVSV in the host. Accordingly, the present invention also provides a cell having a rVSV that has been adapted to replicate in the cell without supplying VSV G protein in trans. As such, the present invention relates also to a cell having one or more of the recombinant VSVs described herein.

Embodiments include replication competent and replication deficient ΔGrVSV-CCHFV-GPC. In certain aspects, the replication competent ΔGrVSV-CCHFV-GPC contains 1, 2, 3, 4, 5, 6, 7, 8, 9, 10, 11, 12, 13, 14, 15, 16, 17, 18, 19, or 20 variant nucleotides at positions 104, 1615, 1626, 1627, 1725, 1726, 2233, 2647, 2919, 2926, 2989, 4182, 4633, 7994, 8024, 8092, 8134, 8143, 10311, 14322 of SEQ ID NO:1, wherein in an 1, 2, 3, 4, 5, 6, 7, 8, 9, 10, 11, 12, 13, 14, 15, 16, 17, 18, or 19 variants can be specifically excluded. In a particular aspect, the variant is a A104G, T1615C, A1626C, G1627A, C1725A, A1726G, T2233C, A2647G, T2919C, A2926G, T2989C, T4182A, C4633G, T7994G, G8024A, A8092T, T8134C, G8143C, C10311G, and/or C14322T of SEQ ID NO:1, wherein in an 1, 2, 3, 4, 5, 6, 7, 8, 9, 10, 11, 12, 13, 14, 15, 16, 17, 18, or 19 variants can be specifically excluded.

The A104 variant is located in the VSV Nucloprotein coding sequence position 40 and is typically an A to G. The variant can result in a VSV Nucelopprotein mutation 114V.

The T1615 variant is located in the VSV Phosphoprotein coding sequence at position 219 and is typically a T to C. The variant typically does not result in an amino acid change in the VSV Phosphoprotein at amino acid G72.

The A1626 variant is located in the VSV Phosphoprotein coding sequence at position 230 and is typically a A to C substitution. The variant typically results in a VSV Phosphoprotein with a Q77P mutation.

The G1627 variant is located in the VSV Phosphoprotein coding sequence at position 231 and is typically a G to A. The variant typically results in a VSV Phosphoprotein Q77P mutation.

The C1725 variant is located in the VSV Phosphoprotein coding sequence at position 329 and is typically a C to A. The variant typically results in a VSV Phosphoprotein with a P110Q mutation.

The A1726 variant is located in the VSV Phosphoprotein coding sequence at position 330 and is typically a A to G. The variant typically results in a VSV Phosphoprotein with a P110Q mutation.

The T2233 variant is located in the Intergenic region between VSV Phosphoprotein and Matrixprotein at position 39 and is typically a T to C.

The A2647 variant is located in the VSV Matrixprotein coding sequence at position 397 and is typically A to G. The variant typically results in a VSV Matrixprotein with a T133A mutation.

The T2919 variant is located in the VSV Matrixprotein coding sequence at position 669 and is typically T to C. The variant typically results in a VSV Matrixprotein that retains D223 amino acid residue.

The A2926 variant is located in the VSV Matrixprotein coding sequence at position 676 and is typically A to G. The variant typically results in a VSV Matrixprotein with a S226G mutation.

The T2989 variant is located in the intergenic region between VSV Matrixprotein and truncated CCHFV Glycoprotein precursor (GPC) at position 49 and is typically T to C.

The T4182 variant is located in the truncated CCHFV Glycoprotein precursor (GPC) coding sequence at position 1101 and is typically T to A. The variant typically results in a truncated CCHFV Glycoprotein precursor (GPC) in a S368T mutation.

The C4633 variant is located in the CCHFV Glycoprotein precursor (GPC) coding sequence at position 1552 and is typically C to G. The variant typically results in a truncated CCHFV Glycoprotein precursor (GPC) having a L518V mutation.

The T7994 variant is located in the CCHFV Glycoprotein precursor (GPC) coding sequence at position 4913 and is typically T to G. The variant typically results in a truncated CCHFV Glycoprotein precursor (GPC) having a L1638R mutation.

The G8024 variant is located in the CCHFV Glycoprotein precursor (GPC) coding sequence at position 4943 and is typically G to A. The variant typically results in a truncated CCHFV Glycoprotein precursor (GPC) having a R1648Q mutation.

The A8092 variant is located in the CCHFV Glycoprotein precursor (GPC) coding sequence at position 5,011 and is typically A to T, resulting in the truncation of CCHFV GPC. The variant typically results in a Truncated CCHFV Glycoprotein precursor (GPC) open reading frame at position 1671 where an Arginine (Arg [R]) is mutated to a STOP Codon.

The T8134 variant is located in the newly created intergenic region between truncated CCHFV Glycoprotein precursor (GPC) and VSV Polymerase at position 40 and is typically T to C.

The G8143 variant is located in the newly created intergenic region between truncated CCHFV Glycoprotein precursor (GPC) and VSV Polymerase at position 49 and is typically G to C.

The C10311 variant is located in the VSV Polymerase coding sequence at position 2066 and is typically C to G. The variant typically results in a VSV Polymerase having a T689S mutation.

The C14322 variant is located in the VSV Polymerase coding sequence at position 6077 and is typically C to T. The variant typically results in a VSV Polymerase having a T20261 mutation.

II. VACCINES OR IMMUNOGENIC COMPOSITIONS

Certain embodiments are directed to vaccines or immunogenic compositions comprising one or more of the rVSVs described herein. In one embodiment, the present invention features vaccines or immunogenic compositions comprising a rVSV-CCHFV-GPC and vaccines or immunogenic compositions comprising a rVSV-CCHFV-GP, as described herein.

The nucleotide sequences and/or antigens can be administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the immunogenic compositions and vaccines. In other embodiments, it will be desirable to express the antigens in human subjects, such as in clinical trials and for actual clinical use of the immunogenic compositions and vaccine of the invention. In preferred embodiments the subject is a human, for example a human that is infected with, or is at risk of infection with, CCHFV.

For such in vivo applications the nucleotide sequences and/or antigens can be administered as a component of an immunogenic composition which may comprise the nucleotide sequences and/or antigens in admixture with a pharmaceutically acceptable carrier. The immunogenic compositions of the invention are useful to stimulate an immune response against CCHFV and may be used as one or more components of a prophylactic or therapeutic vaccine against CCHFV for the prevention, amelioration or treatment of CCHF. The nucleic acids and vectors can be particularly useful for providing genetic vaccines, i.e., vaccines for delivering the nucleic acids encoding the antigens to a subject, such as a human, such that the antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector having the desired degree of purity is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The immunogenic compositions may contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO$_4$)$_2$, AlNa(SO$_4$)$_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, poly IC or poly AU acids, polyarginine with or without CpG (also known in the art as IC31), JuvaVax™, certain natural substances (e.g., wax D from *Mycobacterium tuberculosis*, substances found in Cornyebacterium *parvum*, *Bordetella pertussis*, or members of the genus *Brucella*), flagellin (Toll-like receptor 5 ligand, saponins such as QS21, QS17, and QS7, monophosphoryl lipid A, in particular, 3-de-O-acylated monophosphoryl lipid A (3D-MPL), imiquimod (also known in the art as IQM and commercially available as Aldara®; and the CCR5 inhibitor CMPD167.

The immunogenic compositions may be designed to introduce the nucleic acids or expression vectors to a desired site of action and release it at an appropriate and controllable rate. Methods of preparing controlled-release formulations are known in the art. For example, controlled release preparations may be produced by the use of polymers to complex or absorb the immunogen and/or immunogenic composition. A controlled-release formulations may be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention may be readily determined by those of skill in the art. For example, the dosage of the immunogens may vary depending on the route of administration and the size of the subject. Suitable doses may be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of infection, or evidence of infection, or in advance of any symptom due to CCHF, especially in high-risk subjects. The prophylactic administration of the immunogenic compositions may serve to provide protective immunity of a subject against CCHFV infection or to prevent or attenuate the progression of CCHF in a subject already infected with CCHFV. When provided therapeutically, the immunogenic compositions may serve to ameliorate and treat CCHF symptoms and are advantageously used as soon after infection as possible, preferably before appearance of any symptoms of CCHF but may also be used at (or after) the onset of the disease symptoms.

The immunogenic compositions may be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes, direct injection of naked DNA into animal muscle tissue, or intradermal injection of DNA using "gene gun" technology. Alternatively, delivery routes may be oral, intranasal or by any other suitable route. Delivery may also be accomplished via a mucosal surface such as the anal, vaginal or oral mucosa. Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response may also include administration of an adjuvant with the immunogens. In some instances, annual, biannual or other long interval (5-10 years) booster immunization may supplement the initial immunization protocol.

Methods may also include a variety of prime-boost regimens, for example DNA prime-boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors to provide priming and boosting regimens.

A specific embodiment of the invention provides methods of inducing an immune response against CCHFV in a subject by administering an immunogenic composition described herein, preferably which may comprise a vector containing DNA encoding one or more of the epitopes of the invention, one or more times to a subject wherein the epitopes are expressed at a level sufficient to induce a specific immune response in the subject. Such immunizations may be repeated multiple times at time intervals of at least 2, 4 or 6 weeks (or more) in accordance with a desired immunization regime.

The immunogenic compositions of the invention may be administered alone, or may be co-administered, or sequentially administered, with other CCHFV immunogens and/or CCHFV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages may be determined taking into consideration such factors as the age, sex, weight, species and condition of the particular subject, and the route of administration.

When used in combination, the other CCHFV immunogens may be administered at the same time or at different times as part of an overall immunization regime, e.g., as part of a prime-boost regimen or other immunization protocol.

It is to be understood and expected that variations in the principles of invention as described above may be made by one skilled in the art and it is intended that such modifications, changes, and substitutions are to be included within the scope of the present invention. The dose of the vaccine may vary according to factors such as the disease state, age, sex, and weight of the individual, and the ability of antibody to elicit a desired response in the individual. Dosage regime may be adjusted to provide the optimum therapeutic response. The dose of the vaccine may also be varied to provide optimum preventative dose response depending upon the circumstances.

III. KITS

Certain embodiments are directed to for example for preventing or treating an infection. For example, a kit may comprise one or more pharmaceutical compositions or vaccines as described above and optionally instructions for their use. In still other embodiments, the invention provides kits comprising one or more pharmaceutical compositions or vaccines and one or more devices for accomplishing administration of such compositions.

Kit components may be packaged for either manual or partially or wholly automated practice of the methods described herein. In other embodiments involving kits, it is contemplated that a kit includes compositions described herein, and optionally instructions for their use. Such kits may have a variety of uses, including, for example, imaging, diagnosis, therapy, and other applications.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
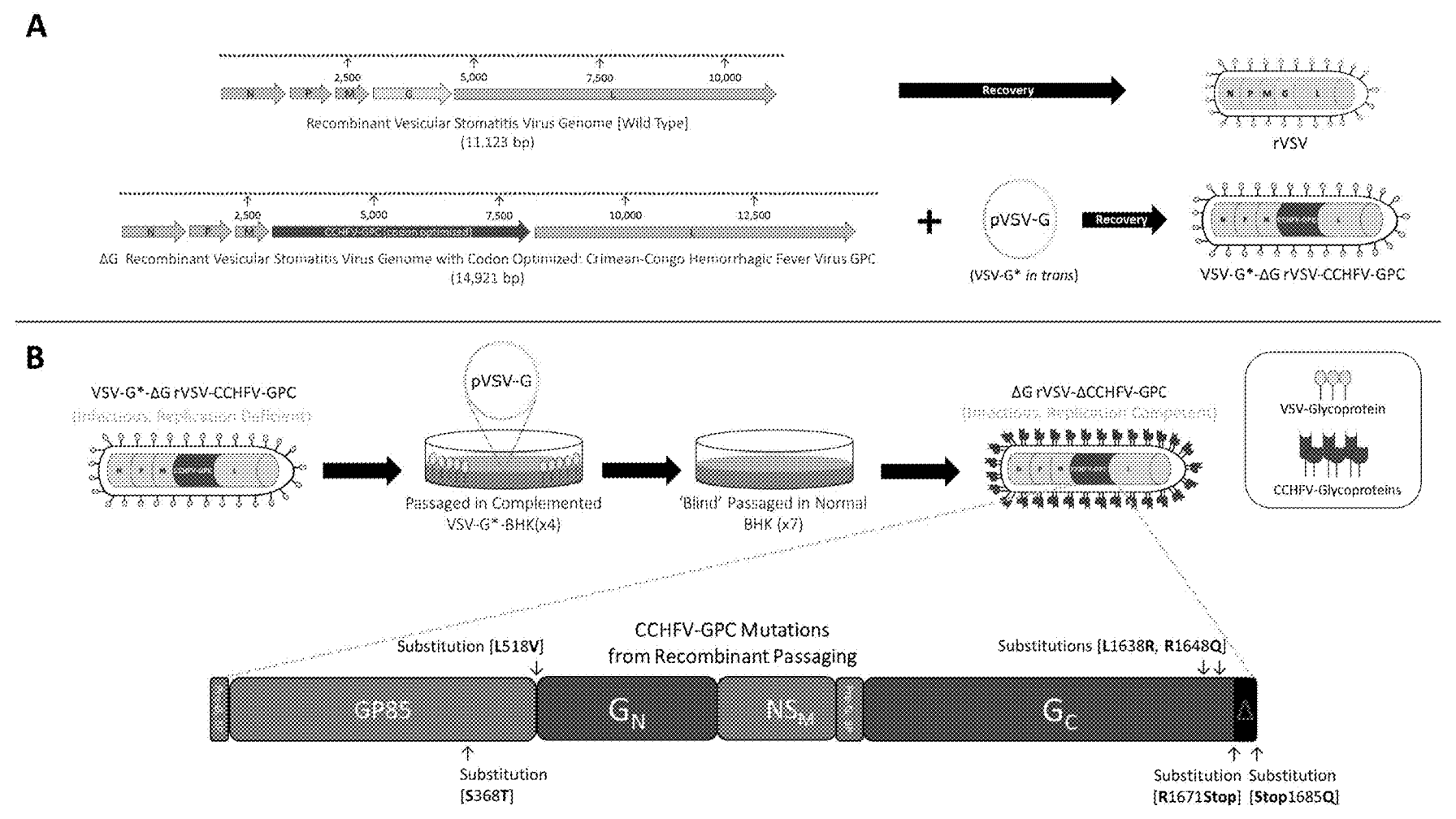

Replication Competent Vesicular Stomatitis Vector Protects Against Lethal Crimean-Congo Hemorrhagic Fever Infection in Mice A. Results To ensure robust expression of the CCHFV-GPC antigen, the inventors chose to use a codon optimized CCHFV-GPC (strain: IbAr10200) containing plasmid and subsequently examined expression of CCHFV-GPC, in human liver cells transiently expressing the codon optimized CCHFV-GPC from a pCAGGs plasmid. Interestingly, immunofluorescence staining of CCHFV-$G_C$ on un-permeabilized, plasma membrane stained cells, demonstrated cell surface staining of transfected cells (Supplemental FIG. 1). These initial data, suggested over-expression under a strong promoter (such as the chicken actin promoter), as well as codon optimization, could uncharacteristically localize CCHFV-GP to the plasma membrane instead of the Golgi (14, 39) where VSV could acquire the GP when budding from the cell surface (40).

Encouraged by these over-expression results using the codon optimized CCHFV-GPC; the inventors cloned and recovered ΔGrVSV-CCHFV-GPC. Our initial attempts using the DNA clone recovery system designed by Lawson et al., failed to produce infectious ΔGrVSV-CCHFV-GPC (FIG. 1A) (41). To overcome this hurdle, the inventors used a modification based on a system described by Whitt (42) relying on in trans VSV glycoprotein (G) complementation (VSV-G*) of ΔGrVSV virions. This technique allowed for VSV-G, incorporation into recoveries to facilitate efficient assembly of the VSVΔG-CCHFV-GPC genome without the need for CCHFV-GPC to participate in initial infection of recovered virions (FIG. 1A). Thus, the inventors recovered a virion containing the CCHFV-GPC in the genome with VSV-G complementation (VSV-G*-ΔGrVSV-CCHFV-GPC) contributing to a single-cycle infection; unless VSV-G is provided in trans this virus will not replicate effectively in cell culture.

After the initial recovery of VSV-G*-ΔGrVSV-CCHFV-GPC, this virus was passaged multiple times on VSV-G complemented BHK cells and simultaneously passaged onto un-complemented ('normal') BHK cells. the inventors were unable to isolate infectious virus from initial supernatants however, seven total serial passages of supernatants on un-complemented BHK cells resulted in eventual cytopathic effect (CPE) in cell culture with plaque formations on the monolayers (FIG. 1B). These monolayers with CPE were harvested for RNA and stained for CCHFV-$G_C$ antigen via immunofluorescence assay. Sanger sequencing of both constructs, using primers for the CCHFV-GPC ORF, was carried out which revealed several single nucleotide polymorphisms (data not shown). Next generation sequencing (NGS) was then performed to confirm Sanger results and further detail the signal nucleotide polymorphisms within the entire genomes of both constructs (Supplemental Table 1). NGS sequencing demonstrated fourteen identical single nucleotide polymorphisms (SNP) preserved between the replication deficient and replication competent constructs; with the replication competent construct possessing four additional non-synonymous mutations within the CCHFV-GPC (FIG. 1B, Supplemental Table 1). Two of these mutations within the CCHFV-GPC of the replication competent construct, resulted in the truncation of fourteen amino acids off the C-terminal tail of the $G_C$ (FIG. 1B).

To assess the growth kinetics of the rVSV vectors compared to authentic CCHFV, the inventors performed single-cycle growth curve analysis on BHK cells infected with respective viruses at various time intervals up to 96 hrs post infection (hpi) or full monolayer destruction. The rVSV-GFP (wild-type control) peaked in titer at approximately 24 hpi, while CCHFV prototype-strain: IbAr10200 peaked at 48 hpi (FIG. 2A). Using VSV-G* complemented BHK cells, enabled replication, spreading, and formation of plaques for VSV-G*-ΔGrVSV-CCHFV-GPC, permitting growth kinetics assays and subsequent titrations. VSV-G*-ΔGrVSV-CCHFV-GPC replicated to highest titer around similar peak times for wild-type VSV titers, 16 hpi (FIG. 2A). Both ΔGrVSV-ΔCCHFV-GPC and CCHFV had peak titer, at approximately 36 hpi (FIG. 2A).

Figure 2:
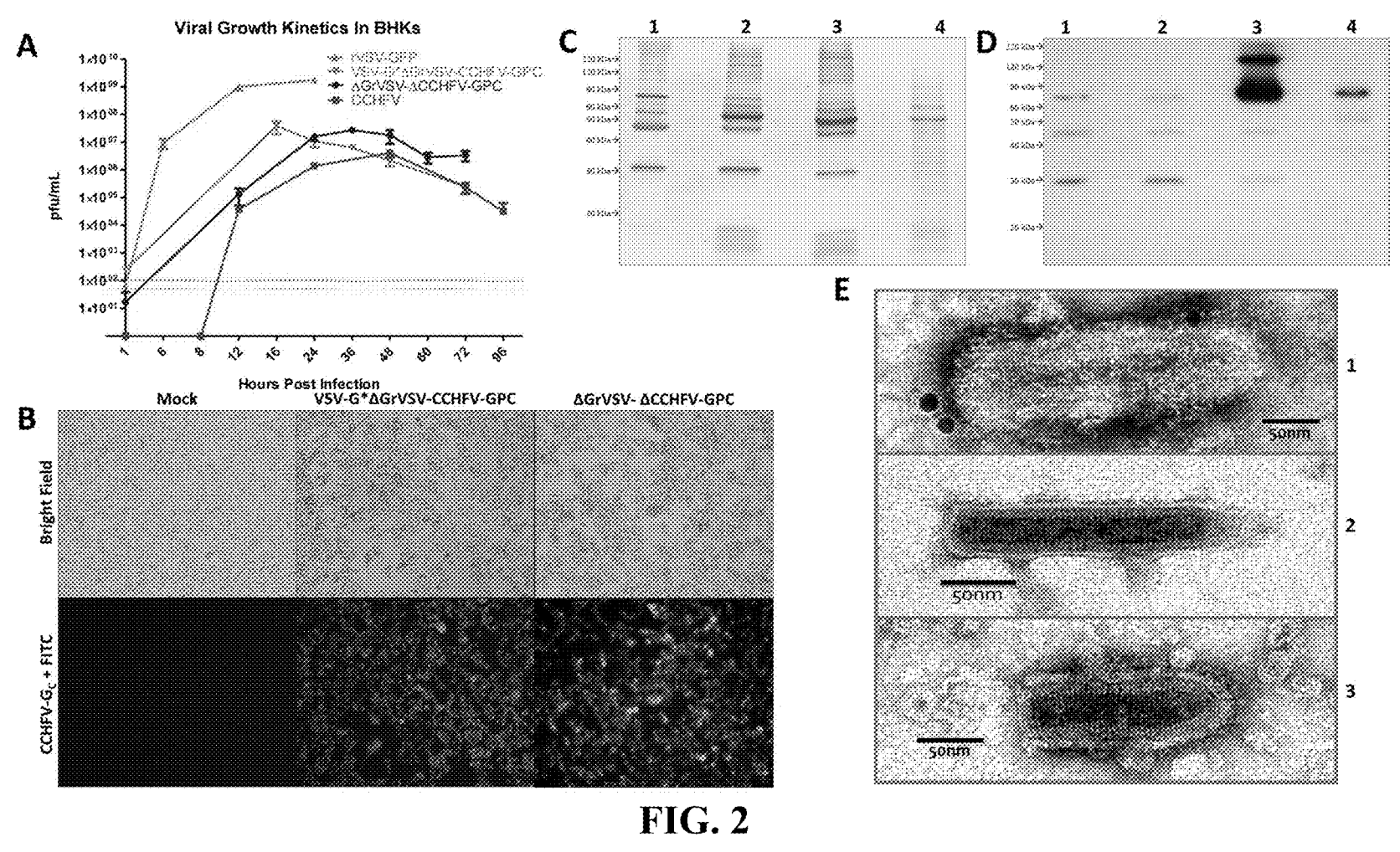
Figure 3:
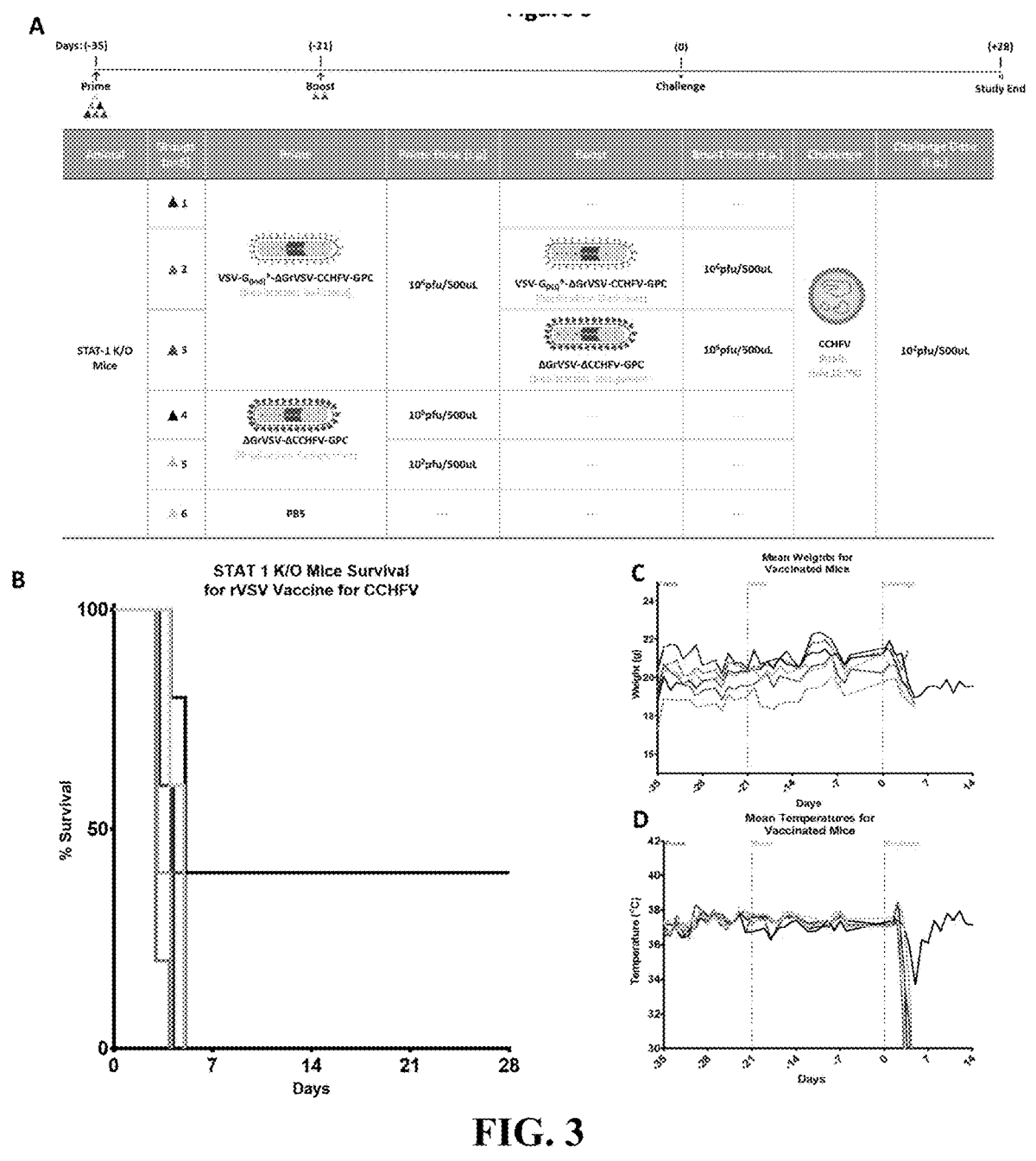

To assess the expression of the CCHFV-GPC in the ΔGrVSV-CCHFV-GPC vector, the inventors infected SW-13-CDC or BHK cells and performed immunofluorescence microscopy, using an antibody that binds to CCHFV-$G_C$, which revealed strong in vitro expression of CCHFV-$G_C$ antigen (FIG. 2B). The inventors additionally examined if CCHFV-$G_C$ was incorporated onto gradient purified rVSV virions, VSV-G*-ΔGrVSV-CCHFV-GPC and ΔGrVSV-ΔCCHFV-GPC, and semi-purified virions of both rVSV-GFP and CCHFV (as controls), by Coomassie staining and western blot analysis. Through Coomassie staining, differences in number and mobility of protein bands were detected among VSV-G*-ΔGrVSV-CCHFV-GPC and ΔGrVSV-ΔCCHFV-GPC. The two CCHFV-GPC recombinants both had additional protein bands below 20 kDa with analogous bands detected in CCHFV virion pellets (FIG. 2C, Lanes 2, 3, and 4). Both CCHFV-GPC recombinants also possessed more pronounced protein bands around 60 kDa, compared to our wt rVSV-GFP (FIG. 2C). CCHFV structural glycoproteins $G_N$ and $G_C$ present as bands of approximately at 37 kDa and 75 kDa, respectively, on SDS-PAGE gels. There was no observable $G_N$ band found on either CCHFV-GPC recombinant at 37 kDa, however, there were two distinct bands between 60-80 kDa in both recombinants (FIGS. 2C-2, -3). The VSV-G*-ΔGrVSV-CCHFV-GPC was expected to possess a VSV-G as one of these bands. The ΔGrVSV-ΔCCHFV-GPC did not encode for a VSV-G, nor would it be complemented with VSV-G after seven rounds of BHK passaging. A duplicate run protein gel was run and further probed by western blotting using a monoclonal antibody previously identified to be specific for CCHFV $G_C$ by western blot (Mab 11E7, BEI Resources) (14). These western blot data demonstrated limited, non-specific binding to three VSV proteins as observed in lanes rVSV-GFP and VSV-G*-ΔGrVSV-CCHFV-GPC (FIG. 2D, Lanes 1 and 2), but showed strong signal to at least two antigens at approximately 75 kDa and 150 kDa for ΔGrVSV-ΔCCHFV-GPC (FIG. 2D-3). Indicating that mature CCHFV-$G_C$ and potentially a precursor molecule or an oligomeric form of CCHFV-$G_C$ (due to the lack of β-mercaptoethanol in antigen preparations), are incorporated in/on ΔGrVSV-ΔCCHFV-GPC virions. The semi-purified CCHFV also showed limited non-specific binding to antigens at 57 kDa (CCHFV-NP) and 37 kDa (CCHFV-$G_N$), but distinct signal at 75 kDa (CCHFV-$G_C$) (FIG. 2D, Lane 4).

To examine the ultrastructure of the replication competent recombinant, ΔGrVSV-ΔCCHFV-GPC, transmission electron microscopy studies were conducted. Consistent with other rVSV pseudotyped with bunyavirus GP (28), our rVSV maintained rhabdovirus morphology and classical bullet shape with coiled intra-virion structure (FIG. 2E). Particles of ΔGrVSV-ΔCCHFV-GPC and VSV-G*-ΔGrVSV-CCHFV-GPC were observed to have lengths of particles ranging between 210-260 nm (FIG. 2E, Images 1 and 2). Particles of rVSV-GFP ('wild-type' VSV electron microscopy control) were observed between 170-200 nm (FIG. 2E, Image 3). This apparent length increase of the ΔGrVSV-ΔCCHFV-GPC and VSV-G*-ΔGrVSV-CCHFV-GPC is likely due to the genome containing approximately 4,000 extra nucleotides in comparison to the rVSV-GFP genome (which is also slightly larger than native wild-type VSV Indiana [GenBank number NC_001560.1]). Additionally, immunolabeling of ΔGrVSV-ΔCCHFV-GPC was employed with either CCHFV-$G_C$ MAb 11E7, 12A9, or 8A1 and counterstained with 15 nm gold conjugated secondary MAb (FIG. 2E, Image 1). Immunolabeling demonstrated labeling of $G_C$ spikes on the virion surface of ΔGrVSV-ΔCCHFV-GPC (FIG. 2E, Image 1).

With the data supporting that the replication deficient construct expressed CCHFV-GP in vitro and the replication competent construct additionally expressed CCHFV-$G_C$ on the surface of the virion, an in vivo study was designed to test the ability of either construct to function as an experimental vaccine. The STAT-1$^{-/-}$ mouse model for CCHFV was selected to test these constructs for safety and protective efficacy. A pilot study was designed to test a range of conditions, doses, and boosting response (FIG. 3A) as it was unclear whether the rVSV expressing CCHFV-GPC would be tolerated in the STAT-1$^{-/-}$ model. Similar rVSV vectors encoding Ebola and Marburg hemorrhagic fever virus GP, have resulted in lethal outcomes following vaccination of STAT-1$^{-/-}$ mice (43). Three groups of five mice were vaccinated with a prime dose of $10^6$ pfu of the replication deficient VSV-G*-ΔGrVSV-CCHFV-GPC construct. One of these groups was boosted at two weeks post prime with a $10^6$ pfu of the replication competent ΔGrVSV-ΔCCHFV-GPC. To avoid a limiting anamnestic response in the boosted replication deficient vaccinations, a VSV complemented with a different serogroup VSV-G (Indiana and New Jersey) between prime and boosting was also used, as previous studies have suggested immune responses can vary between serogroup VSV-G (44). This group was boosted with a $10^6$ pfu dose of VSV-$G_{NJ}$*-ΔGrVSV-CCHFV-GPC, where the in trans complemented VSV-G on the boosting was from the New Jersey VSV serogroup in comparison to prime (prime: Indiana, boost: New Jersey). Two additional groups were primed with the replication competent construct at a 'low' ($10^2$ pfu) and 'high' ($10^6$ pfu) dose of ΔGrVSV-ΔCCHFV-GPC. A final group of five STAT-1$^{-/-}$ mice in the pilot experiment was administered PBS for mock control purposes.

Mice were observed daily for 35 days for clinical signs, weights, and temperatures. All mice survived vaccination of prime and boost regimens, with no attributed fever, and approximately 5% weight loss observed in three of the five mice in the $10^6$ pfu replication competent group across two days (FIGS. 3C, 3D). All mice were challenged with 100 pfu of CCHFV strain IbAr10200 at 35 d post prime and monitored for weight and temperatures. Time-to-death for the animals occurred between 3-5 days post challenge for all groups. The $10^6$ pfu high dose of replication competent ΔGrVSV-ΔCCHFV-GPC had 40% observed survival while all other groups succumbed to CCHF (FIG. 3B).

A second experiment was designed to increase the prime only dose and incorporate a boost of only the replication competent virus (FIG. 4), as this was the sole construct to offer protection (40%) against the lethal challenge outlined from the first in vivo experiment shown in FIGS. 3A and 3B. For these experiments, the inventors challenged with a clinical strain, Turkey200406546, designated throughout this work as Turkey2004; which has previously been published in GenBank with the accession numbers KY362517 (S-segment), KY362519 (M-segment), and KY362515 (L-segment) (45). the inventors conducted NGS on our Turkey2004 isolate and found the genomes were highly similar to what had been published by Spengler et al (45). Our deep sequencing revealed four nonsynonymous mutations compared to aforementioned published sequences (S-segment: R68A, M-segment: R709A and A4039G, L-segment: A2804G). As our rVSV constructs were designed from a codon optimized GPC from the IbAr10200 strain, the inventors examined the GPC genomic alignments between the vaccination strain and challenge strain to assess the residue conservation among antigenic regions of the GPC between the IbAr10200 and Turkey2004 isolate.

Genomic alignments of all published (and complete) CCHFV-GPCs demonstrate 44.0% amino acid identity observed between all strains GPCs (Supplemental FIG. 2A). Despite Turkey2004 and IbAr10200 being from separate M-segment clades, lade V and III respectively, the genomic alignment demonstrates 84.4% identify between the GPCs of Turkey2004 and IbAr10200 (Supplemental FIG. 2B and Supplemental Table 2). Much of this variability is attributed to the non-structural components of the GP (Supplemental FIG. 2B). Further analysis revealed that the antigenic regions to be examined for countermeasure developments are largely the ectodomains of the structural $G_N$ and $G_C$ regions. These regions alone are conserved between the two isolates with 91.8% and 95.2% identity, respectively (Supplemental Table 2).

Figure 5:
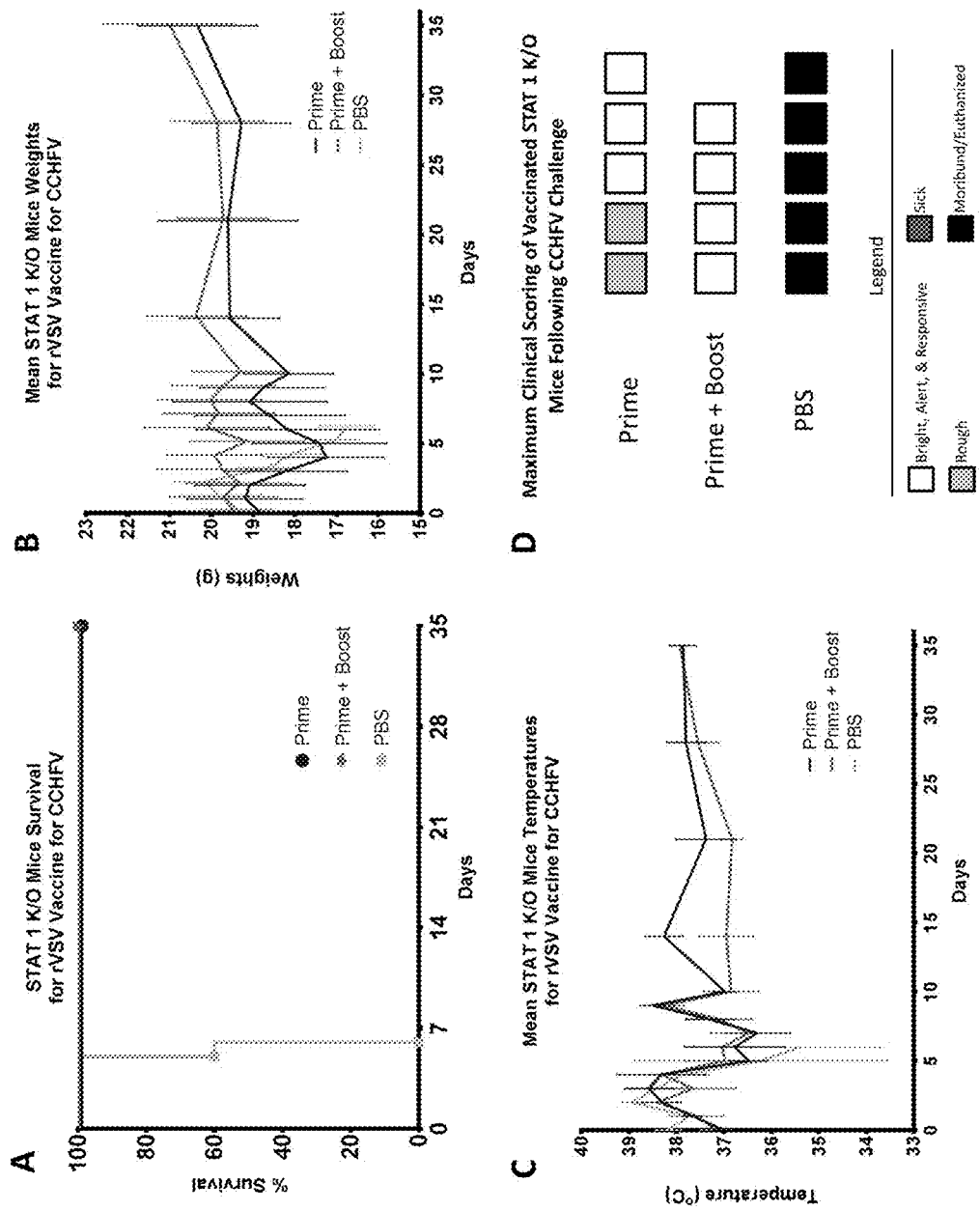
FIG. 5. Second in vivo experimental data: animal survival, average weights, average temperatures, and clinical scoring. (A) Kaplan-Meier survival curve of challenged animal groups. Group is indicated by color which corresponds to the colored triangles outlined in FIG. 4. (B) Averaged weights with error bars from all groups collected each day for 14 days post challenge and every 7 days after that for 35 days post challenge total. (C) Averaged temperature with error bars from all groups collected each day for 14 days post challenge and every 7 days after that for 35 days post challenge total. (D) The highest clinical scoring assigned to the mice is reported via colored boxes. White boxes indicate no clinical scoring (i.e., bright, alert, and responsive). Light grey boxes indicate mild illness with roughed appearance. Dark grey boxes indicate moderate to severe illness. Black boxes indicate moribund animals which were humanely euthanized per study protocols. The boosted group only had four animals due to a single animal succumbing for unknown reasons during the day of boosting.

Informed by the genetic alignment and conserved residue data between strains, the inventors proceeded to vaccinate two groups of five STAT-1$^{-/-}$ mice with the replication competent ΔGrVSV-ΔCCHFV-GPC construct at an increased dose of $10^7$ pfu and boosted one of these groups with the same construct and dose at 14 days post prime (FIG. 4). As a control, the inventors again used PBS as a mock vaccination. A single mouse succumbed in the boosted group (leaving only four mice to be challenged in the boosted group) the day of boosting. At 35 days post prime, all mice were challenged with 50 pfu of CCHFV strain Turkey2004 and were monitored for clinical signs, weights, and temperatures. For this CCHFV strain, the observed time-to-death was between five and six days post infection (dpi), as demonstrated with the PBS control group (FIG. 5A). For both prime and boosted groups, 100% protection was observed out to 35 dpi (FIG. 5A). All three groups displayed elevated temperatures for the first three days post challenge (FIG. 5B). The prime and PBS group displayed weight loss, while the boosted group did not (FIG. 5C). These results indicate that the primed group displayed a marked illness, while the boosted group displayed a milder form of illness post-challenge.

Figure 6:
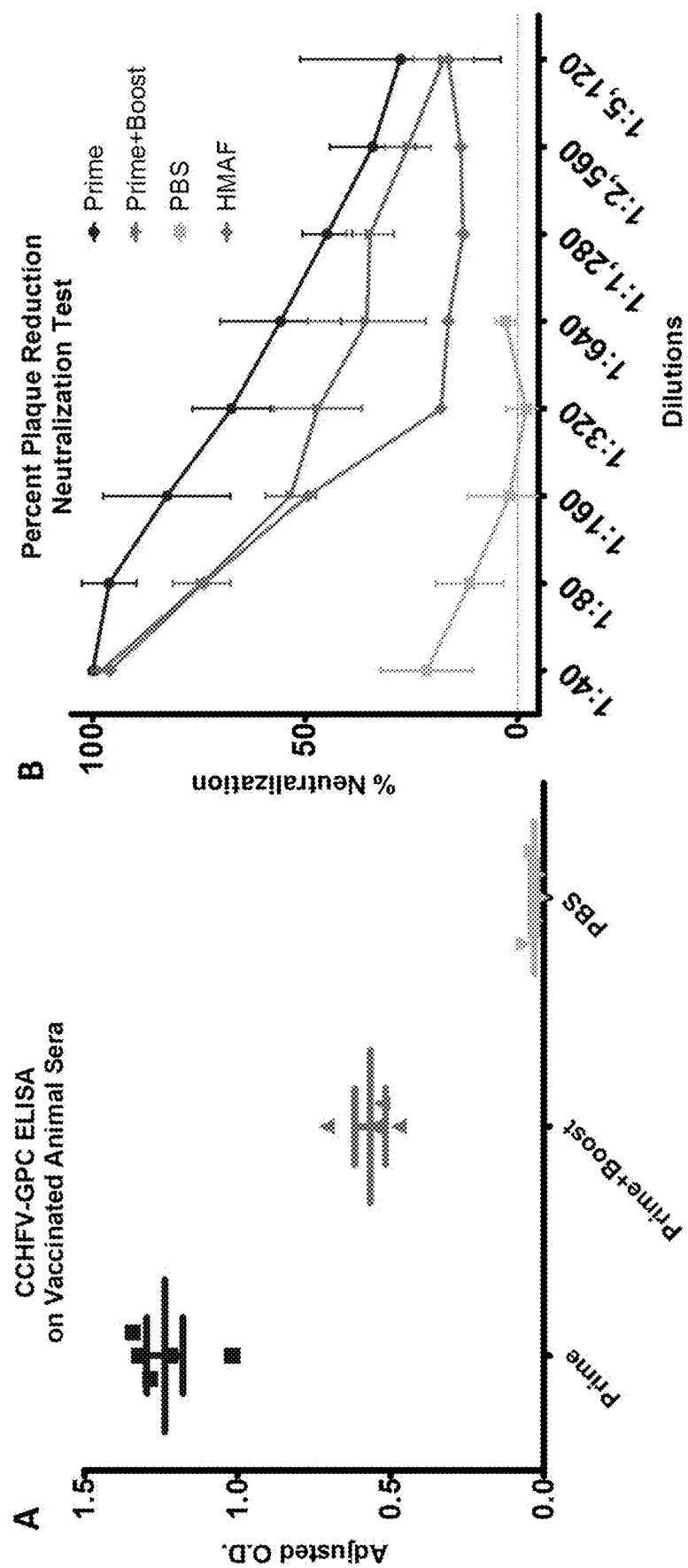
FIG. 6. Second in vivo experiment humoral immune responses. Study endpoint mouse sera collected from second in vivo experiment outlined in FIG. 5. Mice sera were run in duplicate with each group indicating four separate animal sera tested for humoral responses. (A) Enzyme linked immunosorbent assay (ELISA) using plates coated with 1 μg of purified rVSV-GFP and ΔGrVSV-CCHFV-GPC antigens. Adjusted OD values were calculated by subtracting VSV antigens (from rVSV-GFP coated ELISA plates) from ΔGrVSV-CCHFV-GPC coated ELISA plates. (B) Plaque reduction neutralization test (PRNT) from diluted endpoint sera with CCHFV (Strain: Turkey2004) incubated on SW-13-CDC cells. Hyperimmune mouse ascitic fluid (HMAF) was used as a positive control.

To examine the humoral response in mice, all groups were bled at study end points and sera were analyzed on an IgG ELISA for CCHFV-GP. Circulating IgGs to CCHFV-GP were detected in sera of both vaccinated groups (FIG. 6A). An adjusted optical density (OD) was reported for all tested sera to account for IgG response to VSV antigens. Curiously, the prime group displayed higher OD values (mean 1.25 OD) compared to the prime plus boosted group (mean 0.55 OD) (FIG. 6A). This indicates the prime only group had a higher concentration of IgG at the study endpoint which recognized CCHFV-GP, compared to the boosted group. The OD of the PBS group had negligible IgG responses to CCHFV-GP, with a mean value of <0.1 OD (FIG. 6A). To determine the neutralizing capacity of these sera, a plaque reduction neutralization test (PRNT) was carried out using the Turkey2004 challenge isolate. As depicted in FIG. 6B, the prime only group had neutralizing antibody titers with a PRNT$_{50}$ of <1:1,280 and the boosted group a PRNT$_{50}$ of <1:320 at the study endpoint (FIG. 6B). Our PRNT positive control, hyperimmune mouse ascitic fluid (HMAF) raised against CCHFV exposed mice, showed a PRNT$_{50}$ of <1:160 while the PBS control mice did not demonstrate a PRNT$_{50}$ value (FIG. 6B).

Additionally, at study endpoints for each cohort, the inventors examined tissues by immunohistochemistry (IHC) for CCHFV-NP antigen. The control cohort had marked CCHFV-NP immunolabeling in hepatocytes within the liver sections while liver sections from the prime only and boosted cohorts had no observable CCHFV-NP immunolabeling. The inventors further examined the spleen tissue sections and observed that the control cohort had marked CCHFV immunolabeling in mononuclear cells, and that the prime cohort had a cytoplasmic, mild, and diffuse immunolabeling of mononuclear cells primarily in the red pulp. The boosted cohort had no specific CCHFV immunolabeling within the spleen sections.

Studies have had varied success expressing CCHFV-GPC in trans on viral vectors (46, 47). rVSV with CCHFV-GPC has likely been challenging due to the numerous post-translational modifications required to mature, and provide functional, CCHFV-GPC (7, 8, 10, 12). Additionally, CCHFV-GPC form immature CCHFV particles at the Golgi and egress via vesicular transport (14, 39). Unlike CCHFV, VSV buds from the plasma membrane (40), which hampers efforts to recover a ΔGrVSV CCHFV-GPC vector. To approach this issue, the inventors used a mammalian codon optimized CCHFV-GPC (strain: IbAr10200). This platform has been observed to provided robust CCHFV GPC production in mammalian tissue culture (20), while maintaining native CCHFV maturation factors. The inventors hypothesized that higher expression due to codon optimization, could potentially result in shuttling of CCHFV-GP to the plasma membrane, where VSV could acquire and bud with functional components of the GPC in the viral envelope. Though, the inventors were able to drive strong expression CCHFV-GPC in vitro, the inventors were unable to generate a replication competent pseudotype without VSV-G* in trans. There have been multiple studies that have examined pseudotyping rVSV with a CCHFV-GPC using a plasmid encoding a VSVΔG backbone. A luciferase reporter pseudotype with in trans expression of the CCHFV-GPC was developed in 293T cells by Shtanko et al. (47). Suda et al., also did similar pseudotyping with in trans expression in 293T cells with various full length GPC and modified GPC constructs containing truncated $G_C$ C-terminal/endodomain tails (46). These pseudotypes also had a luciferase or GFP ORFS genomically encoded in the VSVΔG backbone (46). Both published pseudotyping CCHFV-GP*-ΔGrVSV systems had demonstrated functionality in examining neutralization and entry/infection studies, however, these constructs were not fully characterized by western blot or immune electron microscopy with respect to what was on the exterior of the pseudotypes; nor were either constructs self-replicating or capable of further expressing CCHFV-GP post infection (46, 47).

With the tools currently available for our analysis, the inventors were able to detect by western blotting and electron microscopy, a form of CCHFV-$G_C$ that was present and functional on the surface of the ΔGrVSV-ΔCCHFV-GPC virion. Immunolabeled electron micrographs demonstrated that CCHFV-$G_C$ was incorporated on the surface of the virion. While the inventors were able to immunolabel for CCHFV-$G_C$, PAGE and Coomassie staining analysis of our purified virion lysates, did not reveal prominent protein bands at the 37 kDa position, the estimated size of mature $G_N$. However, the inventors did have three smaller protein bands in our VSV-G*-ΔGrVSV-CCHFV-GPC and ΔGrVSV- ΔCCHFV-GPC preparations. Similar protein profiles have been shown in other CCHFV preparations, as shown by Buttigieg et al., 2014. Though, it is possible that these protein bands may also correspond to VSV-M2 and -M3 by alternative initiation at downstream start codons present in the ORF of VSV-M (48). While not the focus of this current study, these observations warrant further characterization if this vector is to be used as a tool to further study CCHFV-GPC mechanisms.

Suda et al., have shown an increase in the amount of infectious pseudotype the more the $G_C$ tail is truncated, up to a deletion of 53 residues at the end of the C-terminal $G_C$ tail (46). Our data supports this region as a probable, or at the very least, contributory mechanism which enables the replication competent ΔGrVSV-ΔCCHFV-GPC pseudotype formation (FIG. 1B). There is likely a localization or retention signal within the transmembrane region or endodomain tail which is aberrated and fails to shuttle $G_C$ to solely the intracellular compartments and this perhaps allows shuttling to the plasma membrane. Once again this is not the focus of this study, though it will be examined in the future. It is interesting to note, that a similar motif has been demonstrated by other bunyaviruses (49, 50) and has also been demonstrated with other VSV pseudotypes (51). Structural $G_C$ alone has been examined to have putative receptor binding, a class II viral fusion domain, soluble/shed oligomeric forms of $sG_C$, a characterized neutralization domain, and human linear B-cell epitope sites (7, 10, 13, 52-54). Our replication competent rVSV vector can enable exploration of these components at lower containment (BSL-2), without the need for transfections for in trans expression of CCHFV-GPC onto VSVΔG systems.

When exploring the use of rVSV expressing CCHFV-GP as potential vaccines, there was a concern of murine virulence, which has been observed for wild-type VSV (55, 56). Studies with rVSV expressing hemorrhagic fever virus GP have also demonstrated lethal outcomes in the STAT-1$^{-/-}$ model (43). This has hampered the STAT-1$^{-/-}$ animal platform from serving as a vaccine development tool, as 'vaccinated' mice succumb to a prime dosing (43). Because of this information, in our studies (FIG. 3A) the inventors tested three doses at $10^7$, $10^6$ and $10^2$ pfu, for our replication competent ΔGrVSV-ΔCCHFV-GPC construct and selected a traditional $10^6$ pfu dose for our replication deficient VSV-G*-ΔGrVSV-CCHFV-GPC construct. Demonstrating the safety profile of both constructs, no group had any attributed fatality due to the vaccines.

In pilot studies (FIG. 3A) the time-to-death for challenged mice, ranged between 3-5 dpi (FIG. 3B). The inventors hypothesized that time-to-death was occurring too rapidly in our model due to our challenge virus, CCHFV isolate IbAr10200, and may be overwhelming the immune response too quickly. The IbAr10200 strain has been widely used as the prototype strain for CCHFV research, despite it being passaged substantially in mice and without any record of human disease. The IbAr10200 strain used in this study has a documented history of thirteen passages in suckling mice, plus several passages in Vero and SW-13-CDC cell cultures. These passages, specifically in suckling mice, may have induced murine adaptation and enhanced virulence in the STAT-1$^{-/-}$ model. The history behind the IbAr10200 strain also reveals that this strain was isolated from a tick which had engorged on a camel and has no associated human clinical disease attributed (57). As there is ongoing debate in the field about the pathogenicity among circulating CCHFV strains (3, 58-60), a human/clinical isolate with lower passage history may be more pertinent at evaluating medical countermeasures. Additionally, our unpublished studies have shown that certain CCHFV isolates, particularly isolates from human/clinical cases, have a delayed time-to-death in the STAT-1$^{-/-}$ murine model, compared to the prototype CCHFV isolate IbAr10200. To delay time-to-death in the model, the inventors decreased the challenge dose and changed the CCHFV challenge strain to a human clinical disease isolate. Based on CCHFV isolate availability, the inventors selected an isolate with a much lower passage history, clinical relevance (i.e., documented history of disease in humans), and one that has a prolonged time-to-death in the STAT-1$^{-/-}$ mouse model, relative to the IbAr10200 isolate. Our Turkey2004 strain has a lower passage history of four passages in Vero cells and one in SW-13-CDC cells with no passaging in murine tissues and has only four nucleotide changes in the genome when compared to the Genbank published Turkey 2004 isolate (45). Despite the geographic and phylogenetic clade differences between Turkey2004 and IbAr10200, the inventors hypothesized that there is residue conservation in the GPC in general, but a high degree of residue conservation among the antigenically important regions of the $G_N$ and $G_C$. As our genomic analysis demonstrates, the GPC contains approximately 84% amino acid variability between the IbAr10200 and Turkey2004 strains. However, the true variability of the structural proteins encoded on the M-segment is more conserved (>90%) and thus have lower residue variability. Altering the strain with a less passaged and human/clinical isolate, prolonged the time-to-death window to up to 7 days. This challenge strain switch and increasing the prime dosing improved our initial 40% protection (FIG. 3B) to 100% protection (FIG. 5A) in vaccinated mice. It is curious to speculate that if structural components of the CCHFV-GPC are preferred antigens for CCHFV vaccine design, than a multiple clade vaccine approach might be feasible for cross protection between circulating strains and across geographic areas. As our construct expressed a notable and useable form of CCHFV-$G_C$, and elicited a protective response against two strains, additional countermeasure studies regarding this structural GP should also be explored.

ELISA and PRNT experiments on study endpoint sera, demonstrate a humoral IgG response to CCHFV-GPC with observed neutralizing antibodies produced from the prime group that received a high ($10^7$ pfu) dose of ΔGrVSV-ΔCCHFV-GPC (FIGS. 6A, 6B). Curiously, our boosted ($10^7$ pfu) group had lower detectable antibodies to the CCHFV-GPC with lower neutralization titers (FIGS. 6A, 6B). Clinical data for these groups following CCHFV challenge show that the prime only group had elevated temperatures and weight loss, indicating illness from the CCHFV challenge (FIGS. 5B, 5C, 5D). While the boosted group did display elevated temperatures, there was neither substantial weight loss detected nor clinical scoring (FIGS. 5B, 5C, 5D). Further analysis of tissues at study end point for these cohorts, also revealed that while there was no immunolabeling in the liver of the vaccinated animals the prime cohort had diffuse cytoplasmic immunolabeling of mononuclear cells in the spleen sections (FIG. 7E), suggesting, along with the clinical scores, that there was more replication of CCHFV in this group compared to the boosted group. This could potentially lead to the higher anti-CCHFV-GPC IgG titers in the prime cohort at the study endpoint as the CCHFV challenge may have "boosted" these levels when compared to the boost cohort. Regardless, protection was achieved by both regimens, though the boosted group data supports the notion that at study endpoint, the observed IgG titers against CCHFV-GPC along with lower neutralizing titers (PRNT$_{50}$ of <1:320) are sufficient in combating lethal CCHFV infection in the STAT-1$^{-/-}$ mouse model.

Correlates of protection against CCHF have been difficult to define due to the multiple vaccine and delivery platforms examined to date, along with the lack of an immunocompetent animal model (16). Several CCHFV experimental vaccines studies have identified cell-mediated and humoral involvement, with some instances of neutralizing antibody production (24, 61). In looking at what is known for human CCHF, survivors mount a humoral response whereas those who succumb, typically lack an IgG response (3). Other studies have examined antibody and neutralizing responses from the various vaccine platforms. DNA vaccines following a three round vaccination regimen have induced detectable antibodies with neutralizing capacity observed up to 1:160 in PRNT dilutions and achieved 100% protection, depending on the antigens encoded on the DNA plasmids (25, 62). A cell culture based inactivated virus vaccine achieved high IgG titers (1:102,400) and a high neutralizing response of 1:1,024, however, this also required three vaccination rounds, an alum adjuvant, and conferred 80% protection against the clinical isolate Turkey-Kelkit06 in IFNAR mice (21). Antibody titers, neutralization capacity, and challenge virus presented here were similar, though through the VSV platform, the inventors achieved greater protection with a single dose. These studies suggest other facets of the immune system are likely involved in conferring complete protection.

A limitation of our study is that T cell responses were not evaluated, and could be contributory as other groups have shown (23, 25, 26). Future studies, serially examining the antibody and T cell repertoire after prime and boosting doses following ΔGrVSV-ΔCCHFV-GPC and VSV-G* ΔGrVSV-CCHFV-GPC, but before CCHFV challenge, would be informative for the STAT-1$^{-/-}$ mouse model. Though the relevance and value of the immune response in immunodeficient mice, like STAT-1$^{-/-}$ or IFNAR following CCHFV infection, in relation to actual immune response during human CCHF, ultimately remains unclear. In the future, the use of the IS murine model might provide a more intact immune system to model lethal CCHFV in, to better determine murine correlates of protection (20). Further, an immunocompetent, larger animal model is much needed in the CCHF field to further test the array of CCHFV experimental vaccines which have shown promise in these mouse models.

In conclusion, this study offers not only a tool to study the biology off CCHFV as it relates to structural G$_C$, but also serves to develop and characterize two vectors, one replication deficient and one replication competent, in relation to CCHF vaccine development. The replication competent construct provides limited protection if used with murine adapted challenge strains of CCHFV, but demonstrates 100% protection and a robust humoral response, with a single-injection when the challenge strain is a low passaged, human clinical isolate. This information is valuable in designing future studies in CCHFV animal models, and establishes characterized tools to examine the biology of structural CCHFV-G$_C$ in a pseudotyped rVSV system.

B. Materials and Methods

Cell culture, challenge virus, and antibodies. Baby hamster kidney cells (BHK) (kindly provided by M. Whitt, University of Tennessee Health Science Center, Memphis, Tenn.), African green monkey kidney E6 clone cells (Vero E6) (American Type Culture Collection [ATCC], Manassas, Va.), a clone from the SW-13 human adrenocortical carcinoma cell line (SW-13-CDC), (kindly provided by É. Bergeron of Centers for Disease Control and Prevention, Atlanta, Ga.) were maintained in Dulbecco's modified Eagle's medium (DMEM) supplemented with 10% fetal bovine serum (FBS; Invitrogen, Carlsbad, Calif.), 2 mM L-glutamine (Invitrogen), and 1% penicillin-streptomycin (P/S; Invitrogen), cumulatively called D10. CCHFV challenge stocks, strains IbAr10200 and Turkey-200406546 [referred as Turkey2004, throughout] (kindly provided by T. Ksiazek, UTMB—World Reference Center for Emerging Viruses and Arboviruses, Galveston, Tex.), were propagated in Vero E6 cells once, plus previous passages in suckling mice and Vero cells since isolation. All in vitro and in vivo work with CCHFV was performed in a biosafety level 4 facility at the Galveston National Laboratory, University of Texas Medical Branch, Galveston, Tex. All cell and viral stocks were tested and free of *mycoplasma*, by PCR kit (IntronBio, Gyungg-Do, South Korea). Monoclonal antibodies (MAb) mouse-α-CCHFV-G$_C$ 11E7, 8A1, and 12A9, and mouse-α-CCHFV-G$_N$ antibody 6B12 were generated and characterized as described previously (13, 14). Described antibodies are available at BEI Resources (ATCC) except for 8A1, which was kindly provided by United States Armed Forces Research Institute for Infectious Diseases, Frederick, Md.

Generation of ΔGrVSV-CCHFV-GPC vectors. The rVSV vector was cloned and recovered from cDNA as previously described (63). Briefly, a BlueScript backbone plasmid under T7 polymerase promoter control encoding a ΔG, VSV Indiana backbone expressing a chimeric Zaire ebolavirus (ChEBOV) glycoprotein (GP), was used as the vector (designated pVSVΔG-ChEBOV-GP-3). This plasmid was modified by cutting out an existing ChEBOV-GP coding sequence via MluI and NheI restriction sites, yielding a pVSVΔG vector. An insert, coding for the codon optimized open reading frame of the complete CCHFV glycoprotein precursor (GPC), was digested and ligated into the pVSVΔG vector. The CCHFV-GPC insert was created by overhang PCR mutagenesis; flanking a 3' MluI restriction site plus Kozak sequence, and a 5' XbaI restriction site, from a PCR amplified, codon optimized, pCAGG-CCHFV-GPC (kindly provided by J. Kortekaas, Central Veterinary Institute, Lelystad, Netherlands). This ligated and cloned plasmid, designated pVSVΔG-CCHFV-GPC, was transfected into BHK cells that were also co-transfected with VSV protein N, P, G, and, L 'helper' plasmids under T7 promoter control and driven by infection (MOI 5) with recombinant vaccinia virus expressing T7 polymerase (rVV-TF7-3; kindly provided by M. Whitt). Recovered virus, designated VSV-G*-ΔGrVSV-CCHFV-GPC, was collected 24-48 hrs post infection/transfection, filtered twice through a 0.2 µm filter to remove vaccinia virus, plaque purified onto VSV-G* complemented BHK cells, and stored at −80° C. for further use. All plasmid maps and cloning primer sequences are available upon request.

Infections, enumeration, growth kinetics, and preparation of viral material. For infections of replication deficient vector, semi-confluent (~60-80%) monolayers of BHK cells were transfected with 1 µg/1×10$^6$ cells using either pCAGG-VSV-G$_{(Indiana)}$ or pCAGG-VSV-G$_{(New\ Jersey)}$. Once monolayers displayed cell rounding and syncytia, they were infected at an MOI of 0.1 with VSV-G*-ΔGrVSV-CCHFV-GPC. Supernatants were harvested at 24 hrs post infection (hpi) and clarified at 2,000 rpm for 10 min at 4° C. Confluent monolayers of BHK cells were infected with replication competent ΔGrVSV-ΔCCHFV-GPC at MOI 0.1 for 1 hr at 37° C. with 5% CO$_2$ with rocking at 15 min intervals and harvested/clarified at 48 hpi. Plaque assays for viral titrations were carried out in an analogous manner, with an overlay media final concentration of 1.25% Avicel (Sigma-Aldrich, St. Louis, Mo.) in 1× Eagles minimum essentials medium (MEM) with 5% FBS and 1% P/S on BHK cells for 24-48 hpi. After incubations, overlays were aspirated and a 10% buffered formalin fix with a 1× crystal violet stain was incubated onto monolayers for one hr. Plaques were enumerated and plaque forming units (pfu) were determined by averaging technical replicates per sample. Single-cycle growth curves at MOI 0.1 were performed by absorbing rVSV-GFP, VSV-G*-ΔGrVSV-CCHFV-GPC, ΔGrVSV-ΔCCHFV-GPC, or CCHFV onto duplicate monolayers of BHK cells in six-well plates as described above. Inoculum was aspirated, cells were washed three times with PBS, and D5 was added to monolayers and incubated at various time points indicated in FIG. 2A. At designated time points, samples were collected and stored at −80° C. until titrations were performed described above.

CCHFV-$G_C$ protein analysis. Immunofluorescence analysis was carried out by infecting SW-13-CDC and BHK monolayers at an MOI of 0.1 for 24 and 48 hpi, respectively. Cells were fixed with 4% (w/v) paraformaldehyde, permeabilized with 1% Triton X-100 and stained with 1:500 diluted MAb 8A1. Cells were washed, blocked with 5% BSA, and incubated with a dilution of 1:1,000 secondary goat-α-mouse MAb conjugated to an AlexaFluor488 (Invitrogen). Stained cells were examined on a Nikon Eclipse Ti-S fluorescence microscope. Whole virions were analyzed by infecting BHK cell monolayers, semi-purifying clarified supernatants over a 20% sucrose cushion at 37,000 rpm for 45 min at 4° C. using a Beckman SW 41 Ti rotor. Viral pellets were lysed using NP-40 with 1× Protease Inhibitor Cocktail (Invitrogen). Recombinant VSV lysates were incubated at 56° C. for 10 min and protein subsequently quantified using BCA Protein Assay per manufacturers' instructions (Thermo Fisher Scientific, Waltham, Mass.). Per institutional inactivation protocols, CCHFV lysates had a modified inactivation protocol using instead 2× Laemmli Sample Buffer (LSB) (Thermo Fisher Scientific) at 95° C. for 15 min boiling and transfer to a fresh tube. Approximately 200 ng of purified and semi-purified virion associated total protein was mixed 1:1 with 1×LSB (without β-mercaptoethanol) and run on 4-20% gradient Mini-PROTEAN TGX electrophoresis gels (Bio-Rad, Hercules, Calif.). Coomasie staining was accomplished via incubating TGX gels in Coomassie Fluor Orange protein gel stain (Thermo Fisher Scientific) per manufacturers' instructions and imaged at 300 nm on a Gel Doc XR+ gel documentation system (BioRad). Western blots were run on TGX gels using wet tank transfer to Hybond-P polyvinylidene difluoride (PVDF) membranes (GE Healthcare, Little Chalfont, UK). Membranes were blocked with 5% BSA overnight at 4° C. in Tris/0.1% Tween 20 (Sigma-Aldrich) followed by incubation with primary MAb 11E7 diluted at 1:1,000, overnight at 4° C. Secondary horse radish peroxidase (HRP) conjugated goat-α-mouse antibody (Thermo Fisher Scientific) was diluted 1:10,000 and incubated on the membrane for 1 h at room temperature. Detection of HRP was accomplished via Pierce ECL western blotting substrate (Thermo Fisher Scientific), Hyperfilm ECL (GE Healthcare), and Kodak Carestream film with X-OMAT 2000 Processor (Eastman Kodak Company, Rochester, N.Y.).

RNA purification, cDNA creation, and Sanger sequencing analysis. Clarified viral supernatants were placed in TRIzol LS (Thermo Fisher Scientific) at a ratio of 1:5, mixed, incubated for 10 min at room temperature, and transferred to fresh tubes. RNA was isolated from sample mixtures using Zymo Research Direct-zol RNA min-prep (Zymo Research Corp, Irvine, Calif.), per manufacturers' instructions. RNA was quantified using a NanoDrop 8000 (Thermo Fisher Scientific) and approximately 500 ng total RNA was used to create cDNA using the SuperScript III First-Strand Synthesis System (Invitrogen) and a VSV-M, matrix protein gene 3' forward primer. Sanger sequencing on the cDNA was performed using VSV-M, VSV-L, and CCHFV-GPC (codon optimized) open reading frame primer sets and accomplished by the UTMB Molecular Genomics Core using an ABI Prism 3130XL DNA Sequencer (Applied Biosystems, Foster City, Calif.). Sequence analysis was performed using Geneious R9 (Biomattes, Auckland, New Zealand) based on consensus and plasmid maps. All cDNA/sequencing primers and consensus/plasmid maps are available upon request.

Deep sequence analysis of viral RNA genomes. To analyze the stocks of CCHFV or rVSV vaccine vectors used in this study the inventors performed deep sequencing analysis of RNA isolated from these virus stocks. Briefly, viral RNA was isolated from a Trizol LS (Invitrogen)/sample mixture using a Direct-zol RNA mini-prep (Zymo Research), per manufacturer's instructions. Approximately 150 ng of purified RNA was used to make cDNA using the Ovation RNA-seq 2.0 kit (NuGen) and this in turn was used for the preparation of the double-stranded DNA library, using Encore Ion Torrent library prep kit. Sequencing was performed by the UTMB Molecular Core on the Ion Torrent using 318-v2 deep sequencing chips. Sequence analysis was performed using DNA Star Seqman NGen software (DNA Star) based on unpaired analysis of 125 base pair overlaps.

Ultrastructural analysis. Viruses were propagated in multiple T-150 flasks of confluent BHK cells. Viral supernatants were harvested and clarified as described above. Clarified supernatants were concentrated by mixing with buffered 4× polyethylene glycol with incubation for 4 hrs at 4° C., followed by centrifugation at 6,800×g for 30 mins at 4° C. Concentrated pellets were re-suspended in PBS with protease inhibitor and overlaid atop Optiprep (Sigma-Aldrich) continuous gradients of 6-48% buffered iodixanol. Viruses were banded by ultracentrifugation at 25,000×g for 15 hrs at 4° C. using a SW 41 Ti rotor. Bands were harvested, washed in PBS, and pelleted at 27,000×g for 1 h at 4° C. using a SW 41 Ti rotor to remove residual iodixanol. Purified viral pellets were re-suspended in PBS and absorbed onto Formvar-carbon coated nickel grids (Electron Microscopy Sciences [EMS], Hatfield, Pa.) for 10-30 mins, incubated with MAb 11E7, 12A9, or 8A1 at 1:10 dilutions. Antibodies were absorbed for 30 mins in wet chamber and washed with PBS containing 1% BSA, and incubated with the secondary antibody, goat-α-mouse conjugated to 15 nm colloidal gold particles (EMS), at a dilution of 1:20 for 30 mins. Grids were washed with PBS and 1% BSA, and fixed using 2% (w/v) aqueous glutaraldehyde for 10 mins and stained with 2% (w/v) aqueous uranyl acetate. Grids were examined at 60 kV using a Philips CM-100 transmission electron microscope.

Ethics of care, vaccination, and animal challenge. Animal studies were approved by the UTMB Institutional Animal Care and Use Committee (IACUC). Animal research was carried out in compliance with the Animal Welfare Act and other federally regulated stipulations regarding animals and adherences to the *Guide for the Care and Use of Laboratory Animals*, National Research Council, 2013. The animal facilities where this research was conducted are accredited by the Association for Assessment and Accreditation of Laboratory Animal Care International. This study used female 4 to 8 weeks old 129S6/SvEv-Stat1$^{tm1Rds}$ mice (STAT-1$^{-/-}$) (Taconic, Germantown, N.Y.). After an acclimatization period in barrier conditions in environmentally enriched sterile housing etc., mice were anesthetized by isoflurane and implanted with subdermal transponders, which provide coded identifiers and permitted body temperature measurements (Biomedic Data Solutions, Seaford, Del.). Vaccine preparations were diluted in Hanks balanced salts medium with 4% FBS, along with PBS for control groups. After anesthesia by isoflurane, 500 ul of each preparation was split and administered in two locations intraperitoneally (i.p.) on either side of the mouse, with five STAT-1$^{-/-}$ mice per experimental group. Mice were observed twice daily for one-week post vaccinations, and once daily thereafter. Clinical scoring, body temperature, and weight in grams, were recorded daily. Mice were brought into ABSL-4 several days prior to challenge to permit further acclimatization. At 35 days post vaccination (prime), mice were challenged with 500 ul i.p. with either 100 pfu or 50 pfu of CCHFV-Ibar10200 or CCHFV-Turkey200406546 (referred to as Turkey2004), respectively. All challenge doses were frozen for storage and verified by back-titrations by plaque assay on SW-13-CDC cells as outlined in previous methodology sections. After challenge, animals were observed twice daily for clinical scoring, temperature, and weight change for two weeks, and once daily thereafter. Upon humane endpoint scoring, or study end-points, euthanasia was carried out by isoflurane anesthesia and terminal blood collection via cardiac puncture or retro-orbital bleeding, followed by CO2 overdose. Blood was collected and plasma and serum were separated by centrifugation and frozen for storage and further analysis.

Anti-CCHFV-GPC IgG ELISA development. Iodixanol gradient purified ΔGrVSV-ACCHFV-GPC and rVSV-GFP were re-suspended in NP-40 buffer and BCA protein quantified (previously described above) and were used as whole virion antigens in coating Immunosorbent 96-well plates (Thermo Fisher Scientific). Matrices of various antigen, blocking, primary antibodies (hyperimmune mouse ascitic fluid [HMAF kindly provided by T. Ksiazek], 8A1, and 11E7) to CCHFV/CCHFV-GPC, and secondary antibody (MAb HRP-goat-α-mouse) concentrations were used to develop optimal detection conditions for the CCHFV-GPC via ELISA. Per optimizations, one microgram of purified antigen per mL was suspended in sterile filtered sodium bicarb/carbonate buffer (pH 9.6) and allowed to incubate on immunosorbent plates overnight at 4° C. Plates were washed with PBS containing a concentration 0.1% tween-20 and 0.001% thimerosal. Blocking occurred with 5% milk dissolved in wash buffer, for 2 hrs at room temperature. Sera from STAT-1$^{-/-}$ mice was added 1:100 and diluted 2-fold by pipetting across plates and allowed to incubate for one hr at 37° C. Plates were washed and a secondary anti-mouse antibody conjugated to HRP was added at 1:5,000 dilution for one hr at 37° C. ABTS Peroxidase substrate (KPL, SeraCare Life Sciences, Milford, Mass.) was incubated for 15 mins at room temperature prior to the addition of a 1% SDS stop solution. Plates were read with nine reads per well at 405 nm with a plastic correction factor accounted for from a 490 nm reading per well. Test sera was evaluated for both purified ΔGrVSV-ΔCCHFV-GPC and rVSV-GFP antigen response and resulting adjusted optical density (O.D.) values were adjusted by subtracting rVSV-GFP O.D. values from ΔGrVSV-ΔCCHFV-GPC O.D. values.

Plaque reduction neutralization assay. Serial dilutions of sera from four mice per treatment group, were aliquoted into cluster tubes with D10 and allowed to incubate with 100 pfu of CCHFV, isolate Turkey 2004, for approximately 2 hrs on ice. Resulting sera plus virus mixture was then overlaid onto 6-well plates of confluent SW-13-CDC cells and absorbed for 1 hr at 37° C. with 5% CO2 with rocking at 15 min intervals. Plaque assays were carried out in a manner described above in previous methods section. Resulting plaques were enumerated and compared to sera plus media only wells run for each sample, and a percent neutralization was calculated and reported for each dilution. Hyperimmune mouse ascitic fluid [HMAF] raised against CCHFV was additionally serially diluted and run as a positive control.

Immunohistochemistry of tissues. Tissue sections were deparaffinized and rehydrated through xylene and graded ethanols. Slides went through heat antigen retrieval in a steamer at 95° C. for 20 mins in Sigma Citrate Buffer, pH6.0, 10× (Sigma Aldrich, St. Louis, Mo.). To block endogenous peroxidase activity, slides were treated with a 3% hydrogen peroxide and rinsed in distilled water. The tissue sections were processed for IHC using the Thermo Autostainer 360 (ThermoFisher, Kalamazoo, Mich.). Sequential 15 min incubations with avidin D and biotin solutions (Vector, Burlingame, Calif.) were performed to block endogenous biotin reactivity. Specific anti-CCHFV immunoreactivity was detected using a primary polyclonal rabbit-α-CCHFV-NP antibody (IBT BioServices, Rockville, Md.) at a 1:3200 dilution for 60 mins. A secondary biotinylated goat-α-rabbit-IgG (Vector Laboratories, Burlingame, Calif.) at 1:200 dilution for 30 mins followed by Vector Horseradish Peroxidase Streptavidin, R.T.U (Vector) for 30 mins. Slides were developed with Dako DAB chromagen (Dako, Carpenteria, Calif.) for 5 mins and counterstained with Harris hematoxylin for 30 seconds. Tissue sections from uninfected mice were used as negative controls.

Statistical analysis. Statistical analysis of viral titers was performed using unpaired t-test with a 95% confidence level (P<0.05) and for survival, aKaplan-Meier survival curve with GraphPad Prism software (Graphpad Software, Inc., San Diego, Calif.).

The invention claimed is:

1. A replication competent recombinant Vesicular Stomatitis Virus (rVSV) vector comprising a VSV glycoprotein deficient VSV (ΔGrVSV) genome encoding a Crimean-Congo Hemorrhagic Fever virus (CCHFV) glycoprotein precursor (GPC)(ΔGrVSV-CCHFV-GPC).

2. The vector of claim 1, wherein the nucleic acid sequence encoding the CCHFV-GPC is codon optimized.

3. The vector of claim 1, wherein the nucleic acid sequence encoding the CCHFV-GPC is 90% identical to the nucleic acid sequence of SEQ ID NO:2, SEQ ID NO:4, or SEQ ID NO:6.

4. The vector of claim 1, wherein the nucleic acid sequence encoding the CCHFV-GPC is identical to the nucleic acid sequence of SEQ ID NO:2, SEQ ID NO:4, or SEQ ID NO:6.

5. The vector of claim 1, wherein the CCHFV-GPC protein has an amino acid sequence that is 95% identical to the amino acid sequence of SEQ ID NO:5, SEQ ID NO:7, or SEQ ID NO:8.

6. The vector of claim 1, wherein the encoded CCHFV-GPC has an amino acid sequence of SEQ ID NO:5, SEQ ID NO:7, or SEQ ID NO:8.

7. The vector of claim 1, wherein the ΔGrVSV-CCHFV-GPC vector has a nucleic acid sequence that is 90% identical to SEQ ID NO:1 or SEQ ID NO:4.

8. The vector of claim 1, comprised in an expression cassette.

9. The vector of claim 8, wherein the expression cassette is comprised in a plasmid vector.

10. A recombinant Vesicular Stomatitis Virus (rVSV) comprising a Crimean-Congo Hemorrhagic Fever virus (CCHFV) glycoprotein (rVSV-CCHFV-GP) $G_N$ and/or $G_C$.

11. A vaccine composition comprising the virus of claim 10.

12. A method of producing an immune response in a mammal comprising administering one or more of the vector of claim 1, the virus of claim 10, or the vaccine of claim 11 to a mammal.

13. The method of claim 12, wherein the mammal is a human.

14. The method of claim 12, wherein the vector is administered by injection, inhalation, or instillation.

15. A method for producing a replication competent recombinant Vesicular Stomatitis Virus comprising a Crimean-Congo Hemorrhagic Fever virus glycoprotein precursor vector (ΔGrVSV-CCHFV-GPC) comprising the step of passaging a VSV glycoprotein complemented recombinant Vesicular Stomatitis Virus encoding Crimean-Congo Hemorrhagic Fever virus glycoprotein precursor (VSV-G*-ΔGrVSV-CCHFV-GPC) in a non-complementing VSV glycoprotein cell line and isolating a replication competent ΔGrVSV-CCHFV-GPC vector.

16. A method of producing replication competent recombinant Vesicular Stomatitis Virus comprising a Crimean-Congo Hemorrhagic Fever virus glycoprotein virus (ΔGrVSV-CCHFV-GP), comprising infecting a cell culture with the isolated replication competent ΔGrVSV-CCHFV-GPC vector and isolating ΔGrVSV-CCHFV-GP virus produced by the infected cells.

17. A kit comprising one or more of (a) at least one dose of a replication competent recombinant Vesicular Stomatitis Virus comprising a Crimean-Congo Hemorrhagic Fever virus glycoprotein precursor vector (ΔGrVSV-CCHFV-GPC) of claim 1; or (b) at least one dose of a replication competent recombinant Vesicular Stomatitis Virus comprising a Crimean-Congo Hemorrhagic Fever virus glycoprotein virus (ΔGrVSV-CCHFV-GP) of claim 9.

18. A method for identifying a subject infected with or exposed to Crimean-Congo Hemorrhagic Fever virus comprising the steps of:
    (a) contacting a biological sample with a recombinant Vesicular Stomatitis Virus comprising a Crimean-Congo Hemorrhagic Fever virus glycoprotein virus (ΔGrVSV-CCHFV-GP) or a cell expressing a recombinant Vesicular Stomatitis Virus comprising a Crimean-Congo Hemorrhagic Fever virus glycoprotein precursor vector (ΔGrVSV-CCHFV-GPC) forming a Crimean-Congo Hemorrhagic Fever glycoprotein/antibody complex with Crimean-Congo Hemorrhagic Fever glycoprotein specific antibodies present in the sample; and
    (b) detecting glycoprotein/antibody complexes.

* * * * *